(12) United States Patent
Von Pawel-Rammingen et al.

(10) Patent No.: US 12,006,530 B2
(45) Date of Patent: Jun. 11, 2024

(54) STREPTOCOCCAL PROTEASES

(71) Applicant: GENOVIS AB, Lund (SE)

(72) Inventors: Ulrich Von Pawel-Rammingen, Sävar (SE); Christian Spoerry, Umeå (SE)

(73) Assignee: Genovis AB, Lund (SE)

( * ) Notice: Subject to any disclaimer, the term of this patent is extended or adjusted under 35 U.S.C. 154(b) by 591 days.

(21) Appl. No.: 16/075,059

(22) PCT Filed: Feb. 3, 2017

(86) PCT No.: PCT/EP2017/052463
§ 371 (c)(1),
(2) Date: Aug. 2, 2018

(87) PCT Pub. No.: WO2017/134274
PCT Pub. Date: Aug. 10, 2017

(65) Prior Publication Data
US 2019/0345533 A1 Nov. 14, 2019

(30) Foreign Application Priority Data
Feb. 4, 2016 (SE) .................................. 1630021-2

(51) Int. Cl.
*A61K 39/09* (2006.01)
*C12N 9/64* (2006.01)
*C12Q 1/37* (2006.01)
*G01N 33/68* (2006.01)

(52) U.S. Cl.
CPC .............. *C12Q 1/37* (2013.01); *C12N 9/641* (2013.01); *G01N 33/6854* (2013.01)

(58) Field of Classification Search
CPC ....... G01N 33/6854; C12Q 1/37; C12N 9/641
See application file for complete search history.

(56) References Cited

U.S. PATENT DOCUMENTS

| | | | |
|---|---|---|---|
| 2005/0119464 | A1 | 6/2005 | Von Pawel-Rammingen et al. |
| 2010/0303781 | A1 | 12/2010 | Lars et al. |

FOREIGN PATENT DOCUMENTS

| | | |
|---|---|---|
| CN | 103946377 | 7/2014 |
| EP | 2949749 | 2/2015 |
| EP | 3411389 | 3/2021 |
| JP | 2008-542418 | 11/2008 |
| WO | 2002092818 | 11/2002 |
| WO | WO 2006069200 | 6/2006 |
| WO | WO 2009033670 | 3/2009 |
| WO | 2013037824 | 3/2013 |
| WO | 2015040125 | 3/2015 |

OTHER PUBLICATIONS

Lannergård et al., FEMS Microbiol Lett, 2006, 262:230-235.*
Yang et al., Microbes and Infection, 2011, 13:757-750.*
Allgaier et al. (2001) "Relatedness of Streptococcus suis Isolates of Various Serotypes and Clinical Backgrounds as Evaluated by Macrorestriction Analysis and Expression of Potential Virulence Traits" J Clin Microbiol. 39:445-453.
Baums et al. (2007) "Prevalence of Streptococcus suis Genotypes in Wild Boars of Northwestern Germany" Appl. Environ. Microbiol. 73:711-717.
Database UniProt [Online] Jun. 26, 2007, "SubName: Full= Uncharacterized protein {ECO:00003131 EMBL: ABQ42881.1}.", retrieved from EBI accession No. UNIPROT:A5JSJ3, Database accession No. A5JSJ3.
Database UniProt [Online] Apr. 5, 2011, "SubName: Full= Uncharacterized protein {ECO:00003131 EMBL: EFV98161.1}:", retrieved from EBI accession No. UNIPROT:E7S231, Database accession No. E7S231.
Jacobs et al. (1994) "Identification, Purification, and Characterization of a ThiolActivated Hemolysin (Suilysin) of *Streptococcus suis*" Infect. Immun. 62:1742-1748.
Prokesová et al. (1992) "Cleavage of human immunoglobulins by serine proteinase from *Staphylococcus aureus*" Immunol. Lett. 31:259-265.
Rawlings et al. (2014) "The RIG-I ATPase core has evolved a functional requirement for allosteric stabilization by the Pincer domain" Nucleic Acids Res. 42.
Seele et al. (2013) "Identification of a Novel Host-Specific IgM Protease in *Streptococcus suis*" J. Bacteriol. 195:930-940.
Seele et al. (2015) "The immunoglobulin M-degrading enzyme of *Streptococcus suis*, IdeSsuis, is involved in complement evasion" J. Vet. Res. 46:45.
Smith et al. (1996) "Mutants of *Streptococcus suis* Types 1 and 2 Impaired in Expression of Muramidase-Released Protein and Extracellular Protein Induce Disease in Newborn Germfree Pigs" Infect. Immun. 64:4409-4412.
Smith et al. (1999) "Identification and Characterization of the cps Locus of *Streptococcus suis* Serotype 2: the Capsule Protects against Phagocytosis and Is an Important Virulence Factor" Infect. Immun. 67:1750-1756.
Spoerry et al. (2016) "Identification and Characterization of IgdE, a Novel IgG-degrading Protease of *Streptococcus suis* with Unique Specificity for Porcine IgG" Journal of Biological Chemistry, 291(15):7915-7925.
Unterweger et al. (2014) "Clinics, diagnosis and prophylaxis of a *Streptococcus suis* serotype 7 farm problem" Berl. Münch Tierarztl. Wochenschr. 127:194-201.
Vincents et al. (2011) "Cleavage of IgG1 and IgG3 by gingipain K from Porphyromonas gingiva/is may compromise host defense in progressive periodontitis" FASEB J. 10:3741-3750.
Von Pawel-Rammingen et al. (2002) "IdeS, a novel streptoccal cysteine proteinase with unique specificity for immunoglobulin G" EMBO J. 21:1607-1161.

(Continued)

*Primary Examiner* — Bin Shen
(74) *Attorney, Agent, or Firm* — Brian E. Davy; Bozicevic, Field & Francis LLP

(57) ABSTRACT

The invention relates to new Streptococcal proteases designated IgdE which display IgG degrading cysteine protease activity. The invention further relates to in vitro methods of cleaving IgG using the described Streptococcal proteases, using the methods to generate Fc and Fab fragments, and using the methods to detect IgG.

9 Claims, 18 Drawing Sheets

Specification includes a Sequence Listing.

(56) References Cited

OTHER PUBLICATIONS

Wisselink et al. (2002) "Multiplex PCR Assays for Simultaneous Detection of Six Major Serotypes and Two Virulence-Associated Phenotypes of *Streptococcus suis* in Tonsillar Specimens from Pigs" J. Clin. Microbiol. 40:2922-2929.
Zhang et al. (2010) "Identification and characterization of IgA1 protease from *Streptococcus suis*" Vet. Microbiol. 140:171-175.
Hulting et al. (2009) "Two novel IgG endopeptidases of *Streptococcus equi*" FEMS Microbiol Lett., 298:44-50.
Altschul, (1993) "A Protein Alignment Scoring System Sensitive at All Evolutionary Distances" Journal of Molecular Evolution 36:290-300.
Altschul et al., (1990) "Basic Local Alignment Search Tool" Journal of Molecular Evolution, 215:403-410.
Devereux et al. (1984) "A comprehensive set of sequence analysis programs for the VAX" Nucleic Acids Research, 12:1 387-395.
European Application EP17703958.3 filed Feb. 3, 2017.
Green et al., (1981) "Peptidyl Diazomethyl Ketones are Specific Inactivators of Thiol Proteinases" Journal of Biological Chemistry, 256: 4 1923-1928.
Henikoff et al., (1992) "Amino acid substitution matrices from protein blocks" Proceedings of the National Academy of Sciences of the United States of America 89: 10915-10919.
Karlin et al. (1993) "Applications and statistics for multiple high-scoring segments in molecular sequences" Proceedings of the National Academy of Sciences of the United States of America, 90: 5873-5787.
Lei et al. (2003) "Histidine and Aspartic Acid Residues Important for Immunoglobulin G Endopeptidase Activity of the Group A *Streptococcus* Opsonopagocytosis-Inhibiting Mac Protein" 71(5):2881-2884.
Sambrook, (1989) "Molecular Cloning: A Laboratory Manual" Cold Spring Harbor Laboratory Press.
SE1630021-2 Application as filed Feb. 4, 2016.
SE1630021-2, Search Results dated Sep. 9, 2016.
Spoerry et al. (2016) "Novel IgG-Degrading Enzymes of the IgdE Protease Family Link Substrate Specificity to Host Tropism of *Streptococcus* Species" PloS One, 11(10):e0164809, pp. 1-20.
STN Database DGENE; AN ADV79330 (retrieved on Sep. 2, 2016).
STN Database DGENE: AN ADV78978 (retrieved on Sep. 2, 2016).
STN Database DGENE: AN AES81464 (retrieved on Sep. 2, 2016).
STN Database DGENE: AN AES81463 (retrieved on Sep. 2, 2016).
Zhao et al. (2009) "Structural and mutational studies on the importance of oligosaccharide binding for the activity of yeast PNGase" 19(2):118-125.
Extract from sequence list of WO2002092818A2 (Glaser et al., Nov. 21, 2002), 6 pages.
Extract of sequence list of WO2006069200A2 (Chiron Corporation, 2006), 3 pages.
Sequence alignments, May 16, 2022, 6 pages.
Supplementary table of Yang et al., 2011, Microbes and Infection, 13: 77-760 (D), May 16, 2022, 2 pages.

* cited by examiner

SEQUENCE LISTING

<160> NUMBER OF SEQ ID NOS: 23

<210> SEQ ID NO 1

<211> LENGTH: 1084
<212> TYPE: PRT
<213> ORGANISM: Streptococcus suis

<400> SEQUENCE: 1

Asp Glu Asn Ser His Leu Gln Ser Pro Lys Asn Thr Asn Lys Ile Glu
1               5                   10                  15

Val Leu Asn Trp Glu Ala Phe Ser Lys Lys Leu Lys Asp Tyr Ser Ser
            20                  25                  30

Asp Gln Arg Gln Phe His Val Leu Lys Leu Gly Phe Glu Asn Arg Leu
        35                  40                  45

Gly Thr Leu Ser Thr Arg Glu Glu Leu Glu Gly Phe Gly Lys Asn Asn
    50                  55                  60

Asn Phe Leu Val Ile Asn Gly Lys Val Thr Gln Asn Ile His Asp Phe
65                  70                  75                  80

Pro His Ile Leu Val Met Asn Lys Gly Asp Val Ile Ala His Asn Glu
                85                  90                  95

Glu Asp Tyr His Asn Gln Met Arg Glu Leu Arg Phe Ser Gly Asn Gly
            100                 105                 110

Asp Leu His Asn Ser Met Glu Pro Lys Arg Ile His Ala Leu Phe Lys
        115                 120                 125

Ile Glu Leu Asp Ser Asn Lys Arg Gln Leu Leu Asn Ala Ala Gly Leu
    130                 135                 140

Gly Thr Ala Glu Asn Ser Leu Lys Asn Ile Asn Gly Met Thr Ile Tyr
145                 150                 155                 160

Ser His Gly Leu Thr Val Asp Asn Lys Tyr Tyr Glu Asp Tyr Ser Lys
                165                 170                 175

Tyr Thr His Asn Ser Val Lys Asn Ile Asn Val Thr Lys Glu Arg Phe
            180                 185                 190

Ile Ala Asn Asp Asp Leu Ile His Lys Leu Ile Glu Ser Ser Glu Ala
        195                 200                 205

Met Lys Gln Ser Ser Glu Arg Asp Lys Val Lys Ala Phe Val Gln Tyr
    210                 215                 220

Val Ala Asn His Thr Thr Tyr Asp Trp Glu Ala Ala Asn Lys Ala Val
225                 230                 235                 240

Gln Asn Tyr Ala Asp Ile Asn Tyr Tyr Leu Gly Ser Asp Leu Phe Ala
                245                 250                 255

Val Thr Glu Arg Gln Lys Ala Met Cys Val Gly Phe Ser Thr Thr Ala
            260                 265                 270

Ala Arg Ala Phe Asn Met Leu Gly Leu Pro Ala Tyr Val Val Val Gly
        275                 280                 285

Lys Asn Ala Glu Gly Val Pro His Ala Thr Ala Arg Val Tyr Tyr Asp
    290                 295                 300

Lys Lys Trp His Thr Ile Asp Gly Thr Gly Phe Ile Thr Gly Asn Lys
305                 310                 315                 320

His Gln Arg Ser Ala Lys Tyr Ser Glu Lys His Phe Ser Thr Ile Gly
                325                 330                 335

Glu Asp Ser Tyr Asp Val Val Glu Ala Gly Gln Glu Pro Lys Ala Glu
            340                 345                 350

Arg Asn Tyr Met Ile Ile Asp Ser Asn Tyr Glu Ser Trp Ala Met Lys
        355                 360                 365

Gln Lys Thr Ala Asp Leu Leu Leu Phe Asn Lys Glu Lys Ser Leu Val
    370                 375                 380

Gly Leu Asp Tyr Ile Ala Tyr Val Glu Pro Thr Tyr Ile Thr Glu Asn

-continued

```
              385                 390                 395                 400
Lys Lys Asn His Leu Leu Asp Ile Tyr Lys Ala Leu Lys Arg Lys Val
                405                 410                 415
Glu Glu Thr Lys Ala Thr Asp Lys Asp Lys Asp Lys Gln Glu
                420                 425                 430
Gly Tyr Asp Arg Val Leu Gln Phe Val Asn Ser Asp Ile Asp Lys Leu
                435                 440                 445
Ser Ala Leu Ser Lys Ile Thr Glu Glu Phe Lys Ala Leu Glu Asn
            450                 455                 460
Ser Met Asp Leu Ala Arg Val Phe Leu Gly Gln Met Asn Ala Lys Ala
465                 470                 475                 480
Gly Lys Glu Phe Ser Glu Gly Glu Thr Tyr Gln Ser Tyr Leu Lys Asn
                485                 490                 495
Arg Gln Lys Asn Asn Thr Asn Ser Asp Asp Arg Asn Arg Asn Glu
                500                 505                 510
Leu Gln Glu Asn Gln Ala Asn Ser Asp Glu Val Ser Gln Asn Ser Lys
            515                 520                 525
Asp Ala Ser Ala Pro Ser Val Asn Ser Ala Gln Gln Ser Glu Glu Leu
530                 535                 540
Glu Gly Thr Pro Ser Thr Gln Glu Thr Ile Ser Ala Ala Pro Ser Gln
545                 550                 555                 560
Gln Thr Pro Ala Ala Pro Lys Ala Leu Gln Ala Lys Thr Glu Leu Glu
                565                 570                 575
Asp Lys Thr Glu Thr Ser Ser Leu Gly Asn Thr Glu Met Val Ser Pro
            580                 585                 590
Ser Ser Glu Thr Ala Gln Asn Thr Val Asp Ser Lys Glu Glu Ser Asp
            595                 600                 605
Ala Lys Leu Pro Tyr Val Glu Pro Ser Ser Lys Glu Ser Ser Glu Ala
            610                 615                 620
Gln Val Asn Thr Val Ser Ser Pro Gln Val Ser Ser Ala Ser Pro Thr
625                 630                 635                 640
Ser Ser Glu Thr Ile Ser Thr Asp Thr Val Thr Ala Ser Gln Glu Lys
                645                 650                 655
Ala Glu Ser Arg Val Ser Ala Pro Gln Val Ile Ser Ala Ser Gln Thr
                660                 665                 670
Ser Pro Glu Thr Asn Ser Ala Glu Val Val Thr Thr Ser Gln Glu Val
            675                 680                 685
Ala Lys Ala Pro Val Ser Ala Pro Gln Val Ser Ser Glu Ile Gln Thr
            690                 695                 700
Leu Ser Glu Thr Ala Pro Thr Glu Val Ala Thr Glu Ala Pro Glu Leu
705                 710                 715                 720
Ser Ala Leu Glu Ser Asn Pro Ala Pro Gln Thr Ser Leu Glu Thr Thr
                725                 730                 735
Pro Thr Glu Glu Val Thr Glu Thr Pro Glu Pro Ser Val Val Glu Ser
                740                 745                 750
Asn Ser Ala Ser Pro Thr Ser Pro Glu Thr Asn Ser Ala Glu Ala Val
            755                 760                 765
Thr Thr Ser Gln Glu Met Ala Glu Pro Ser Val Ser Val Pro Gln Val
            770                 775                 780
Ser Ser Glu Ile Pro Thr Ser Ser Glu Thr Ala Pro Ala Glu Val Ala
785                 790                 795                 800
Thr Glu Val Ser Glu Glu Ser Ser Ser Ala Ser Gln Pro Ser Pro Glu
                805                 810                 815
```

Thr Thr Pro Thr Glu Thr Val Thr Thr Ser Gln Val Ala Glu Ala
            820                 825                 830

Pro Val Ser Ala Pro Gln Val Ser Glu Ile Pro Thr Ser Pro Glu
            835                 840                 845

Thr Ala Ser Thr Glu Val Val Ala Lys Gln Glu Val Ala Asp Ser
850                 855                 860

Pro Val Ser Ala Pro Gln Val Ile Ser Glu Ile Pro Thr Ser Glu
865                 870                 875                 880

Thr Ala Pro Ala Glu Val Ala Thr Glu Val Thr Pro Ser Val Val
            885                 890                 895

Ala Ser Ser Ser Ala Ser Pro Thr Ser Pro Glu Ala Asn Ser Thr Glu
            900                 905                 910

Val Val Val Ala Lys Gln Glu Val Ala Asp Pro Leu Val Ser Ala Pro
            915                 920                 925

Gln Thr Ser Ser Ala Ser Leu Thr Leu Glu Val Pro Lys Asn Glu His
            930                 935                 940

Leu Asp Glu Lys Ala Asp Ala Thr Thr Pro Asn Gly Val Glu Ala Asn
945                 950                 955                 960

Thr His Glu Ala Val Ser Val Pro Thr Ser Asp Ile Arg Val Gln Asp
            965                 970                 975

Ala Gly Ser Asp Thr Val Pro Gln Pro Tyr Ser Leu Ser Ala Thr Leu
            980                 985                 990

Phe Glu Glu Ala Ile Ser Thr Val Glu Pro Val Gly Val Ala Thr Ser
            995                 1000                1005

Ser Gln Glu Arg Ser Ala Val Ala Gly Lys Val Lys Val Pro Thr
            1010                1015                1020

Ser Leu Glu Arg Ser Asn Asn Ser Val Glu Glu Glu Lys Val Val
            1025                1030                1035

Asp Ser Asn Ala Thr Ile Glu Asn Arg Glu Pro Glu Lys Lys Glu
            1040                1045                1050

Ile Leu Thr Ser Glu Asn Val Leu Asn Ser Leu Val Thr Ile Trp
            1055                1060                1065

Val Ala Leu Ser Thr Ser Phe Phe Met Arg Tyr Phe Ser Arg Gly
            1070                1075                1080

Lys

<210> SEQ ID NO 2
<211> LENGTH: 3255
<212> TYPE: DNA
<213> ORGANISM: Streptococcus suis

<400> SEQUENCE: 2
gatgaaaact cacatttaca atcgccaaaa aacaccaata aaatagaggt tctgaactgg      60
gaagcatttt ctaaaaaatt gaaagactac tcctcggacc aacgacaatt tcatgttttg     120
aaattaggat ttgaaaatcg actgggaaca ttatcaactc gggaagaatt ggaagaattt     180
ggtaaaaaca acaatttttt ggtaatcaat ggtaaagtta ctcaaaatat tcatgacttt     240
ccacatatcc ttgttatgaa caagggtgat gttattgctc ataatgagga agattatcat     300
aatcagatga gagagttgag gttttcggga aatggcgact acataatag tatggagcca     360 aaacggattc atgcactatt taagattgag cttgactcca ataaacggca gttattaaat     420
gctgcgggtc taggaactgc tgagaatagt ttgaaaaata ttaatggaat gactatttac     480
tcgcatggtc ttacagttga ataaagtac tatgaggatt atagtaaata tactcataat     540

```
tcagttaaaa atataaacgt taccaaagag cgttttatag caaatgatga cttgattcat    600
aagttgatag agtcctcaga agctatgaag caatcaagtg aacgcgataa agttaaggca    660
tttgttcagt atgttgccaa tcatacaaca tatgattggg aagctgctaa taaggctgtt    720
caaaattatg cagacatcaa ttactactta ggatcagatt tgttcgcggt tactgaacgt    780
cagaaagcga tgtgtgtagg tttcagcact actgcggccc gtgcattaa tatgttaggg     840 cttcctgctt atgttgttgt tgggaaaaat gcagaaggtg tcccgcatgc tacagcgcgt    900
gtttattatg ataaaaagtg gcacaccatt gacggtacag gttttattac agggaataag    960
catcagcgct cagctaaata tagcgagaaa cacttttcta ctattggtga ggatagttat   1020
gatgttgttg aggcaggaca ggagcctaag gcggagcgta actacatgat tattgatagt   1080
aattatgaga gttgggctat gaaacaaaaa acagcagatt tactgttgtt caacaaagaa   1140
aagtccttgg ttggtttgga ttatattgca tatgttgagc caacttatat aacagaaaat   1200
aagaaaaatc atttgctaga catctataaa gctttgaaac gtaaagtaga agaaacgaaa   1260
gcaacggata aagacgataa agatgataaa caagaggggt atgatcgtgt tttacaattt   1320
gtcaattctg atattgataa attgagtgct ctctccaaga ttacagaaga agaatttaaa   1380
gcactcgaaa attcaatgga tttagctcga gtgttcttgg ggcaaatgaa tgcgaaggct   1440
ggaaaagaat tttcggaagg agaaacttat caaagttatc taaagaatcg tcagaaaaat   1500
aacacaaatt ctgatgatga tagaaaccga aatgaattgc aagaaaacca agctaattct   1560
gatgaagtca gccaaaattc caaggatgct tcggctccaa gtgttaattc tgcacagcaa   1620
tctgaggagc ttgaaggaac tccttcaaca caggaaacaa tctcagctgc tccttctcaa   1680
caaacaccag cagctcctaa agcactacaa gctaaaactg agttagagga taaaacagag   1740
acttcatctt taggaaatac agagatggtt tcaccgagtt cagaaacagc tcagaataca   1800
gttgattcta aggaagaaag tgatgctaaa ttaccatatg ttgagccttc atccaaagaa   1860
tcgagtgaag cgcaggttaa tacagtttcc tctccacaag taagttctgc atccccaact   1920
tcatcagaaa ctatttctac agatacggta acagctagtc aagaaaaagc tgaatcacgg   1980
gtttctgccc cacaagtaat ttcagcatct caaacttcac cggaaactaa ttctgccgag   2040
gtggtaacaa ctagtcaaga agtagctaaa gcaccggttt ctgctccaca agtaagttct   2100
gaaatccaaa ctttatcaga aacagctcct acagaggtgg caacagaagc accggaatta   2160
agtgcacttg agagtaatcc agcacctcaa acttcattgg aaacaactcc tacagaggag   2220
gtaacagaaa caccggaacc aagtgtagtt gagagtaatt cagcatcccc aacttcaccg   2280
gaaactaatt ctgcagaggc agtaacaact agtcaagaaa tggctgaacc ttcggtttct   2340
gttccacaag taagttctga atcccaact tcatcagaaa cagctccagc agaagtggca    2400
acagaagtat cggaagagag tagttcagca tctcaacctt caccggaaac aactcctaca   2460
gagacggtaa caactagtca agaagtagct gaagcaccgg tttctgctcc acaagtaagt   2520
tctgaaatcc caacttcacc ggaaacagct tctacagagg tggtggtagc taaacaagaa   2580
gtagctgact caccggtttc agctccacaa gtaatttctg aaatcccaac ttcatcagaa   2640
acagctccag cagaagtggc aacagaagta acagaaccag tgtagttgc gagtagttca    2700 gcatccccaa cttcaccgga agctaattct acagaggtgg tggtagctaa acaagaagta   2760
gctgacccca ctggtttctgc tccacaaaca agttctgctt cacttacttt agaggttcct   2820
aaaaatgaac atttagacga gaaagcagat gcaactacgc caaatggagt tgaagcaaat   2880
```

```
actcatgagg cagtttctgt tccgacatca gatattcgtg ttcaagatgc tggttcagac   2940
acggtgcctc aaccttactc tttatctgcg acattgtttg aagaagcaat ttcaacagtt   3000
gagcctgtag gtgttgcaac ttcttctcaa gagagaagtg cagtagctgg caaggtgaaa   3060
gtgcctacct ctcttgaacg tagtaacaat tctgttgagg aagaaaaagt ggtcgattca   3120
aatgcaacaa ttgagaatcg agagccagag aaaaaagaga tccttacttc ggaaaatgta   3180
cttaacagct tagtaacaat ttgggtagct ttatctacta gtttcttcat gagatatttt   3240
tctcgaggaa aataa                                                   3255
```

<210> SEQ ID NO 3
<211> LENGTH: 586
<212> TYPE: PRT
<213> ORGANISM: Streptococcus agalactiae

<400> SEQUENCE: 3

```
Asn Gln Asn Asn Ile Gln Glu Thr Asn Leu Val Glu Lys Asn Ser Glu
1               5                   10                  15

Asp Lys Phe Ile Gln Glu Leu Asn Arg Tyr Lys Thr Glu Ile Pro Asn
            20                  25                  30

Phe Lys Gly Phe Asn Val Trp Ile Leu Gly Asp Lys Gly Tyr Tyr Lys
        35                  40                  45

Asn Leu Ile Asn Leu Glu Glu Ile Lys Asn Ile Gln Ala Thr Leu Lys
    50                  55                  60

Lys Glu Arg Asn Glu Glu Tyr Val Phe Val Lys Leu Asn Gly Lys Ile
65                  70                  75                  80

Ala His Asp Thr Thr Val Phe Leu Met Asn Lys Lys His Lys Leu Leu
                85                  90                  95

Lys Asn Ile Glu Glu Phe Lys Thr Ile Thr Gln Lys Arg Leu Thr Glu
            100                 105                 110

Arg Gly Lys Phe Pro Tyr Asp Thr Val His Ser Thr Phe Glu Ile Lys
        115                 120                 125

Asp Glu Asn Phe Ile Met Glu Arg Leu Lys Ser Ser Gly Leu Ser Met
    130                 135                 140

Gly Lys Pro Val Asp Tyr Met Gly Val Asn Gly Ile Pro Ile Tyr Thr
145                 150                 155                 160

Lys Thr Leu Ser Ile Asp Asn Lys Phe Ala Phe Glu Asn Asn Ser Lys
                165                 170                 175

Asp Ser Ser Tyr Ser Ser Asn Ile Asn Ile Ser Glu Asp Lys Ile Lys
            180                 185                 190

Glu Asn Asp Gln Lys Ile Leu Asp Leu Ile Val Lys Ser Gly Ala Asn
        195                 200                 205

Asn Gln Asn Leu Thr Asp Glu Glu Lys Val Ile Ala Phe Thr Lys Tyr
    210                 215                 220

Ile Gly Glu Ile Thr Asn Tyr Asp Asn Glu Ala Tyr Arg Ala Arg Asn
225                 230                 235                 240

Val Asp Thr Glu Tyr Tyr Arg Ala Ser Asp Leu Phe Ser Val Thr Glu
                245                 250                 255

Arg Lys Leu Ala Met Cys Val Gly Tyr Ser Val Thr Ala Ala Arg Ala
            260                 265                 270

Phe Asn Ile Met Gly Ile Pro Ser Tyr Val Val Ser Gly Lys Ser Pro
        275                 280                 285

Gln Gly Ile Ser His Ala Ala Val Arg Ala Tyr Tyr Asn Arg Ser Trp
    290                 295                 300
```

His Ile Ile Asp Ile Thr Ala Ser Thr Tyr Trp Lys Asn Gly Asn Tyr
305                 310                 315                 320

Lys Thr Thr Tyr Ser Asp Phe Ile Lys Glu Tyr Cys Ile Asp Gly Tyr
            325                 330                 335

Asp Val Tyr Asp Pro Ala Lys Thr Asn Asn Arg Phe Lys Val Lys Tyr
            340                 345                 350

Met Glu Ser Asn Glu Ala Phe Glu Asn Trp Ile His Asn Asn Gly Ser
        355                 360                 365

Lys Ser Met Leu Phe Ile Asn Glu Ser Ala Ala Leu Lys Asp Lys Lys
    370                 375                 380

Pro Lys Asp Asp Phe Val Pro Val Thr Glu Lys Glu Lys Asn Glu Leu
385                 390                 395                 400

Ile Asp Lys Tyr Lys Lys Leu Leu Ser Gln Ile Pro Glu Asn Thr Gln
            405                 410                 415

Asn Pro Gly Glu Lys Asn Ile Arg Asp Tyr Leu Lys Asn Glu Tyr Glu
        420                 425                 430

Glu Ile Leu Lys Lys Asp Asn Leu Phe Glu His Glu His Ala Glu Phe
    435                 440                 445

Lys Glu Ser Leu Asn Leu Asn Glu Ser Phe Tyr Leu Gln Leu Lys Lys
    450                 455                 460

Glu Glu Lys Lys Pro Ser Asp Asn Leu Lys Lys Glu Lys Pro Arg
465                 470                 475                 480

Glu Asn Ser Val Lys Glu Arg Glu Thr Pro Ala Glu Asn Asn Asp Phe
            485                 490                 495

Val Ser Val Thr Glu Lys Asn Asn Leu Ile Asp Lys Tyr Lys Glu Leu
        500                 505                 510

Leu Ser Lys Ile Pro Glu Asn Thr Gln Asn Pro Gly Glu Lys Asn Ile
    515                 520                 525

Arg Asn Tyr Leu Glu Lys Glu Tyr Glu Glu Leu Leu Gln Lys Asp Lys
    530                 535                 540

Leu Phe Lys His Glu Tyr Thr Glu Phe Thr Lys Ser Leu Asn Leu Asn
545                 550                 555                 560

Glu Thr Phe Tyr Ser Gln Leu Lys Glu Gly Glu Met Lys Leu Ser Glu
            565                 570                 575

Asn Pro Glu Lys Gly Glu Thr Asn Thr Asn
        580                 585

<210> SEQ ID NO 4
<211> LENGTH: 1761
<212> TYPE: DNA
<213> ORGANISM: Streptococcus agalactiae

<400> SEQUENCE: 4
aatcaaaata atattcaaga aactaatcta gttgaaaaaa acagtgaaga taagtttatt        60
caagagttaa ataggtataa aacagagata ccaaatttca aaggttttaa tgtttggatt       120
ttaggtgata aaggttatta caaaaacctt atcaatttag aagaaattaa aaatatccaa       180
gctacattaa aaaagaaag aaatgaagaa tatgtctttg tcaaattaaa tgggaaaatc       240
gcacatgata caacagtatt cttgatgaat aaaaaacata attacttaa aaatatagag       300 gaatttaaga cgataaccca aaaaggcta actgagagag aaagttccc atatgatacc        360 gttcattcta cgtttgaaat taaggatgaa aactttatca tggaaagatt gaaatcatca       420
gggttatcta tgggtaaacc agttgattat atgggcgtaa atggtatccc tatttacact       480
aaaacattat ctatagataa taagtttgcc tttgaaaata attcaaaaga ttcttcatat       540

```
tcttcaaaca ttaatattag tgaagataaa ataaaagaaa atgaccaaaa aattctagat      600
ttaatagtta aatctggagc taataatcaa aacttaacag atgaagaaaa agtaattgct      660
ttcactaaat atataggtga ataactaat tatgacaatg aagcttacag agctagaaat       720
gtcgacacag aatattacag agcttcagat ttattttctg taacagaaag aaaacttgct      780
atgtgcgttg gctatagtgt aacagccgct agggcattta atattatggg gataccta gt     840 tatgtcgttt ctggtaaaag tcctcaagga atatctcatg cagctgtgag agcgtattat      900
aatagaagtt ggcatatcat agatatcaca gccagtacat attggaaaaa tggtaattac      960
aaaacaacgt attccgattt tattaaagaa tactgtatag atggttatga cgtttatgat     1020
cccgcaaaaa caaataatag atttaaagtt aagtatatgg aatcaaatga agcgtttgaa     1080
aattggatac ataataatgg aagcaaatct atgttattta ttaatgaatc tgcagctcta     1140
aaagataaaa aaccaaaaga tgattttgta ccagtaacag aaaaagaaaa aaacgagctg     1200
atagataagt ataaaaaatt attgtcacag attcctgaaa acacacaaaa tccaggagaa     1260
aaaaacataa gagattattt gaaaaatgaa tatgaagaaa tattaaagaa agataaattta    1320 tttgagcatg aacatgcaga atttaaagaa agtctaaatt taaatgaatc attctaccta     1380
caattaaaga agaagaaaaa gaaaccgagt gataatctca aaaagaaga aaaaccaaga      1440 gaaaattcag taaagagag ggagactcca gctgaaaaca atgatttgt ttcagtaaca       1500 gaaaaaaaca acttgattga taaatataaa gaattattat caaaaatccc agagaataca    1560
caaaatcctg gggaaaagaa tatacgaaat tatctagaga aagaatatga agaactacta    1620
caaaaagata aattattcaa gcatgagtac acagagttta caaaaagtct aaatttgaat    1680
gaaacattct attcacaatt aaaagaagga gaaatgaaac taagtgaaaa tcccgaaaaa   1740
ggagaaacga acacgaatta g                                             1761
```

<210> SEQ ID NO 5
<211> LENGTH: 493
<212> TYPE: PRT
<213> ORGANISM: Streptococcus porcinus

<400> SEQUENCE: 5

Ala Val Leu Ala Arg Glu Asn Ser Asn Ser Gly Gln Leu His Pro Glu
1               5                   10                  15

Ala Arg Gln Ile Lys Ala Val Asp Phe Gln Glu Phe Ser Lys Lys Leu
                20                  25                  30

Lys Glu Glu Ile Ser Glu Asn Gln Gln Phe His Val Phe Lys Leu Gly
            35                  40                  45

Met Asn Asn Tyr Tyr Arg Ser Gly Ile Arg Ile Asn Glu Leu Asn Asn
        50                  55                  60

Leu Ala Thr Glu His Asp Phe Ile Leu Val Asn Asp His Ala Ser His
65                  70                  75                  80

Lys Lys Tyr Asp Val Pro His Ile Phe Ile Met Asn Lys Gly Asp Val
                85                  90                  95

Ile Val Pro Ser Lys Glu Lys Tyr Asp Glu Gln Met Arg Glu Val Lys
            100                 105                 110

Phe Ala Gly Asp Gln Pro Asn Ala Gln Arg Gln Arg Ile His Ala Leu
        115                 120                 125

Phe Glu Ile Gly Leu Asp Ser Asn Lys Arg Gln Leu Leu Asn Ala Ala
    130                 135                 140

Gly Leu Gly Thr Ala Glu Asn Thr Leu Ala Lys Val Asp Gly Phe Thr

```
                145                 150                 155                 160
Ile Tyr Ser His Gly Leu Thr Val Asp Asn Lys Tyr Tyr Glu Asp Tyr
                165                 170                 175

Ile Arg Phe Asn Lys Asn Glu Asn Ile Asn Ile Thr Lys Glu Arg Phe
                180                 185                 190

Thr Ala Asn Asp Asn Leu Ile His Asn Leu Ile Thr Glu Ser Thr Ala
                195                 200                 205

Lys Val Gln Thr Asn Asp Arg Asp Lys Val Lys Ala Phe Val Met Tyr
    210                 215                 220

Val Ala Asn His Thr Ile Tyr Asp Trp Ile Ala Ala Asn Asn Ala Val
225                 230                 235                 240

Ser Asn Ile Ser Asp Val Asn Tyr Tyr Leu Gly Ser Asp Leu Phe Ser
                245                 250                 255

Ile Thr Glu Arg Lys Lys Ala Met Cys Val Gly Phe Ser Thr Thr Ala
                260                 265                 270

Ala Arg Ala Phe Asn Met Leu Gly Ile Pro Ala Tyr Val Val Gly
    275                 280                 285

Lys Asn Ala Gln Gly Val Asp His Ala Thr Arg Ala Tyr Tyr Asn
    290                 295                 300

Gly Lys Trp His Thr Ile Asp Gly Thr Gly Phe Ile Asn Asp Lys Ala
305                 310                 315                 320

Ser Arg Ser Thr Ile Tyr Ser Glu Asn His Phe Tyr Ser Ile Gly Glu
                325                 330                 335

Asp Ser Tyr Asn Ile Val Asp Val Asn Asp Glu Gln Ile Ala Phe Asp
                340                 345                 350

Lys Asn Tyr Met Lys Ile Asp Lys Val Phe Glu Glu Trp Ala Gln Lys
                355                 360                 365

Gln Pro Thr Ala Asp Leu Leu Ile Asn Lys Asp Lys Ser Leu Val
    370                 375                 380

Pro Ser Asn Tyr Val Ala Tyr Val Ala Pro Val Ile Val Asp Asn Asn
385                 390                 395                 400

Arg Lys Gly Ser Leu Thr Gln Ile Tyr Gln Asn Leu Lys Gln Val Met
                405                 410                 415

Glu Ser Ser Ser Gln Lys Ala Ser Leu Thr Ser Leu Leu Asn Thr Ala
                420                 425                 430

Thr Ala Asp Ile Ala Lys Leu Gln Thr Ser Ser Gln Leu Thr Gln Glu
                435                 440                 445

Asp Tyr Asn Gln Ile Gln Asn Ser Met Lys Ser Val Leu Ser Phe Phe
    450                 455                 460

Trp Gln Leu Asp Lys Asp Ser Ala Thr Asn Phe Glu Asn Ser Glu Asp
465                 470                 475                 480

Tyr Lys Lys Tyr Leu Thr Glu Thr Lys Asn Ala Gly Asn
                485                 490

<210> SEQ ID NO 6
<211> LENGTH: 1482
<212> TYPE: DNA
<213> ORGANISM: Streptococcus porcinus

<400> SEQUENCE: 6
gctgttcttg cgagagaaaa tagtaactcg ggacaattac atccagaagc tagacaaata     60
aaagcagtgg attttcagga gttttcaaaa aaattaaagg aagaaatttc agaaaaccag    120
cagtttcacg tttcaagct gggcatgaat aattattata ggtcaggcat ccgcataaat    180
```

-continued

| | |
|---|---|
| gaactaaata atttagcaac tgagcatgac tttattcttg ttaatgacca tgctagccat | 240 |
| aagaaatatg atgttcctca tatctttatc atgaacaaag gagacgttat tgttcctagt | 300 |
| aaagaaaagt atgatgagca gatgagagag gtgaaattcg ccggtgatca acctaatgcg | 360 |
| caaagacaga gaattcatgc gctatttgaa atcggattgg attccaataa acgtcaatta | 420 |
| cttaacgctg cagggcttgg aaccgcagaa atactttag caaggttga tggctttaca | 480 |
| atctactctc atggcttgac ggttgataat aaatattatg aagactatat tcgttttaat | 540 |
| aaaaacgaaa acataaatat taccaaggaa cgctttactg ccaatgataa cttaatccat | 600 |
| aacttgataa ctgaatcaac agctaaagtt caaacaaatg accgagacaa agttaaagcg | 660 |
| tttgttatgt atgttgctaa ccacactatc tatgattgga tcgcagctaa caacgctgta | 720 |
| agtaatatat cagatgtcaa ctactatctt ggctctgatt tgttttcaat tactgaacgt | 780 |
| aagaaagcta tgtgtgttgg ttttagtact acagcagctc gtgcttttaa tatgttagga | 840 |
| attccagcct acgttgttgt tggaaaaaat gcacaaggtg tagaccatgc tacagctcgc | 900 |
| gcttactata acggtaaatg gcacactatt gacggtactg gttttattaa tgataaagct | 960 |
| tctcgctcta ctatttatag cgaaaatcac ttttactcta ttggcgaaga tagctataat | 1020 |
| atagttgatg ttaacgatga acaaatagct ttcgacaaaa actatatgaa aattgataag | 1080 |
| gtttttgaag aatgggctca aaaacaaccg acagcagact tattattgat taataaagat | 1140 |
| aaaatcattag tcccttcaaa ttatgtagcc tacgtcgcac cagtaattgt cgataacaat | 1200 |
| cgtaaaggtt ctcttacaca aatttatcaa aatttaaaac aagtaatgga atcatcttct | 1260 |
| caaaaggcat ccctaacctc tctcttaaat actgcaacag cagacattgc aaaacttcaa | 1320 |
| actagttctc aacttaccca agaagactat aaccagattc agaattctat gaaatctgtt | 1380 |
| ctctcgtttt tctggcagtt agataaggat tctgctacga attttgaaaa tagcgaagat | 1440 |
| tataaaaaat atctaacaga aacaaagaat gcaggtaact aa | 1482 |

<210> SEQ ID NO 7
<211> LENGTH: 517
<212> TYPE: PRT
<213> ORGANISM: Streptococcus equi

<400> SEQUENCE: 7

Met Glu Ala Trp Lys His Gly Ser Met Glu Ala Trp Lys His Gly Ser
1               5                   10                  15

Met Glu Ala Trp Lys His Gly Arg Thr Leu Cys Lys Gly Leu Leu Leu
            20                  25                  30

Gly Leu Ala Cys Gly Ala Ile Ser Met Ser Leu Val Val Lys Ser Thr
        35                  40                  45

Ile Val Val Ala Asp Asp Val Arg Leu Ser Glu Gln Ser Thr Val Ile
    50                  55                  60

Leu Asp Asn Thr Val Ser Asn Leu Ile Ser Glu Val Lys Asp Glu Leu
65                  70                  75                  80

Ala Lys Asn His Gln Asp Ala Leu Glu Ile Tyr Ile Leu Gly Glu Gly
                85                  90                  95

Ser Pro Lys Tyr Ser Gly Val Ser Pro Asp Arg Leu Gly Asp Tyr Ile
            100                 105                 110

Lys Asp Tyr Lys Pro Val Arg Leu Asn Gly Lys Val Ile His Gly Arg
        115                 120                 125

Ala Phe Phe Met Met Lys Lys Glu Asp Gln Leu Ile Ser Thr Lys Glu
    130                 135                 140

Glu Tyr Asp Arg Ile Ile Ala Glu Arg Phe Ser Asn Leu Glu Lys Phe
145                 150                 155                 160

Asp Tyr Pro Thr Ile His Tyr Thr Phe Asn Ala Glu Leu Lys Asp Lys
                165                 170                 175

Tyr Pro Tyr Leu Ser Leu Ile Leu Lys Ala Ser Gly Leu Ser Leu Ser
            180                 185                 190

Asp Ser Ile Asn Leu Gly Ser Thr Leu Gly Ile Asn Gly Val Thr Ile
        195                 200                 205

His Thr Gln His Leu Arg Ile Asp Asn Gln Phe Ala Tyr Arg Tyr Asn
    210                 215                 220

Gly Glu Asp Tyr Lys Gln Asp Ser His Ile Thr Phe Asp Arg Phe Lys
225                 230                 235                 240

Lys Asn Asp Asp Lys Leu Lys Glu Leu Ile Ala Thr Ser Gly Ala Asn
                245                 250                 255

Gln Glu Gly Leu Thr Asp Ala Gln Arg Val Lys Ala Tyr Val Leu Tyr
            260                 265                 270

Met Ala Asn His Val Asp Tyr Asp Trp Asp Ala Thr Arg Tyr Asn Pro
        275                 280                 285

Asp Tyr Leu Ile Phe Cys Gln Ala Ser Asp Leu Phe Ala Leu Thr Glu
    290                 295                 300

Arg Asn Lys Ala Met Cys Ile Gly Phe Ser Thr Ala Ala Arg Gly
305                 310                 315                 320

Leu Asn Leu Leu Gly Ile Pro Ser Tyr Val Thr Tyr Gly Lys Asn Arg
                325                 330                 335

Asp Gly Val Ala His Ala Thr Ile Arg Ala Phe Tyr Asp Lys Lys Trp
            340                 345                 350

Arg Thr Leu Asp Val Thr Gly Val Gly Arg Gly Lys Tyr Thr Glu Glu
        355                 360                 365

His Tyr Asp Asn Leu Asn Thr His Asp Tyr Lys Ile Phe Asp Leu Thr
    370                 375                 380

Lys Glu Thr Asn Val Asp Leu Asp Arg Gly Tyr Met Glu Ile Tyr Lys
385                 390                 395                 400

Asp Phe Glu Asp Trp Ile Leu Ser His Asn Thr Lys Glu Leu Leu Phe
                405                 410                 415

Ile Asn Gln Asp Ala Asn Ile Arg Asn Lys Val Ala Lys Asp Val Phe
            420                 425                 430

Lys Tyr Ile Gln Glu Ala Glu Lys Gln Ser Leu Ile Asp Lys Tyr Asn
        435                 440                 445

Glu Phe Ile Ile Arg Thr Ser Ala Leu Lys Ala Glu Phe Lys Thr Asp
    450                 455                 460

Arg Leu Lys Glu Ile Val Gly Ser Leu Val Ser Gln Ala Gln Glu Glu
465                 470                 475                 480

Leu Glu Asn Ile Lys His Ile Glu Val Met Thr Glu Asp Glu Lys Asp
                485                 490                 495

Gln Phe Glu Tyr Thr Leu Arg Asn Leu Gly Val Tyr Tyr Ser Gln Cys
            500                 505                 510

Glu Ser Ala Asn Gln
        515

<210> SEQ ID NO 8
<211> LENGTH: 1554
<212> TYPE: DNA
<213> ORGANISM: Streptococcus equi

<400> SEQUENCE: 8

```
atggaagcat ggaagcatgg aagcatggaa gcatggaagc atggaagcat ggaagcatgg      60
aagcatggaa ggactttgtg taaaggatta ttattaggat tagcatgtgg tgctatatct     120
atgtctttag tcgtcaagag tacaattgta gttgcggacg atgtaaggct tagcgagcag     180
tcgacggtca ttttagataa cactgtgtca atctgattta gtgaggttaa ggatgagtta     240
gccaaaaatc atcaggacgc attagaaatc tatatcttgg gggagggaag tccaaaatat     300
agtggagtgt ctcctgatcg tcttggtgac tacataaaag attataagcc tgtgcgttg      360
aatgggaagg tgatacatgg aagagcattt tcatgatga aaaaggaaga tcagctgata      420
tcaactaaag aagaatatga ccgcataata gcagaaaggt tttcaaatct ggaaaaattt     480
gattacccta ctatacacta tacctttaat gcggagctaa aggataaata cccttatctt     540
agtttaatac taaaagcgag tggtctttcc ttgtctgact caataaattt aggctcaaca     600
ctgggtataa atggcgttac tatccataca cagcatttac gtatcgacaa tcagtttgct     660
tatagataca atggagagga ttataaacaa gatagtcata taacgtttga ccgttttaag     720
aagaatgatg acaagttaaa ggaattgatt gcaacatctg agctaatcat agaggggctg     780
acagatgctc aacgagtaaa agccatgtc ttgtatatgg caaaccatgt tgattatgat      840
tgggatgcaa caagatataa tcctgattat ttaatatttt gtcaggcctc tgatttattt     900
gcacttacag agcgaaataa ggccatgtgt ataggcttta gtacagcagc tgcaagaggg     960
ttaaatctat tagggatacc atcttatgtg acctatggta aaaatagaga tggtgtagca    1020
catgcaacga tacgtgcttt ttacgataaa aagtggagaa cactagatgt tacaggagtt    1080
ggtagaggga atacacaga agaacattat gacaatctca atacgcacga ttataagatt     1140
tttgatttaa ctaaggaaac aaacgttgat ttagatcgtg ctatatggga gatctataag    1200
gattttgaag attggatcct ctcacacaat acgaaagagc tattatttat taatcaagat    1260
gcgaatatac gtaataaggt tgcaaaagat gttttttaaat acatacaaga ggctgagaag    1320
caatcgttaa tagataagta taatgaattc atcataagaa cgagtgcttt aaaggctgag    1380
ttcaaaactg acaggttaaa agaaatagtc ggaagtctag ttagtcaggc acaggaagaa    1440
ttagaaaata tcaagcatat tgaagttatg acagaagatg aaaaagatca gtttgaatat    1500
acactgagga atttaggagt atattattca caatgtgaaa gcgctaatca ataa          1554
```

<210> SEQ ID NO 9
<211> LENGTH: 497
<212> TYPE: PRT
<213> ORGANISM: Streptococcus pseudoporcinus

<400> SEQUENCE: 9

```
Arg Glu Asn Glu Asn Val Arg Gln Leu Gln Ser Glu Asn Lys Gln Met
1               5                   10                  15

Lys Ala Val Asn Leu Gln Glu Phe Ser Glu Lys Leu Lys Gly Glu Ile
            20                  25                  30

Ala Glu Asn Gln Gln Phe His Ile Phe Lys Leu Gly Leu Asn Asn Tyr
        35                  40                  45

Tyr Ile Gly Gly Val Arg Ile Asn Glu Leu Ser Asp Leu Ala Lys Asn
    50                  55                  60

His Asp Phe Ile Met Ile Asp Asn Arg Ala Thr His Asn Lys Tyr Gly
65                  70                  75                  80

Val Pro His Ile Ile Ile Met Asn Lys Asp Asp Val Ile Val His Asn
                85                  90                  95
```

Gln Glu Asp Tyr Asn Lys Glu Met Ala Glu Leu Thr Phe Ala Gly Asp
            100                 105                 110

Lys Pro Ile Gln Ser Asp Ser Tyr Leu Pro Gln Lys Lys Arg Ile His
        115                 120                 125

Ala Leu Phe Glu Ile Gly Leu Asp Ser Asn Arg Arg Gln Leu Leu Asn
    130                 135                 140

Ala Ala Gly Leu Lys Thr Pro Glu Asn Ser Val Ile Glu Leu Asp Thr
145                 150                 155                 160

Phe Lys Ile Tyr Ser His Gly Leu Ala Val Asp Asn Lys Tyr Tyr Asp
                165                 170                 175

Glu Tyr Ser His Phe Asn Asn Thr Asn Val Asn Ile Thr Lys Gln
            180                 185                 190

Arg Phe Thr Glu Asn Asp Asn Leu Ile His Asn Leu Ile Thr Thr Ser
        195                 200                 205

Thr Ala Lys Asp Gln Pro Thr Asp Arg Asp Lys Val Lys Thr Phe Val
210                 215                 220

Met Tyr Val Ala Asn His Thr Ile Tyr Asp Trp Asn Ala Ala Asn Asn
225                 230                 235                 240

Ala Val Ser Asn Ile Ser Asp Val Asn Tyr Tyr Leu Gly Ser Asp Leu
                245                 250                 255

Phe Ser Ile Thr Glu Arg Lys Lys Ala Met Cys Val Gly Phe Ser Thr
            260                 265                 270

Thr Ala Ala Arg Ala Phe Asn Met Leu Gly Ile Pro Ala Tyr Val Val
        275                 280                 285

Glu Gly Lys Asn Ala Gln Gly Val Asp His Ala Thr Ala Arg Val Tyr
    290                 295                 300

Tyr Asn Gly Lys Trp His Thr Ile Asp Gly Thr Gly Phe Ile Asn Gly
305                 310                 315                 320

Asn Arg Thr Arg Ser Thr Leu Tyr Thr Glu Ser His Phe Arg Ser Val
                325                 330                 335

Gly Glu Asp Ser Tyr Gln Leu Val Gly Leu Asn Glu Asp Ile Pro Phe
            340                 345                 350

Asp Arg Asn Tyr Met Lys Ile Asp Lys Val Tyr Glu Glu Trp Ala Pro
        355                 360                 365

Lys Gln Lys Thr Ala Asp Leu Leu Val Asn Lys Asp Lys Ser Leu
    370                 375                 380

Val Gly Leu Asp Arg Val Ala Tyr Val Glu Pro Val Tyr Val Asp Lys
385                 390                 395                 400

Asn Arg Gln Asp Ala Leu Thr Gln Ile Tyr Lys Lys Leu Lys Glu Thr
                405                 410                 415

Met Glu Ser Ser Ser Lys Lys Asn Pro Ser Ser Gly Gly Phe Ser Ser
            420                 425                 430

Leu Leu Gly Ser Ala Ser Ser Asp Ile Ala Lys Leu Glu Gly Ser Ser
        435                 440                 445

Gln Leu Thr Gln Glu Glu Tyr Asp Lys Ile His Arg Ser Met Thr Ser
    450                 455                 460

Ile Leu Thr Phe Phe Ala Gln Leu Asp Lys Asp Ala Ala Glu Ala Phe
465                 470                 475                 480

Glu Lys Gly Asn Asp Tyr Lys Asn Tyr Leu Ala Thr Thr Lys His Ala
                485                 490                 495

Gln

<210> SEQ ID NO 10

<211> LENGTH: 1494
<212> TYPE: DNA
<213> ORGANISM: Streptococcus pseudoporcinus

<400> SEQUENCE: 10

```
agagaaaatg aaaacgtaag acaattacaa tcagaaaata acaaatgaa agcagtaaac      60
ttgcaggaat tttcggagaa attaaaagga gaaattgctg aaaatcaaca atttcatatc    120
tttaaactag ggttgaataa ttattacata ggagggtac gcataaatga actgagtgat     180
ttagcgaaaa accatgattt tatcatgatt gataatcgtg ctacccataa taaatatgga    240
gtccctcata taattattat gaacaaagat gatgttattg tgcataatca agaagactat    300
aataagaaa tggcagagtt aacatttgca ggtgataaac cgatacaatc tgactcttac     360
cttccccaaa aaagagaat ccacgcactg tttgaaattg gtttagattc taatagacga     420
caattactta acgctgcagg acttaaaaca ccagaaaata gtgtaataga acttgatacc    480
tttaaaatct attctcatgg tttagcggtt gataataaat attatgacga atatagtcat    540
tttaataaca acacgaatgt caatattacc aagcagcgct ttactgagaa tgataactta    600
atccataact taataaccac gtcaacagct aaggatcagc caactgatcg cgacaaagtc    660
aaaacatttg ttatgtatgt ggctaaccat actatatatg actggaatgc cgcaaataat    720
gctgtaagta atatttcaga tgtcaactat tatcttggtt ctgatttgtt ttccattact    780
gaacgcaaga aagctatgtg tgtaggcttt agcactacag cagctcgtgc ttttaatatg    840
ctgggtatcc cagcctatgt ggttgaaggt aaaaacgcgc aaggtgtgga ccatgctact    900
gctcgtgtct actataatgg aaaatggcat accattgacg ggactggctt tattaacggt    960
aaccgcactc gctccactct ctataccgaa agccacttta ggtctgttgg agaagatagc   1020
tatcaactgg ttggtcttaa tgaggacata ccttttgata gaaactatat gaagattgat   1080
aaagtttacg aagaatgggc tcccaaacaa aagacggcag acctactatt agttaacaaa   1140
gataaatcat tagttggcct agaccgtgta gcctatgtcg aacctgtata tgttgacaag   1200
aaccgtcaag atgccctcac acaaatttac aaaaaattaa agaaacaat ggagtcctct    1260
tctaagaaga atccatcttc tggaggattc tcctctctct taggttctgc aagtagcgat   1320
attgcaaagc tggaaggctc ttctcaactt acacaagaag aatacgataa gattcatcgt   1380
tctatgacat ctattctcac ctttttttgca caactagata aagacgccgc cgaagccttt   1440
gaaaagggaa atgattataa gaattattta gcaacaacaa agcatgcaca gtaa         1494
```

<210> SEQ ID NO 11
<211> LENGTH: 432
<212> TYPE: PRT
<213> ORGANISM: Streptococcus suis

<400> SEQUENCE: 11

```
Asp Glu Asn Ser His Leu Gln Ser Pro Lys Asn Thr Asn Lys Ile Glu
1               5                   10                  15

Val Leu Asn Trp Glu Ala Phe Ser Lys Lys Leu Lys Asp Tyr Ser Ser
            20                  25                  30

Asp Gln Arg Gln Phe His Val Leu Lys Leu Gly Phe Glu Asn Arg Leu
        35                  40                  45

Gly Thr Leu Ser Thr Arg Glu Glu Leu Glu Glu Phe Gly Lys Asn Asn
    50                  55                  60

Asn Phe Leu Val Ile Asn Gly Lys Val Thr Gln Asn Ile His Asp Phe
65                  70                  75                  80
```

Pro His Ile Leu Val Met Asn Lys Gly Asp Val Ile Ala His Asn Glu
            85                  90                  95

Glu Asp Tyr His Asn Gln Met Arg Glu Leu Arg Phe Ser Gly Asn Gly
            100                 105                 110

Asp Leu His Asn Ser Met Glu Pro Lys Arg Ile His Ala Leu Phe Lys
            115                 120                 125

Ile Glu Leu Asp Ser Asn Lys Arg Gln Leu Leu Asn Ala Ala Gly Leu
            130                 135                 140

Gly Thr Ala Glu Asn Ser Leu Lys Asn Ile Asn Gly Met Thr Ile Tyr
145                 150                 155                 160

Ser His Gly Leu Thr Val Asp Asn Lys Tyr Tyr Glu Asp Tyr Ser Lys
            165                 170                 175

Tyr Thr His Asn Ser Val Lys Asn Ile Asn Val Thr Lys Glu Arg Phe
            180                 185                 190

Ile Ala Asn Asp Asp Leu Ile His Lys Leu Ile Glu Ser Ser Glu Ala
            195                 200                 205

Met Lys Gln Ser Ser Glu Arg Asp Lys Val Lys Ala Phe Val Gln Tyr
            210                 215                 220

Val Ala Asn His Thr Thr Tyr Asp Trp Glu Ala Ala Asn Lys Ala Val
225                 230                 235                 240

Gln Asn Tyr Ala Asp Ile Asn Tyr Tyr Leu Gly Ser Asp Leu Phe Ala
            245                 250                 255

Val Thr Glu Arg Gln Lys Ala Met Cys Val Gly Phe Ser Thr Thr Ala
            260                 265                 270

Ala Arg Ala Phe Asn Met Leu Gly Leu Pro Ala Tyr Val Val Val Gly
            275                 280                 285

Lys Asn Ala Glu Gly Val Pro His Ala Thr Ala Arg Val Tyr Tyr Asp
            290                 295                 300

Lys Lys Trp His Thr Ile Asp Gly Thr Gly Phe Ile Thr Gly Asn Lys
305                 310                 315                 320

His Gln Arg Ser Ala Lys Tyr Ser Glu Lys His Phe Ser Thr Ile Gly
            325                 330                 335

Glu Asp Ser Tyr Asp Val Val Glu Ala Gly Gln Glu Pro Lys Ala Glu
            340                 345                 350

Arg Asn Tyr Met Ile Ile Asp Ser Asn Tyr Glu Ser Trp Ala Met Lys
            355                 360                 365

Gln Lys Thr Ala Asp Leu Leu Leu Phe Asn Lys Glu Lys Ser Leu Val
            370                 375                 380

Gly Leu Asp Tyr Ile Ala Tyr Val Glu Pro Thr Tyr Ile Thr Glu Asn
385                 390                 395                 400

Lys Lys Asn His Leu Leu Asp Ile Tyr Lys Ala Leu Lys Arg Lys Val
            405                 410                 415

Glu Glu Thr Lys Ala Thr Asp Lys Asp Asp Lys Asp Lys Gln Glu
            420                 425                 430

<210> SEQ ID NO 12
<211> LENGTH: 23
<212> TYPE: DNA
<213> ORGANISM: Artificial Sequence
<220> FEATURE:
<223> OTHER INFORMATION: Primer/probe

<400> SEQUENCE: 12
tcactgcagt tttggggagt agg                                          23

```
<210> SEQ ID NO 13
<211> LENGTH: 22
<212> TYPE: DNA
<213> ORGANISM: Artificial Sequence
<220> FEATURE:
<223> OTHER INFORMATION: Primer/probe

<400> SEQUENCE: 13
atggatccca gttcagaacc tc                                                22

<210> SEQ ID NO 14
<211> LENGTH: 25
<212> TYPE: DNA
<213> ORGANISM: Artificial Sequence
<220> FEATURE:
<223> OTHER INFORMATION: Primer/probe

<400> SEQUENCE: 14
cgggatccag agaaaaaaga gatcc                                             25

<210> SEQ ID NO 15
<211> LENGTH: 23
<212> TYPE: DNA
<213> ORGANISM: Artificial Sequence
<220> FEATURE:
<223> OTHER INFORMATION: Primer/probe

<400> SEQUENCE: 15
aggaattcac cgttattgta gcg                                               23

<210> SEQ ID NO 16
<211> LENGTH: 19
<212> TYPE: DNA
<213> ORGANISM: Artificial Sequence
<220> FEATURE:
<223> OTHER INFORMATION: Primer/probe

<400> SEQUENCE: 16
attgtatttg gtggaggag                                                    19

<210> SEQ ID NO 17
<211> LENGTH: 21
<212> TYPE: DNA
<213> ORGANISM: Artificial Sequence
<220> FEATURE:
<223> OTHER INFORMATION: Primer/probe

<400> SEQUENCE: 17
tttagcagct aagttgatac c                                                 21

<210> SEQ ID NO 18
<211> LENGTH: 33
<212> TYPE: DNA
<213> ORGANISM: Artificial Sequence
<220> FEATURE:
<223> OTHER INFORMATION: Primer/probe

<400> SEQUENCE: 18
gtttccatgg atgaaaactc acatttacaa tcg                                    33

<210> SEQ ID NO 19
<211> LENGTH: 25
<212> TYPE: DNA
<213> ORGANISM: Artificial Sequence
<220> FEATURE:
<223> OTHER INFORMATION: Primer/probe
```

```
<400> SEQUENCE: 19
acgtgcggcc gcataagctt cgtac                                             25

<210> SEQ ID NO 20
<211> LENGTH: 35
<212> TYPE: DNA
<213> ORGANISM: Artificial Sequence
<220> FEATURE:
<223> OTHER INFORMATION: Primer/probe

<400> SEQUENCE: 20
aacgtcagaa agcgatgagt gtaggtttca gcact                                  35

<210> SEQ ID NO 21
<211> LENGTH: 30
<212> TYPE: DNA
<213> ORGANISM: Artificial Sequence
<220> FEATURE:
<223> OTHER INFORMATION: Primer/probe

<400> SEQUENCE: 21
cagaaggtgt cccggctgct acagcgcgtg                                        30

<210> SEQ ID NO 22
<211> LENGTH: 41
<212> TYPE: DNA
<213> ORGANISM: Artificial Sequence
<220> FEATURE:
<223> OTHER INFORMATION: Primer/probe

<400> SEQUENCE: 22
taaaaagtgg cacaccattg ccggtacagg ttttattaca g                           41

<210> SEQ ID NO 23
<211> LENGTH: 10
<212> TYPE: PRT
<213> ORGANISM: Artificial sequence
<220> FEATURE:
<223> OTHER INFORMATION: synthetic sequence

<400> SEQUENCE: 23

Pro Pro Pro Pro Pro Leu Arg Ser Gly Cys
1               5                   10
```

STREPTOCOCCAL PROTEASES

FIELD OF THE INVENTION

The invention relates to a new Streptococcal proteases which displays IgG degrading cysteine protease activity. The invention further relates to the treatment of and vaccination against streptococcal infections, the treatment of conditions mediated by pathogenic IgG antibodies, such as autoimmune diseases, and to the development of new tools for biotechnology.

BACKGROUND TO THE INVENTION

Pathogenic bacteria have evolved various strategies to colonize and invade their host and a wide variety of virulence factors are employed to promote growth and to mediate evasion from host immune responses. To avoid the obvious risk of extinction, pathogenic bacteria have to deal with both innate immune responses, but most importantly also with specific immunoglobulins. Specific Ig are central to the adaptive immune system by initiating the complement based and/or phagocyte based immune response. Ig consists of variable antigen-recognizing Fab regions that are linked through a flexible hinge region with the Fc effector part. The Fc region mediates contact with specific receptors on phagocytic cells or triggers the classical pathway of complement by binding C1q. Thus, the hinge region is target for several microbial proteases and examples include IdeS from *S. pyogenes* (von Pawel-Rammingen et al. 2002. *EMBO J.* 21, 1607-161), Gingipain K from *Porphymonas ginivalis* (Vincents et al. 2011. *FASEB J.* 10, 3741-3750) and SspA from *Staphylococcus aureus* (Prokesova et al. 1992. *Immunol. Lett.* 31, 259-265).

Streptococcal infection are common in humans, as well as domestic animal, like swine, horses and cattle. Streptococcal infections vary in severity from relatively mild diseases to serious life threatening conditions. The provision of streptococcal antigens that can be used in human and veterinary vaccines in the prophylaxis, prevention and treatment of streptococcal infections is greatly needed.

Proteases with strict sequence specificity are useful as biotechnological tools. Proteases that degrade immunoglobulins can have medical use, e.g. can proteases that specifically degrade IgG be used for treatment or prevention of diseases or conditions mediated by IgG antibodies.

SUMMARY OF THE INVENTION

The present inventors have identified, purified and characterised a novel family of IgG degrading enzymes from streptoccoci. This family of enzymes, designated IgdE for Immunoglobulin G-degrading Enzyme, are cysteine proteases distinct from previous characterized streptococcal immunoglobulin degrading proteases of the IdeS family and mediates efficient cleavage of the hinge region of IgG with a high degree of specificity.

The enzyme has been identified in strains of *S. suis*, designated $IgdE_{suis}$; in strains of *S. agalactiae*, designated $IgdE_{agalactiae}$; in strains *S. porcinus*, designated $IgdE_{porcinus}$; in strains of *S. equi*, designated $IgdE_{equi}$; and in strains of *S. pseudoporcinus*, designated $IgdE_{pseudoporcinus}$.

The IgdE from *S. suis* is demonstrated to be highly specific for porcine IgG. Similar to the IgM cleaving protease $Ide_{Ssuis}$, the 1121 amino acid large protein carries the proteolytic active domain in the N-terminal part of the protein. A full size protein is not essential for IgG cleavage in vitro, as a truncated *S. suis* IgdE protein consisting of the N-terminal 470 amino acids retains IgG cleavage activity.

Cleavage of porcine IgG by *S. suis* IgdE occurred just N-terminal of the hinge region cysteine residues that are likely to form covalent disulphide bonds between the two IgG heavy chains. Thus, IgG cleavage results in the formation of a 64 kDa Fc fragment and two Fab fragments. This cleavage pattern is distinct from the IgG endopeptidase IdeS of *S. pyogenes* that hydrolyses IgG in the lower hinge region, thereby generating one F(ab')$_2$ fragment and two identical ½Fc fragments (von Pawel-Rammingen ibid) and from $Ide_{Ssuis}$ that cleaves IgM C-terminal from the intra-chain disulphide bonds generating free ½Fc fragments (Seele et al. 2015. *J. Vet. Res.* 46, 45).

*S. suis* can e.g. cause meningitis in humans and swine. *S. agalactiae* can e.g. cause meningitis and sepsis in humans and cattle. *S. porcinus* can e.g. cause respiratory tract infections in swine, porcine strangles. *S. equi* can e.g. cause respiratory tract infections in horses, strangles.

Proteases of the IgdE family are of use in the prevention and treatment of Streptococcal infections, such as a vaccine for immunization against streptococcal infections. IgdE antibodies are further of use in passive immunization and treatment of conditions associated with streptococcal infections. IgdE proteases are also useful for developing new biotechnological tools, and for treating or preventing diseases or conditions mediated by IgG antibodies, such as autoimmune diseases, transplant rejection, post-operative treatment and acquired haemophilia.

Accordingly, in a first aspect the invention provides an isolated IgdE polypeptide for use in generating an immune response in a subject.

The isolated IgdE polypeptide is preferably an $IgdE_{suis}$, $IgdE_{agalactiae}$, $IgdE_{porcinus}$, $IgdE_{equi}$, or an $IgdE_{pseudoporcinus}$ polypeptide, or a variant or fragment of any thereof which retains cysteine protease activity and/or is capable of generating an immune response to a *streptococcus* in a subject. The variant may be an IgdE polypeptide from another bacterium. The bacterium is preferably a *Streptococcus*.

In one embodiment of the first aspect the invention provides an IgdE polypeptide for use in generating an immune response in a subject comprising:

(a) the amino acid sequence of SEQ ID NO: 1;

(b) a variant of SEQ ID NO: 1 having at least 70% identity to the amino acid sequence of SEQ ID NO: 1 and having IgG degrading cysteine protease activity;

(c) a fragment of SEQ ID NO: 1, a variant of SEQ ID NO:1, or a fragment of a variant of SEQ ID NO: 1 which is capable of generating an immune response to a *streptococcus*, preferably a *S. suis* in a subject;

(d) the amino acid sequence of SEQ ID NO: 3;

(e) a variant of SEQ ID NO: 3 having at least 70% identity to the amino acid sequence of SEQ ID NO: 3 and having IgG degrading cysteine protease activity;

(f) a fragment of SEQ ID NO: 3, a variant of SEQ ID NO:3, or a fragment of a variant of SEQ ID NO: 3 which is capable of generating an immune response to a *streptococcus*, preferably a *S. agalactiae* in a subject;

(g) the amino acid sequence of SEQ ID NO: 5;

(h) a variant of SEQ ID NO: 5 having at least 70% identity to the amino acid sequence of SEQ ID NO: 5 and having IgG degrading cysteine protease activity;

(i) a fragment of SEQ ID NO: 5, a variant of SEQ ID NO:5, or a fragment of a variant of SEQ ID NO: 5 which is capable of generating an immune response to a *S. porcinus* in a subject;

(j) the amino acid sequence of SEQ ID NO: 7;

(k) a variant of SEQ ID NO: 7 having at least 70% identity to the amino acid sequence of SEQ ID NO: 7 and having IgG degrading cysteine protease activity;

(l) a fragment of SEQ ID NO: 7, a variant of SEQ ID NO:7, or a fragment of a variant of SEQ ID NO: 7 which is capable of generating an immune response to a *streptococcus*, preferably a *S. equi* in a subject; or (m) the amino acid sequence of SEQ ID NO: 9;

(n) a variant of SEQ ID NO: 9 having at least 70% identity to the amino acid sequence of SEQ ID NO: 9 and having IgG degrading cysteine protease activity;

(o) a fragment of SEQ ID NO: 9, a variant of SEQ ID NO:9, or a fragment of a variant of SEQ ID NO: 9 which is capable of generating an immune response to a *streptococcus*, preferably a *S. pseudoporcinus* in a subject;

Preferably the immune response is a protective immune response.

Preferably the immune response generates antibodies able to neutralize the IgG degrading cysteine protease activity of the IgdE of an infectious *streptococcus* in the immunized subject.

In another embodiment of the first aspect the invention provides a method for generating an immune response in a subject comprising administering an IgdE polypeptide to said subject.

In a second aspect the invention provides an isolated polynucleotide encoding an IgdE polypeptide for use in generating an immune response in a subject.

The IgdE polypeptide is preferably an IgdE$_{suis}$, IgdE$_{agalactiae}$, IgdE$_{porcinus}$, IgdE$_{equi}$ or an IgdE$_{pseudoporcinus}$ polypeptide, or a variant or fragment of any thereof which retains cysteine protease activity and/or is capable of generating an immune response to a *streptococcus* in a subject. The variant may be an IgdE polypeptide from another bacterium. The bacterium is preferably a *Streptococcus*.

In one embodiment of the second aspect the invention provides a polynucleotide encoding an IgdE polypeptide for use in generating an immune response in a subject comprising:

(a) a sequence which encodes the polypeptide SEQ ID NO:1 or a variant or a fragment thereof as defined above;

(b) a sequence which encodes the polypeptide SEQ ID NO:3 or a variant or a fragment thereof as defined above;

(c) a sequence which encodes the polypeptide SEQ ID NO:5 or a variant or a fragment thereof as defined above;

(d) a sequence which encodes the polypeptide SEQ ID NO:7 or a variant or a fragment thereof as defined above; or (e) a sequence which encodes the polypeptide SEQ ID NO:9 or a variant or a fragment thereof as defined above.

In another embodiment of the second aspect the invention provides a polynucleotide encoding an IgdE polypeptide for use in generating an immune response in a subject comprising:

(a) SEQ ID NO: 2 or a complementary sequence thereto;

(b) a sequence which is degenerate as a result of the genetic code to a sequence as defined in (a);

(c) a sequence which hybridises under stringent conditions to the sequence defined in (a) or (b);

(d) a sequence having at least 70% identity to a sequence as defined in (a) or (b);

(e) a fragments of any of the sequences (a), (b), (c) or (d), and which encodes a polypeptide having IgdE cysteine protease activity and/or is capable of generating an immune response against a *streptococcus*, preferably *S. suis* in a subject.

(f) SEQ ID NO: 4 or a complementary sequence thereto;

(g) a sequence which is degenerate as a result of the genetic code to a sequence as defined in (f);

(h) a sequence which hybridises under stringent conditions to the sequence defined in (f) or (g);

(i) a sequence having at least 70% identity to a sequence as defined in (f) or (g);

(j) a fragments of any of the sequences (f), (g), (h) or (i), and which encodes a polypeptide having IgG degrading cysteine protease activity and/or is capable of generating an immune response against a *streptococcus*, preferably *S. agalactiae* in a subject;

(k) SEQ ID NO: 6 or a complementary sequence thereto;

(l) a sequence which is degenerate as a result of the genetic code to a sequence as defined in (k);

(m) a sequence which hybridises under stringent conditions to the sequence defined in (k) or (l);

(n) a sequence having at least 70% identity to a sequence as defined in (k) or (l);

(o) a fragments of any of the sequences (k), (l), (m) or (n), and which encodes a polypeptide having IgG degrading cysteine protease activity and/or is capable of generating an immune response against a *streptococcus*, preferably *S. porcinus* in a subject;

(p) SEQ ID NO: 8 or a complementary sequence thereto;

(q) a sequence which is degenerate as a result of the genetic code to a sequence as defined in (p);

(r) a sequence which hybridises under stringent conditions to the sequence defined in (p) or (q);

(s) a sequence having at least 70% identity to a sequence as defined in (p) or (q); or (t) a fragments of any of the sequences (p), (q), (r) or (s), and which encodes a polypeptide having IgG degrading cysteine protease activity and/or is capable of generating an immune response against a *streptococcus*, preferably *S. equi* in a subject;

(u) SEQ ID NO: 10 or a complementary sequence thereto;

(v) a sequence which is degenerate as a result of the genetic code to a sequence as defined in (u);

(w) a sequence which hybridises under stringent conditions to the sequence defined in (u) or (v);

(x) a sequence having at least 70% identity to a sequence as defined in (u) or (v); or (y) a fragments of any of the sequences (u), (v), (w) or (x), and which encodes a polypeptide having IgG degrading cysteine protease activity and/or is capable of generating an immune response against a *streptococcus*, preferably *S. pseudoporcinus* in a subject.

Preferably the immune response is a protective immune response.

Preferably the immune response generates antibodies able to neutralize the IgG degrading cysteine protease activity of the IgdE of an infectious *streptococcus* in the immunized subject.

In another embodiment of the second aspect the invention provides a method for generating an immune response in a subject comprising administering a polynucleotide encoding an IgdE polypeptide to said subject.

In a third aspect the present invention provides an isolated IgdE polypeptide for use in treatment or prevention of a disease or condition mediated by IgG antibodies.

The IgdE polypeptide is preferably an IgdE$_{suis}$, IgdE$_{agalactiae}$, IgdE$_{porcinus}$, IgdE$_{equi}$ or an IgdE$_{pseudoporcinus}$ polypeptide, or a variant or fragment of any thereof which retains cysteine protease activity. The variant may be an IgdE polypeptide from another bacterium. The bacterium is preferably a *Streptococcus*.

In one embodiment of the third aspect the invention provides an IgdE polypeptide for use in treatment or prevention of a disease or condition mediated by IgG antibodies comprising:

(a) the amino acid sequence of SEQ ID NO: 1;
(b) a variant of SEQ ID NO: 1 having at least 70% identity to the amino acid sequence of SEQ ID NO: 1 and having IgG degrading cysteine protease activity;
(c) a fragment of SEQ ID NO: 1 or a fragment of a variant of SEQ ID NO: 1 having IgG degrading cysteine protease activity;
(d) the amino acid sequence of SEQ ID NO: 3;
(e) a variant of SEQ ID NO: 3 having at least 70% identity to the amino acid sequence of SEQ ID NO: 3 and having IgG degrading cysteine protease activity;
(f) a fragment of SEQ ID NO: 3 or a fragment of a variant of SEQ ID NO: 3 having IgG degrading cysteine protease activity;
(g) the amino acid sequence of SEQ ID NO: 5;
(h) a variant of SEQ ID NO: 5 having at least 70% identity to the amino acid sequence of SEQ ID NO: 5 and having IgG degrading cysteine protease activity;
(i) a fragment of SEQ ID NO: 5 or a fragment of a variant of SEQ ID NO: 5 having IgG degrading cysteine protease activity;
(j) the amino acid sequence of SEQ ID NO: 7;
(k) a variant of SEQ ID NO: 7 having at least 70% identity to the amino acid sequence of SEQ ID NO: 7 and having IgG degrading cysteine protease activity;
(l) a fragment of SEQ ID NO: 7 or a fragment of a variant of SEQ ID NO: 7 having IgG degrading cysteine protease activity;
(m) the amino acid sequence of SEQ ID NO: 9;
(n) a variant of SEQ ID NO: 9 having at least 70% identity to the amino acid sequence of SEQ ID NO: 9 and having IgG degrading cysteine protease activity;
(o) a fragment of SEQ ID NO: 9 or a fragment of a variant of SEQ ID NO: 9 having IgG degrading cysteine protease activity;
(p) the amino acid sequence of SEQ ID NO: 11;
(q) a variant of SEQ ID NO: 11 having at least 70% identity to the amino acid sequence of SEQ ID NO: 11 and having IgG degrading cysteine protease activity; or
(r) a fragment of SEQ ID NO: 11 or a fragment of a variant of SEQ ID NO: 11 having IgG degrading cysteine protease activity.

Preferably the IgdE polypeptide can be an IgdE$_{agalactiae}$ polypeptide comprising:

(d) the amino acid sequence of SEQ ID NO: 3;
(e) a variant of SEQ ID NO: 3 having at least 70% identity to the amino acid sequence of SEQ ID NO: 3 and having IgG degrading cysteine protease activity;
(f) a fragment of SEQ ID NO: 3 or a fragment of a variant of SEQ ID NO: 3 having IgG degrading cysteine protease activity;

In another embodiment of the third aspect the invention provides a method for treatment, prophylaxis or prevention of a disease or condition mediated by IgG antibodies comprising administering a therapeutically effective amount of an IgdE polypeptide to a subject.

The disease or condition mediated by IgG antibodies, can be an autoimmune diseases, transplant rejection, post-operative treatment and acquired haemophilia.

In a fourth aspect the present invention provides an in vitro method for the cleavage of IgG, comprising contacting IgG with an IgdE polypeptide having cysteine protease activity.

The IgdE polypeptide is preferably an IgdE$_{suis}$, IgdE$_{agalactiae}$, IgdE$_{porcinus}$, IgdE$_{equi}$, or an IgdE$_{pseudoporcinus}$ polypeptide, or a variant or fragment of any thereof which retains IgG degrading cysteine protease activity. The variant may be an IgdE polypeptide from another bacterium. The bacterium is preferably a *Streptococcus*.

In one embodiment of the fourth aspect the present invention provides an in vitro method for the cleavage of IgG, comprising contacting IgG with an IgdE polypeptide comprising:

(a) the amino acid sequence of SEQ ID NO: 1;
(b) a variant of SEQ ID NO: 1 having at least 70% identity to the amino acid sequence of SEQ ID NO: 1 and having IgG degrading cysteine protease activity;
(c) a fragment of SEQ ID NO: 1 or a fragment of a variant of SEQ ID NO: 1 having IgG degrading cysteine protease activity.
(d) the amino acid sequence of SEQ ID NO: 3;
(e) a variant of SEQ ID NO: 3 having at least 70% identity to the amino acid sequence of SEQ ID NO: 3 and having IgG degrading cysteine protease activity;
(f) a fragment of SEQ ID NO: 3 or a fragment of a variant of SEQ ID NO: 3 having IgG degrading cysteine protease activity;
(g) the amino acid sequence of SEQ ID NO: 5;
(h) a variant of SEQ ID NO: 5 having at least 70% identity to the amino acid sequence of SEQ ID NO: 5 and having IgG degrading cysteine protease activity;
(i) a fragment of SEQ ID NO: 5 or a fragment of a variant of SEQ ID NO: 5 having IgG degrading cysteine protease activity;
(j) the amino acid sequence of SEQ ID NO: 7;
(k) a variant of SEQ ID NO: 7 having at least 70% identity to the amino acid sequence of SEQ ID NO: 7 and having IgG degrading cysteine protease activity;
(l) a fragment of SEQ ID NO: 7 or a fragment of a variant of SEQ ID NO: 7 having IgG degrading cysteine protease activity;
(m) the amino acid sequence of SEQ ID NO: 9;
(n) a variant of SEQ ID NO: 9 having at least 70% identity to the amino acid sequence of SEQ ID NO: 9 and having IgG degrading cysteine protease activity;
(o) a fragment of SEQ ID NO: 9 or a fragment of a variant of SEQ ID NO: 9 having IgG degrading cysteine protease activity;
(p) the amino acid sequence of SEQ ID NO: 11;
(q) a variant of SEQ ID NO: 11 having at least 70% identity to the amino acid sequence of SEQ ID NO: 11 and having IgG degrading cysteine protease activity; or
(r) a fragment of SEQ ID NO: 11 or a fragment of a variant of SEQ ID NO: 11 having IgG degrading cysteine protease activity.

Preferably the IgdE polypeptide can be an IgdE$_{agalac}$ polypeptide comprising:

(d) the amino acid sequence of SEQ ID NO: 3;
(e) a variant of SEQ ID NO: 3 having at least 70% identity to the amino acid sequence of SEQ ID NO: 3 and having IgG degrading cysteine protease activity; or
(f) a fragment of SEQ ID NO: 3 or a fragment of a variant of SEQ ID NO: 3 having IgG degrading cysteine protease activity.

In another embodiment of the fourth aspect the present invention provides an in vitro method for the generation of Fc or Fab fragments of IgG, comprising contacting IgG with an IgdE polypeptide having IgG degrading cysteine protease activity.

In a fifth aspect the present invention provides a method for identifying a substance that activates or inhibits the IgG cysteine activity of an IgdE polypeptide. The method can comprise;

a) contacting the IgdE polypeptide and IgG with a candidate substance under conditions permitting IgG cysteine activity in the absence of the substance, b) determining the amount of IgG digested in the presence of the candidate substance compared to in the absence of the said substance, c) thereby determining whether the substance activates or inhibits the IgG cysteine activity of the IgdE polypeptide.

Quantitative analysis of IgG degradation can be performed as set out in Example 1.

Candidate compounds which may be tested in the methods according to the invention include simple organic molecules, commonly known as "small molecules", for example those having a molecular weight of less than 2000 Daltons. The method may also be used to screen compound libraries such as peptide libraries, including synthetic peptide libraries and peptide phage libraries. Other suitable molecules include polynucleotide sequences and any other molecules which modulate the IgG degrading activity of IgdE.

(A) Concentrated (20×) culture supernatants of S. suis strains 10 and 10$\Delta$ide$_{Ssuis}$ were incubated with 2% porcine plasma for 16 h at 37° C. and analyzed by SDS-PAGE under reducing conditions. A degradation product (*) of approximately 32 kDa was observed. (B) Anti-IgG Western Blot analysis of culture supernatant of S. suis strain 10 fractionated by ammonium sulfate precipitation. IgG degradation products (*) were obtained after incubation of 1% porcine plasma with 20-40% and 40-60% ammonium sulfate saturation fractions for 16 h at 37° C. Lane 1 showing the protein size standard is a photographic image of the membrane before detection of the chemiluminescence signal. (C) Culture supernatants of S. suis strains of all tested serotypes cleaved IgG. Concentrated (10×) culture supernatants were incubated with 1% porcine plasma for 16 h at 37° C. and analyzed by anti-IgG Western blot. IgG cleavage products (*) at approximately 32 kDa of varying intensity were observed in all lanes. Images of different western blots have been assembled into one figure.

Figure 2:
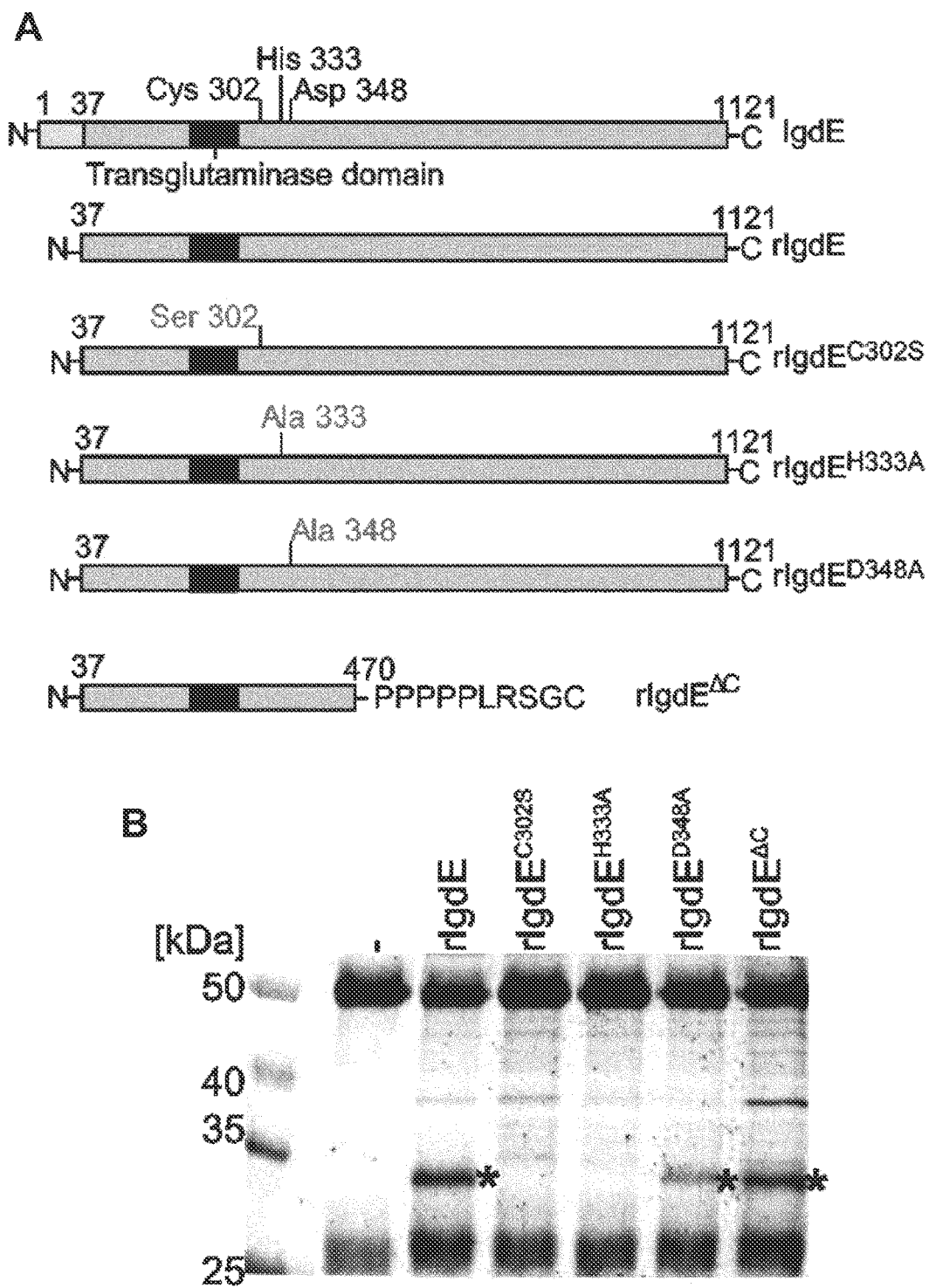

FIG. 2. Identification of the active site of S. suis IgdE.

(A) Schematic illustration of IgdE and the different rIgdE constructs with potential active site residues substitutions and the C-terminal truncation variant. The secretion signal peptide (residues 1-37) is marked in light grey, the transglutaminase domain is boxed and the potential active site residues and substitutions are indicated. (B) 3.3 µM porcine IgG was incubated for 16 h at 37° C. with soluble fractions of E. coli cells expressing different rIgdE constructs. The reaction was analyzed SDS-PAGE under reducing conditions. IgG cleavage (*) occurred upon incubation with rIgdE, rIgdE$^{D348A}$ and rIgdE$^{\Delta C}$ but not with rIgdE$^{C302S}$ or rIgdE$^{H333A}$. The weak protein band of 37 kDa is a contaminant present in lysate preparation and not related to IgdE activity.

Figure 3:
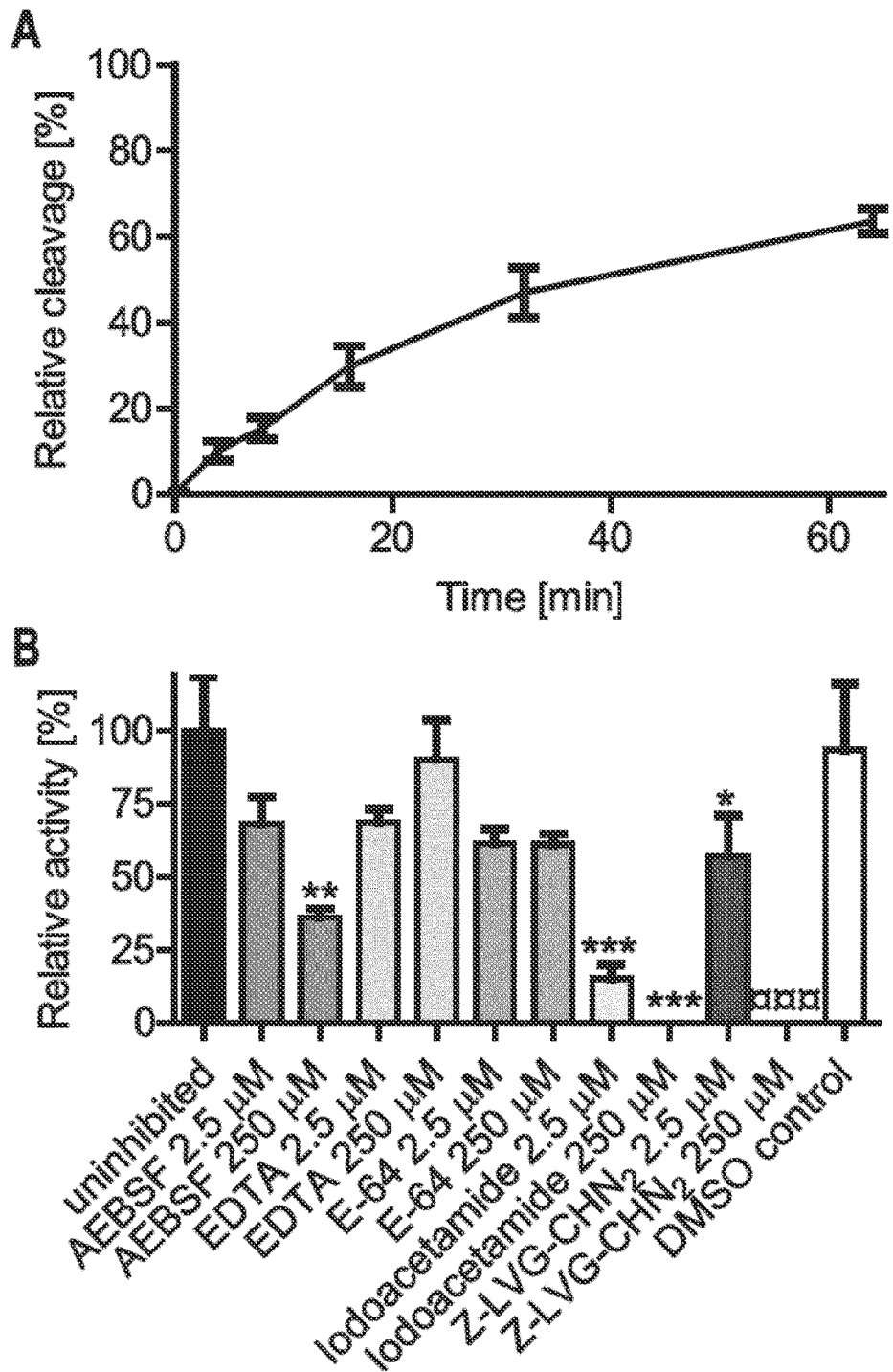

FIG. 3. Time course and inhibitor profile of recombinant S. suis IgdE.

The time course of cleavage (A) was monitored by continuous sampling prior to Coomassie fluor orange stained SDS-PAGE under reducing conditions followed by densitometric quantification of the cleavage product. 1.67 µM porcine IgG was incubated with 0.2 µM purified rIgdE$^{ac}$. Overnight cleavage (16 h) was set as 100% relative cleavage. For the inhibitor profile (B) initial cleavage in presence of 250 µM and 2.5 µM of each inhibitor was monitored. Initial cleavage activity of the uninhibited control was set as 100% relative activity. The DMSO control correlates to 250 µM Z-LVG-CHN2. Data are presented as mean±SEM of three experiments. Differences to the uninhibited control (*) or DMSO control (□) were analyzed by Dunnett's Multiple Comparison Test with significance set at P values of <0.05 (*), <0.01() and <0.001(* or □□□).

Figure 4:
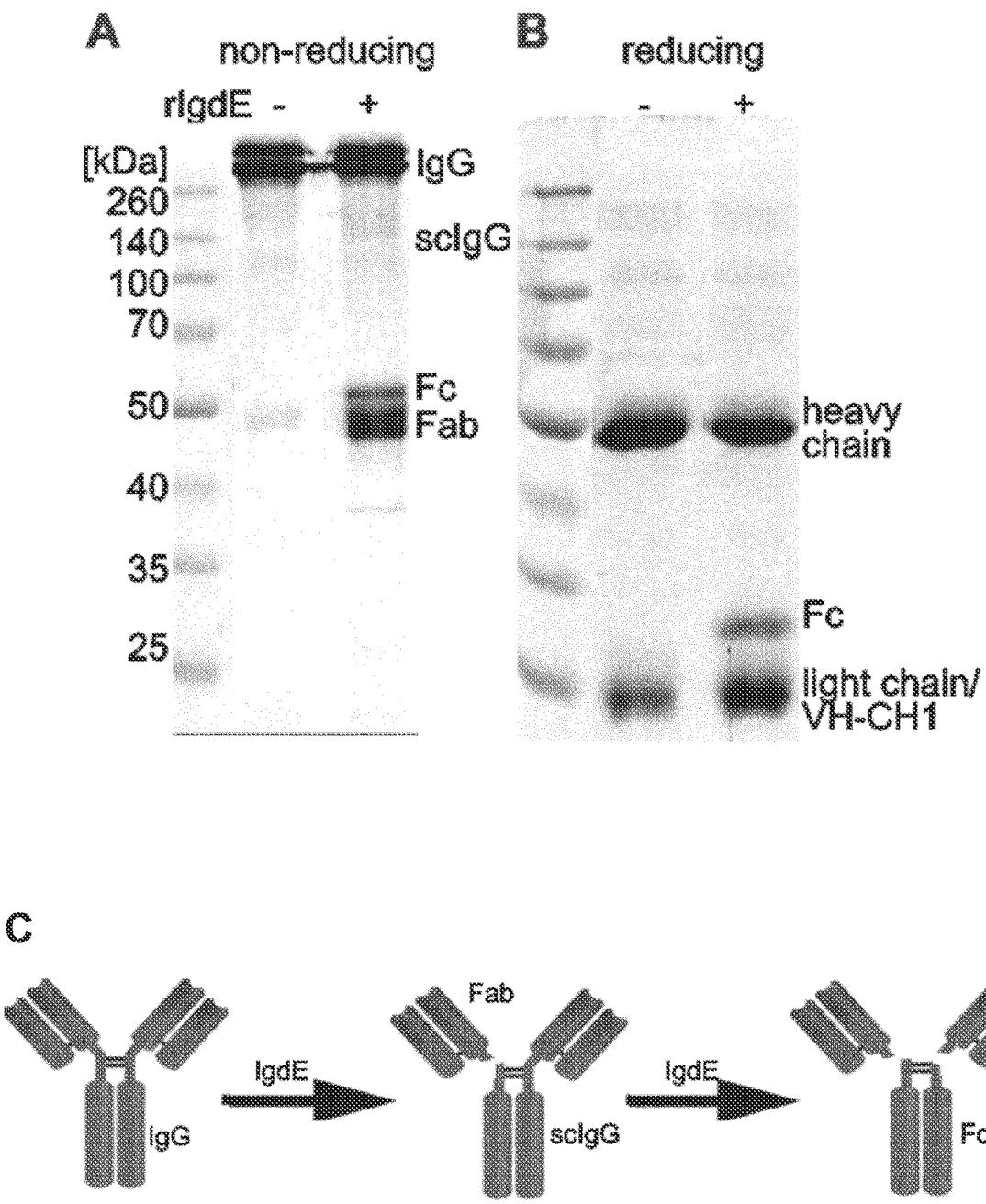

FIG. 4. S. suis IgdE cleaves the heavy chain of porcine IgG in the hinge region.

The reaction was analyzed by non-reducing (A) and reducing (B) Coomassie blue stained SDS-PAGE. 3.3 µM IgG was incubated with (+) or without (−) 10 nM purified rIgdE for 16 h at 37° C. (C) The observed cleavage pattern and cleavage site proposes a model where one IgG heavy chain is first hydrolyzed by IgdE resulting in one free Fab fragment (Fab) and single cleaved IgG (scIgG) and in a second step the other heavy chain is hydrolyzed resulting in one Fc fragment (Fc) and two Fab fragments.

Figure 5:
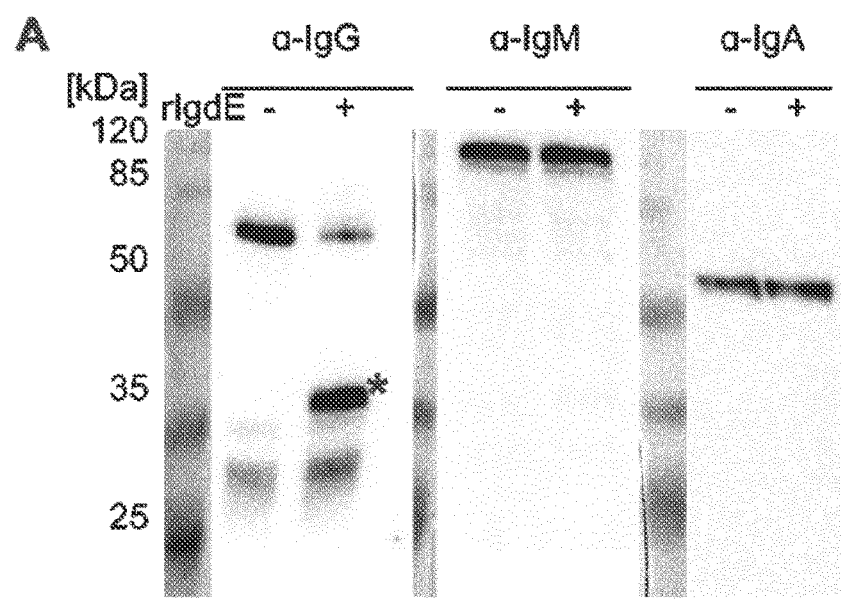
Figure 5:
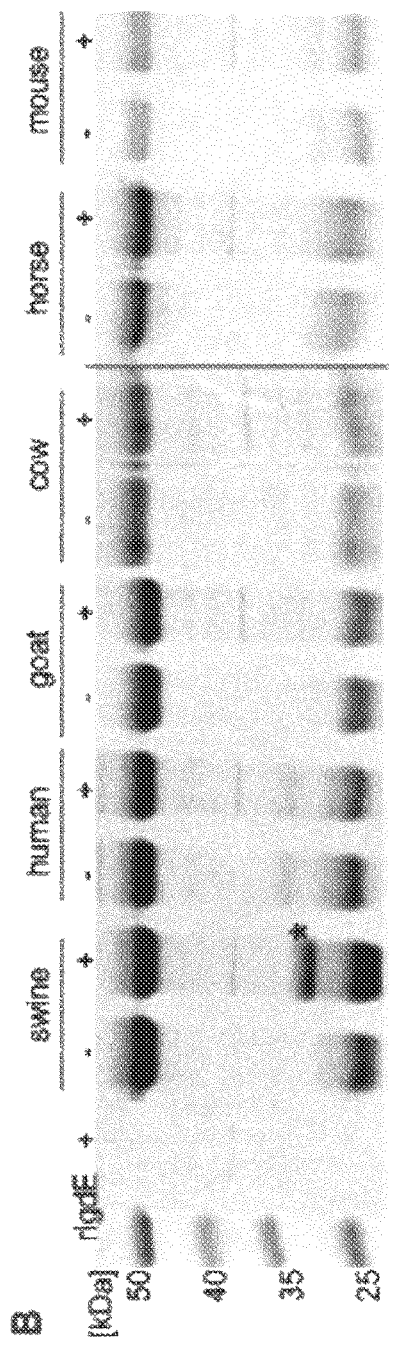

FIG. 5. IgdE is highly specific for porcine IgG.

(A) 2% porcine plasma was incubated with (+) or without (−) 10 nM purified rIgdE.

The reaction was analyzed by anti-porcine IgG, IgM and IgA Western blots under reducing conditions. Only cleavage of IgG was observed (*). (B) 0.5 mg/ml IgG of different species was incubated with (+) or without (−) 10 nM purified rIgdE and analyzed by SDS-PAGE under reducing conditions. No cleavage of IgG derived from any other species than pig (*) was observed. The weak protein band of 37 kDa is a contaminant present in lysate preparation (see lane 2) and not related to IgdE activity. Images of different gels have been assembled into one figure.

Figure 6:
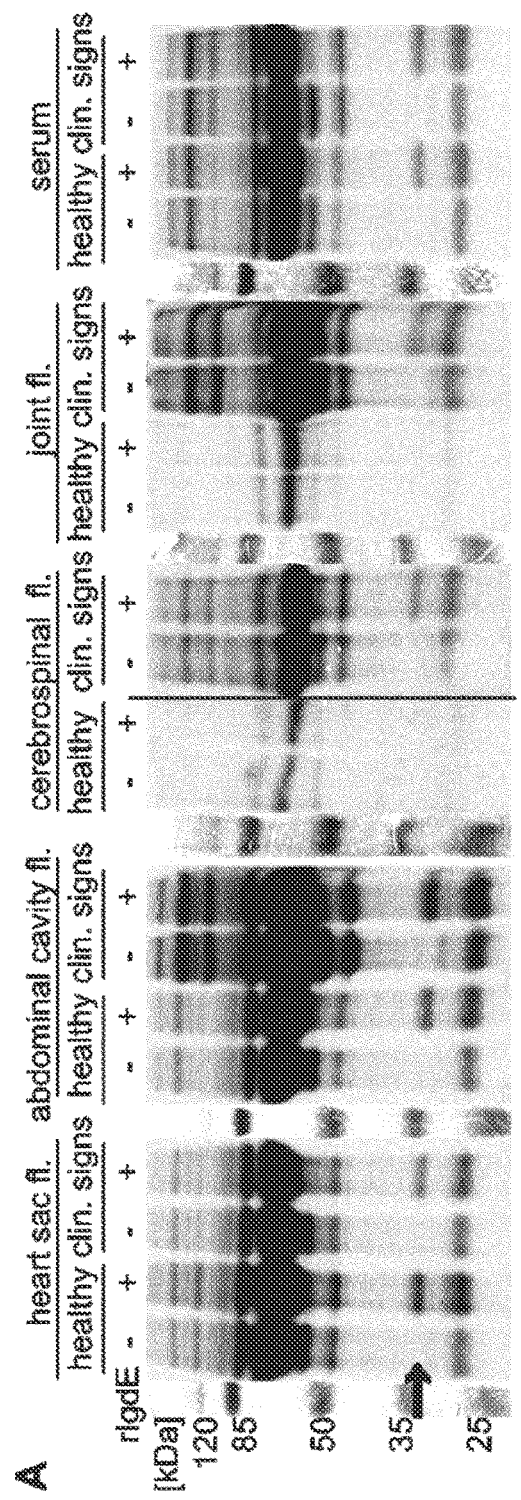
Figure 6:
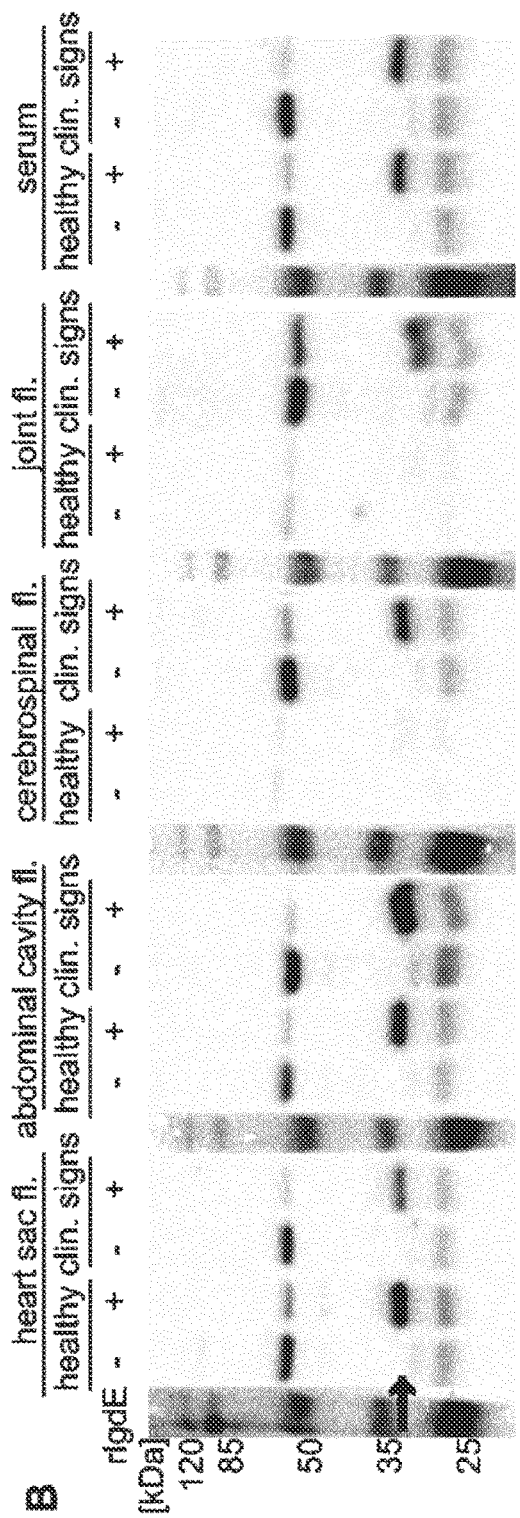

FIG. 6. S. suis IgdE degradation of endogenous IgG

S. suis IgdE degrades endogenous IgG in all tested body fluids of healthy pigs and pigs with respective lesions. (size indicated with arrows). No other degradations products could be observed. Body fluids were incubated with (+) or without (−) 10 nM purified rIgdE for 16 h at 37° C. The reactions were analyzed by SDS-PAGE (A) and anti-IgG Western blots (B) under reducing conditions. Lanes showing the protein size standard are a photographic image of the membrane before detection of the chemiluminescence signal. Images of different gels have been assembled into one figure.

Figure 7:
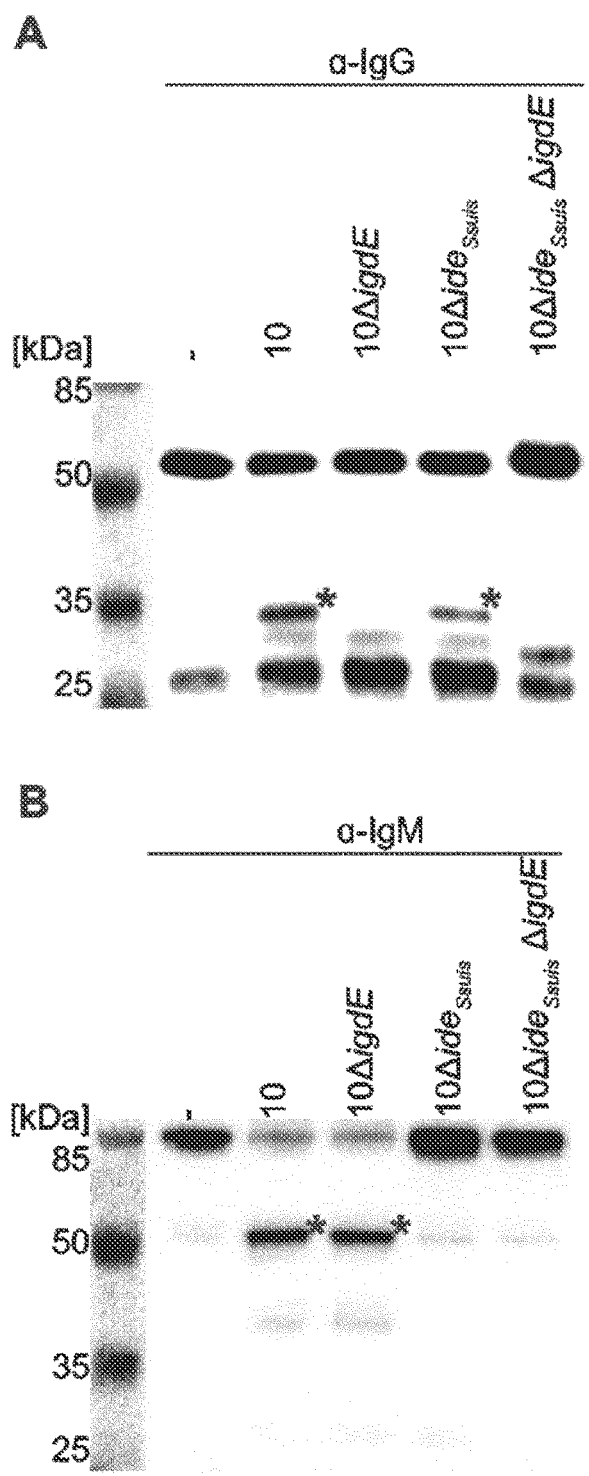

FIG. 7. IgdE is necessary for IgG cleavage by S. suis and IgG cleavage is independent of Ide$_{Ssuis}$.

Concentrated (10×) supernatants of S. suis strains 10, 10$\Delta$igdE, 10$\Delta$ide$_{Ssuis}$ and 10$\Delta$ide$_{Ssuis}$ $\Delta$igdE were incubated with 1% porcine plasma for 16 h at 37° C. The reaction was analyzed by anti-IgG Western blot (A) or anti-IgM Western blot (B) under reducing conditions. IgG degradation (*) was only observed when incubated with supernatants of strains 10 and 10$\Delta$ide$_{Ssuis}$, meanwhile IgM degradation (*) only was observed upon incubation with supernatants of strains 10 and 10$\Delta$igdE.

Figure 8:
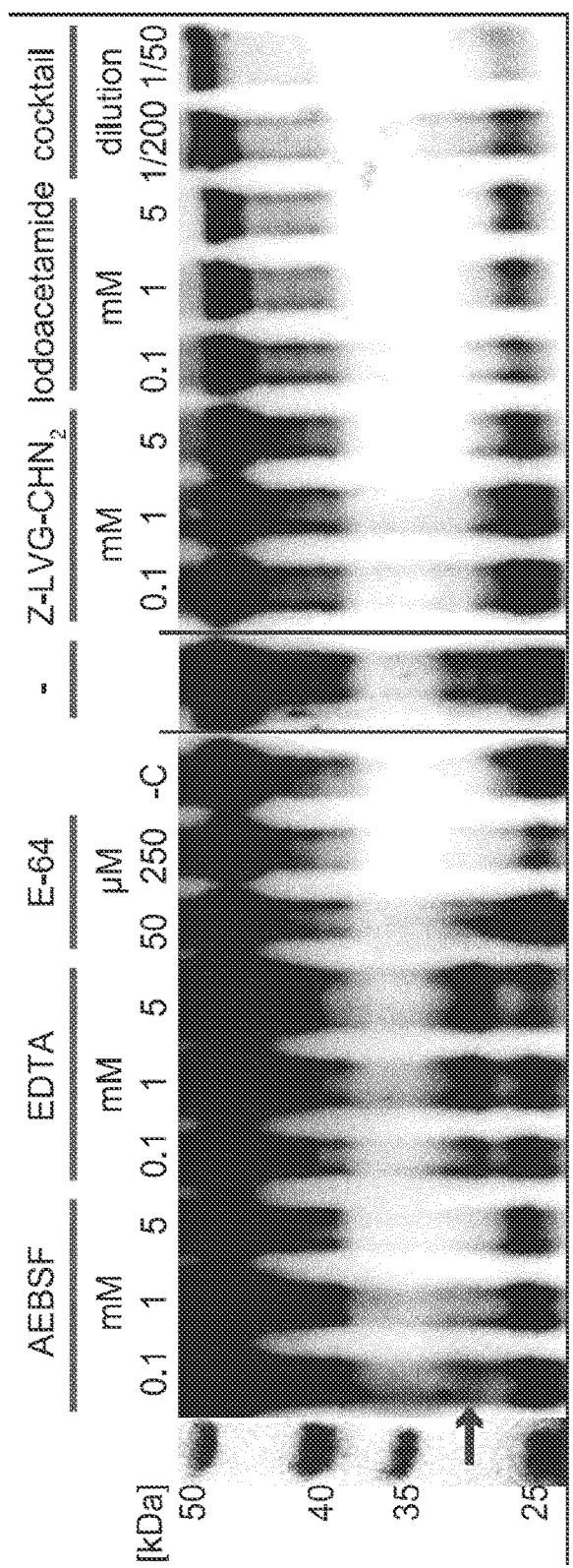

FIG. 8. Inhibitor profile of IgG degradation activity detected in culture supernatants of S. suis.

Concentrated (10×) culture supernatant of S. suis strain 10 was incubated with porcine plasma in presence of class specific protease inhibitors. The reaction was analyzed by anti-IgG western blot under reducing conditions. A cleavage product of IgG can be observed when incubated with 0.1-1 mM AEBSF, 0.1-5 mM EDTA, 50 µM E-64, without any inhibitor and 1/200 diluted complete inhibitor cocktail (marked with an asterisk), meanwhile no degradation product was observed when incubated with 5 mM AEBSF, 250 µM E-64, without concentrated supernatant (-C), 0.1-5 mM Z-LVG-CHN2, 0.1-5 mM iodoacetamide and 1/50 diluted complete inhibitor cocktail.

Figure 9:
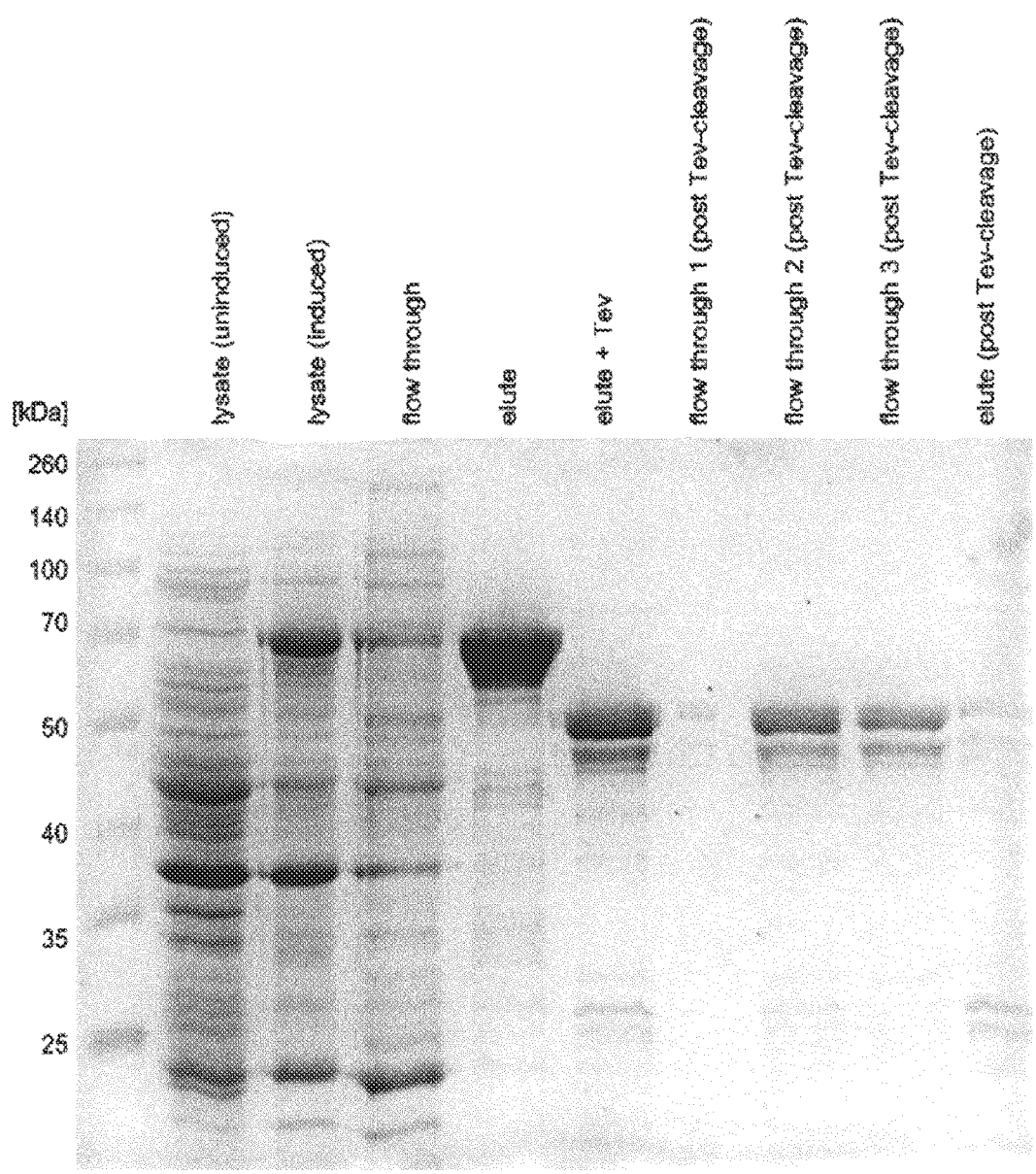

FIG. 9. Representative Coomassie blue stained SDS-PAGE gel monitoring rIgdE$^{\Delta C}$ purification.

rIgdE$^{\Delta C}$ was purified from lysate of IPTG induced *E. coli* carrying an expression plasmid. The elute of a Ni$^{2+}$-affinity chromatography purification containing His-ZZ-tagged rIgdEΔC was incubated with Tev-protease to remove the His-ZZ-tag prior to a second round of Ni$^{2+}$-affinity chromatography purification. The flow through fractions 2 and 3 of this purification step containing untagged rIgdE$^{\Delta C}$ were pooled, buffer ex-changed to PBS and used for further experiments. Two major bands around 50 kDa can be observed in these fractions, due to partial degradation of rIgdE$^{\Delta C}$.

Figure 10:
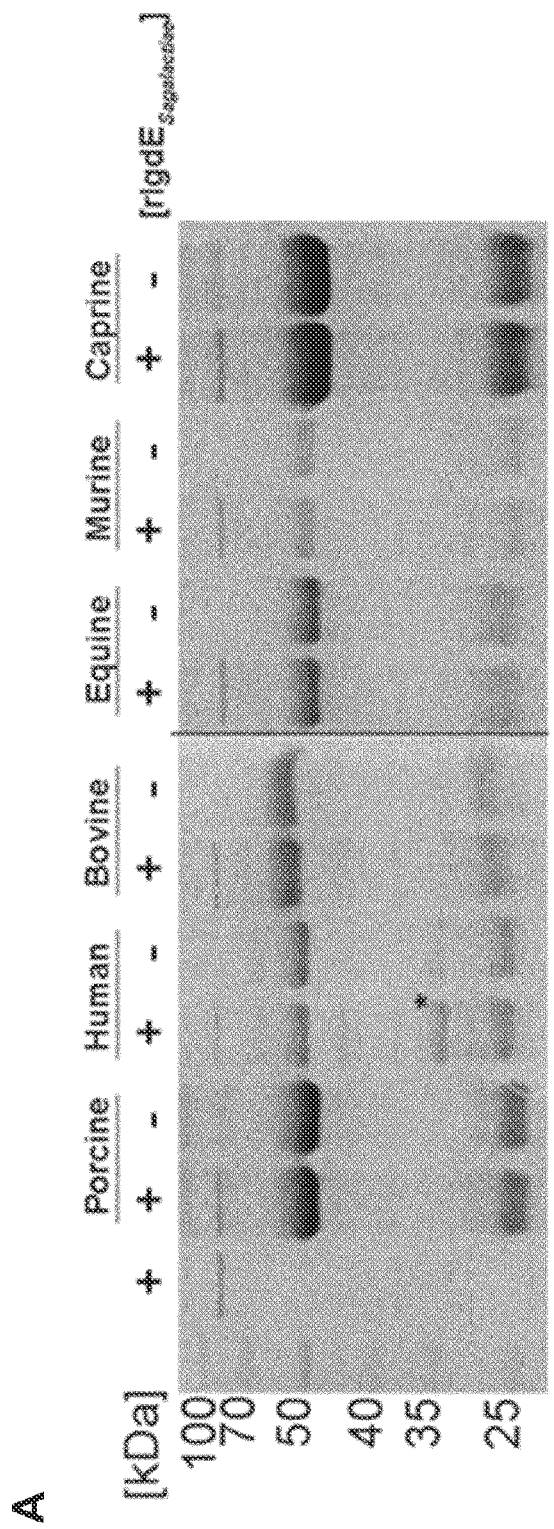
Figure 10:
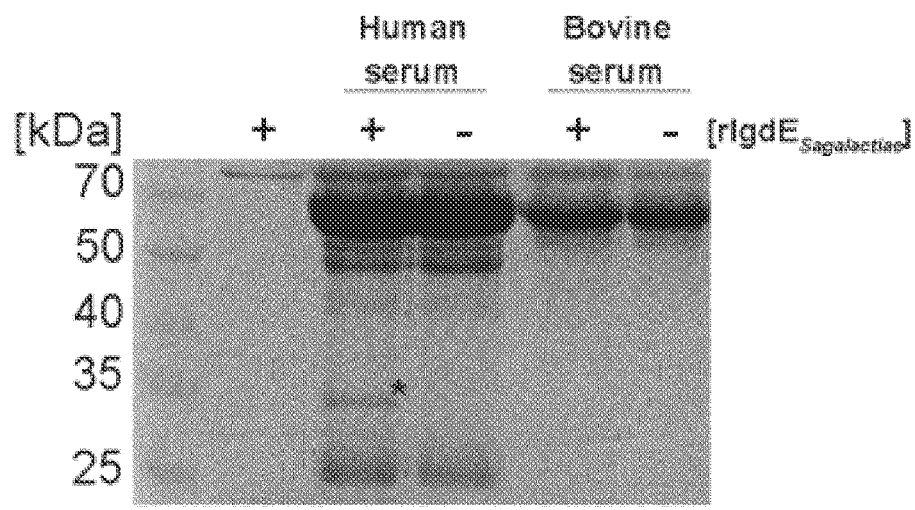
Figure 10:
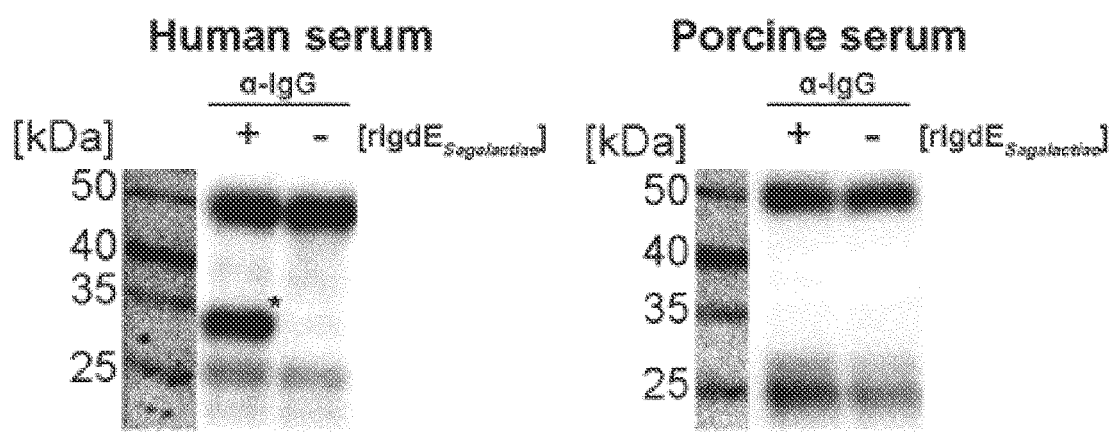
Figure 10:
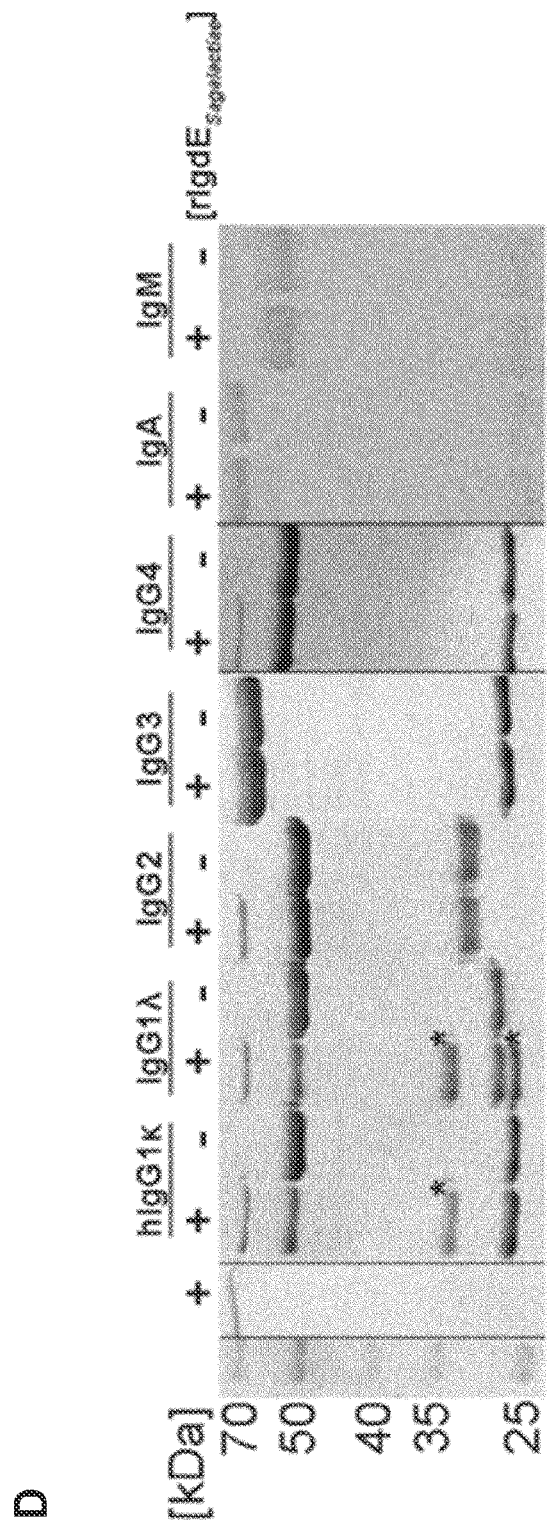

FIG. 10. rIgdEagalactiae specifically cleaves human IgG1.

(A) rIgdE$_{agalactiae}$ was incubated with polyclonal IgG of six different species for 18 h at 37° C. and analyzed by SDS-PAGE under reducing conditions. Degradation products are indicated by asterisks (*). Images of different gels have been used to create the figure. (B) rIgdE$_{agalactiae}$ was incubated with human or bovine serum for 18 h in 37° C. and analyzed by SDS-PAGE under reducing conditions. Degradation products are indicated by asterisks (*). (C) Western Blot with crude extracts of rIgdE$_{agalactiae}$ incubated with human and porcine serum for 18 h in 37° C. Membrane was treated with antibodies against human and porcine polyclonal IgG respectively. Degradation products are indicated by asterisks (*). (D) rIgdE$_{agalactiae}$ was incubated with subclasses of human IgG as well as human IgA and IgM for 18 h in 37° C. and analyzed by SDS-PAGE under reducing conditions. Degradation products are indicated by asterisks (*). Images of different gels have been used to create the figure.

Figure 11:
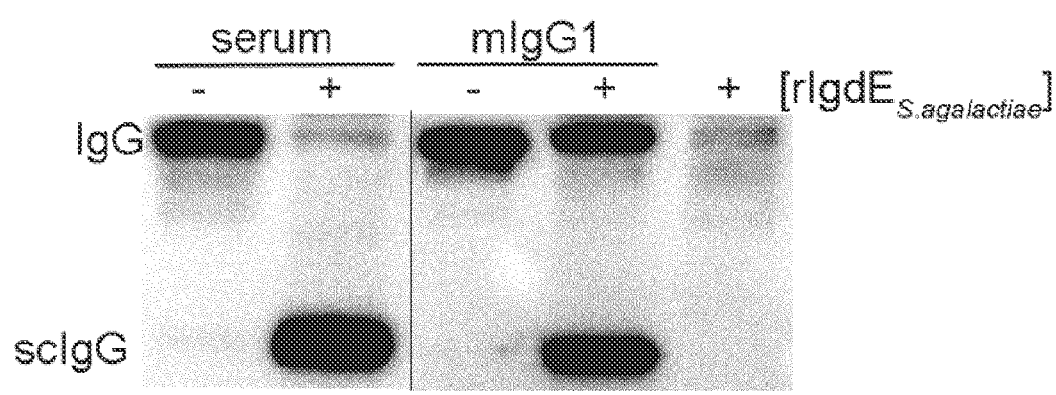

FIG. 11. rIgdEagalactiae degrades human serum IgG1 completely to single cleaved IgG1.

Human serum and monoclonal human IgG1 were incubated in presence (+) or absence (−) of rIgdE$_{agalactiae}$ for 18 h at 37° C. and analyzed by Western blot under non-reducing conditions with a human IgG-specific antibody.

Figure 12:
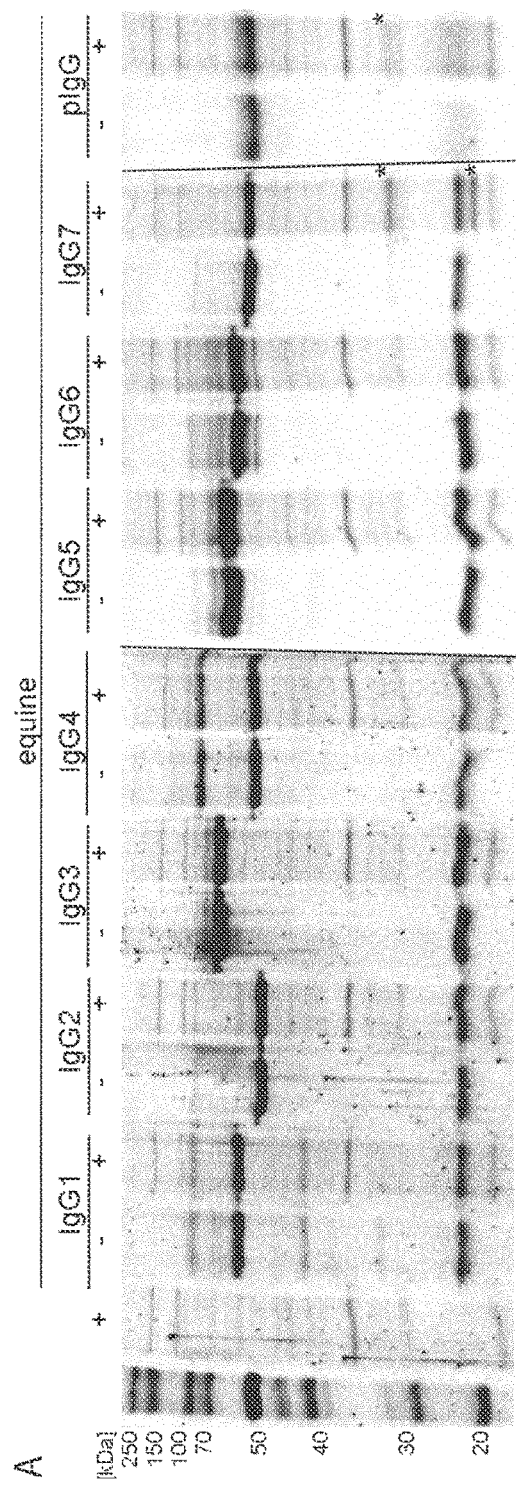
Figure 12:
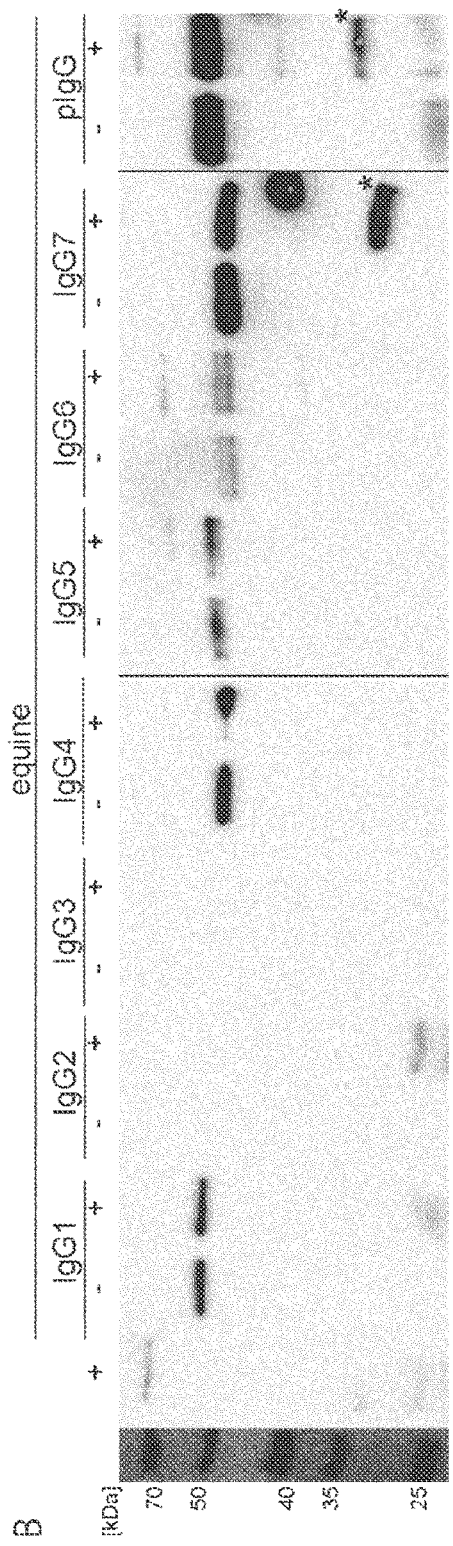

FIG. 12. rIgdEequi cleaves exclusively equine IgG7.

0.6 µM recombinant equine IgG subtypes or serum IgG were incubated for 16 h at 37° C. with (+) or without (−) the soluble fraction of *E. coli* cells expressing rIgdE$_{equi}$. Reactions were analyzed by SDS-PAGE under reducing conditions. IgG cleavage (*) occurred upon incubation with IgG7 and serum IgG. SDS-PAGE was either stained with Coomassie Fluor Orange Protein Gel Stain (A) or subjected to Western blot (B) analyses with Rabbit Anti-Horse IgG H&L (HRP) ab6921.

DETAILED DESCRIPTION OF THE INVENTION

Brief Description of the Sequences

SEQ ID NO: 1 is the amino acid sequence of the IgdE isolated from *S. suis* strain 10. Additional amino acid sequences of IgdEs from *S. suis* can be found e.g. in GenBank as accession nos WP_012027720.1, WP_044687717.1, WP_045002893.1, WP_044981166.1, WP_044770432.1, WP_043041527.1, WP_014917307.1, WP_044981141.1, WP_044766031.1, WP_044780628.1, WP_044980481.1, WP_044768304.1, WP_043033176.1, WP_044772573.1, ABQ42883.1, ABQ42882.1, ABQ42884.1, ABQ42885.1, WP_024402604.1, WP_044671803.1, WP_014639000.1, WP_014636499.1, WP_044475270.1, WP_044683049.1, WP_044682603.1, WP_044982674.1, WP_024406212.1, WP_024402376.1, WP_024382860.1, WP_044684005.1, WP_044688055.1, WP_044754153.1, WP_024412941.1, WP_029172805.1, AER15932.1, WP_024414493.1, WP_044762560.1, WP_024417771.1, WP_044675281.1, WP_044666819.1, WP_043032980.1, WP_044671755.1, WP_024416363.1, ABL84354.1, ABL84413.1, WP_044758899.1, WP_024393919.1, WP_014736321.1, WP_024383620.1, WP_044475488.1, WP_024386700.1, WP_024381951.1, WP_024390579.1, WP_023371419.1, WP_044772576.1, WP_044766774.1, WP_044672596.1, WP_043028752.1, WP_044771508.1, WP_024383851.1, WP_024388957.1, WP_024394959.1, WP_029174632.1, WP_044752120.1, WP_044678077.1, WP_002938262.1, WP_044769991.1, WP_044770681.1, WP_044749736.1, and WP_044771392.1.

SEQ ID NO: 2 is a nucleic acid sequence encoding IgdE isolated from *S. suis* strain 10.

SEQ ID NO: 3 is the amino acid sequence of an IgdE isolated from *S. agalactiae* strain CCUG4208. Additional amino acid sequences of IgdEs from *S. agalactiae* can be found e.g. in GenBank as accession nos EPU21342.1, EFV98161.1, CAD47554.1, EPU23939.1, EPW71972.1, EPT99261.1, EPV90329.1, EGS26825.1, EPV84888.1, CFQ52811.1, EPT84780.1, EPT99074.1, CCW42936.1, CCW40848.1, EAO70450.1, EPU74838.1, EPT51236.1, EPU77761.1, EPT36280.1, WP_011058381.1, EPT59860.1, EPT39170.1, EPT38734.1, CFQ25568.1, EPU40877.1, WP_025193619.1, WP_000440329.1, WP_000440333.1, WP_000440330.1, WP_000440331.1, WP_047199154.1, WP001901206.1, WP_025193273.1, WP_025194923.1, WP_000440334.1, WP_025195559.1, WP_047200043.1, WP_041165773.1, EPU33307.1, CFW66620.1, WP_041981191.1, WP_000440332.1, WP_047200261.1, WP_029692083.1, WP_017770870.1, WP_025197885.1, EAO75153.1, WP_001884472.1, EAO62452.1, WP_025195776.1, WP_047200280.1, CFW66618.1, and EAO75155.1.

SEQ ID NO: 4 is a nucleic acid sequence encoding IgdE isolated from *S. agalactiae* strain CCUG4208.

SEQ ID NO: 5 is the amino acid sequence of the IgdE isolated from *S. porcinus* strain DSM20725. The amino acid sequences of IgdE from *S. porcinus* can be found e.g. in GenBank as accession no WP_003085269.1

SEQ ID NO: 6 is a nucleic acid sequence encoding IgdE isolated from *S. porcinus* strain DSM20725.

SEQ ID NO: 7 is the amino acid sequence of the IgdE isolated from *S. equi* strain ssp *zooepidemicus* #1. Additional amino acid sequences of IgdEs from *S. equi* can be found e.g. in GenBank as accession nos. KDE01980.1, KIS07668.1, KIS08707.1, KIS19971.1, WP_043038795.1, WP_043036602.1, WP_037584076.1, KIS20896.1, AIA68804.1, WP_043029522.1, WP_012678259.1, WP_042670323.1, WP_043040324.1, and WP_014622546.1.

SEQ ID NO: 8 is a nucleic acid sequence encoding IgdE isolated from *S. equi* strain ssp *zooepidemicus* #1.

SEQ ID NO: 9 is the amino acid sequence of the IgdE isolated from *S. pseudoporcinus* strain ATCC® BAA-1381.

The amino acid sequences of IgdE from *S. pseudoporcinus* can be found e.g. in GenBank as accession no WP_007895676.1.

SEQ ID NO: 10 is a nucleic acid sequence encoding IgdE isolated from *S. pseudoporcinus* strain ATCC BAA-1381.

SEQ ID NO: 11 is the amino acid sequence of a C-terminally truncated variant of IgdE isolated from *S. suis*.

IgdE Polypeptides

The IgdE polypeptide according to the present invention is preferably an IgdE$_{suis}$, IgdE$_{agalactiae}$, IgdE$_{porcinus}$, IgdE$_{equi}$, or an IgdE$_{pseudoporcinus}$ polypeptide, or a variant or fragment of any thereof which retains cysteine protease activity and/or is capable to raise an immune response to a *streptococcus* in a subject. The variant may be an IgdE polypeptide from another bacterium. The bacterium is preferably a *Streptococcus*.

The IgdE polypeptide may comprise the amino acid sequence of SEQ ID NO: 1, 3, 5, 7, 9, 11; or a variant of any one thereof having at least 70% identity to the amino acid sequence of any of SEQ ID NOs: 1, 3, 5, 7, 9, or 11 and having IgG degrading cysteine protease activity; or a fragment of SEQ ID NOs: 1, 3, 5, 7, 9, 11; or a variant of any one thereof having IgG degrading cysteine protease activity.

The IgdE polypeptide may comprise the amino acid sequence of SEQ ID NOs: 1, 3, 5, 7, 9, 11; or a variant of any one thereof having at least 70% identity to the amino acid sequence of any of SEQ ID NOs: 1, 3, 5 7, 9, or 11 and being capable to raise an immune response to a *streptococcus* in a subject; or a fragment of SEQ ID NOs: 1, 3, 5, 7, 9, 11; or a variant of any one thereof being capable to raise an immune response to a *streptococcus* in a subject.

The *streptococcus* can be *S. suis*, *S. agalactiae*, *S. porcinus*, *S. equi*, or *S. pseudoporcinus*.

Preferably, the polypeptide comprises, or consists of, any of the sequences of SEQ ID NOs: 1, 3, 5, 7, 9, or 11.

The polypeptide may additionally include a signal sequence or a N-terminal methionine.

Variant polypeptides are those for which the amino acid sequence varies from that in SEQ ID NOs: 1, 3, 5, 7, 9, or 11 respectively, but which retain the same essential character or basic functionality as IgdE. The variant polypeptides may therefore display IgG degrading cysteine protease activity, and/or be capable of raising an immune response to a *streptococcus* in a subject. Preferably the immune response is a protective immune response. Preferably the immune response generates antibodies able to neutralize the IgG degrading cysteine protease activity of the IgdE of an infectious *streptococcus* in the immunized subject. Notably, an IgdE variant lacking the IgG cysteine protease activity can still be able to raise an immune response generating antibodies being able to neutralize the IgG cysteine protease activity of the IgdE of an infectious *streptococcus* in the immunized subject. Such IgdE variants are included in the IgdE variants according to the invention.

Typically, polypeptides with more than about 70% identity, preferably at least 80%, at least 90% and particularly preferably at least 95%, at least 97% or at least 99% identity, with the amino acid sequence of SEQ ID NOs: 1, 3, 5, 7, 9, or 11 are considered variants of the protein. Such variants may include allelic variants and the deletion, modification or addition of single amino acids or groups of amino acids within the protein sequence, as long as the peptide maintains the basic IgdE functionality. The identity of variants of SEQ ID NOs: 1, 3, 5, 7, 9, or 11 may be measured over a region of at least 50, at least 75, at least 100, at least 150, at least 200, at least 250, at least 275, at least 300 or more contiguous amino acids of the sequence shown in SEQ ID NOs: 1, 3, 5, 7, 9, or 11, or more preferably over the full length of SEQ ID NOs: 1, 3, 5, 7, 9, or 11. It will be appreciated that any of the above listed lower limits may be combined with any of the above listed upper limits to provide a range for the length of the polypeptide of the invention. For example, the polypeptide may be 50 to 250 amino acids in length, or 100 to 300 amino acids in length. The polypeptide may be 100 to 586 amino acids in length, 150 to 500 amino acids in length or 100 to 400 amino acids in length.

Amino acid identity may be calculated using any suitable algorithm. For example the UWGCG Package provides the BESTFIT program which can be used to calculate homology (for example used on its default settings) (Devereux et al. (1984) Nucleic Acids Research 12, 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al. (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. ScL USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant sequences typically differ by at least 1, 2, 5, 10, 20, 30, 50 or more amino acids positions (which maybe substitutions, deletions or insertions of amino acids). For example, from 1 to 50, 2 to 30, 3 to 20 or 5 to 10 amino acid substitutions, deletions or insertions may be made. The substitutions are preferably conservative substitutions, for example according to the following Table 1. Amino acids in the same block in the second column and preferably in the same line in the third column may be substituted for each other:

TABLE 1

| ALIPHATIC | Non-polar | Gly Ala Pro |
| | | Ile Leu Val |
| | Polar-uncharged | Cys Ser Thr Met |
| | | Asn Gln |
| | Polar-charged | Asp Glu |
| | | Lys Arg |
| AROMATIC | | His Phe Trp Tyr |

Unless otherwise specified, the modifications are preferably conservative amino acid substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table A1 below. Where amino acids have similar polarity, this can be determined by reference to the hydropathy scale for amino acid side chains in Table A2.

TABLE A1

| Chemical properties of amino acids | |
| --- | --- |
| Ala (A) | aliphatic, hydrophobic, neutral |
| Cys (C) | polar, hydrophobic, neutral |
| Asp (D) | polar, hydrophilic, charged (−) |
| Glu (E) | polar, hydrophilic, charged (−) |
| Phe (F) | aromatic, hydrophobic, neutral |
| Gly (G) | aliphatic, neutral |
| His (H) | aromatic, polar, hydrophilic, charged (+) |
| Ile (I) | aliphatic, hydrophobic, neutral |
| Lys (K) | polar, hydrophilic, charged(+) |
| Leu (L) | aliphatic, hydrophobic, neutral |
| Met (M) | hydrophobic, neutral |
| Asn (N) | polar, hydrophilic, neutral |
| Pro (P) | hydrophobic, neutral |
| Gln (Q) | polar, hydrophilic, neutral |
| Arg (R) | polar, hydrophilic, charged (+) |
| Ser (S) | polar, hydrophilic, neutral |
| Thr (T) | polar, hydrophilic, neutral |
| Val (V) | aliphatic, hydrophobic, neutral |
| Trp (W) | aromatic, hydrophobic, neutral |
| Tyr (Y) | aromatic, polar, hydrophobic |

TABLE A2

| Hydropathy scale | |
| --- | --- |
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

Preferably the polypeptides comprise a cysteine residue and a histidine residue at a spacing typically found in cysteine proteases. For example, in SEQ ID NO: 1, these residues are found at position 302 and position 333. An aspartic acid residue completing the catalytic triad is found at position 348.

The fragment of the IgdE polypeptide used in the invention is typically at least 10, for example at least 15, 20, 25, 30, 40, 50 or more amino acids in length, up to 100, 150, 200, 250 or 300 amino acids in length, as long as it retains the IgG degrading cysteine protease activity of IgdE and/or being capable of raising an immune response to a streptococcus in a subject.

The polypeptides used in the invention may be chemically modified, e.g. post-translationally modified. For example, they may be glycosylated, phosphorylated or comprise modified amino acid residues. They may be modified by the addition of histidine residues to assist their purification or by the addition of a signal sequence to promote insertion into the cell membrane. Such modified polypeptides fall within the scope of the term "polypeptide" used herein.

Typically, polypeptides for use in accordance with the invention display immunoglobulin cysteine protease activity, and in particular IgG degrading cysteine protease activity. Preferably, the polypeptide cleaves IgG in the hinge region and more particularly in the hinge region of the heavy chain. Preferably, cleavage results in production of Fc and Fab fragments of IgG. Preferably the activity is specific for IgG. The IgG degrading cysteine protease activity may be determined by means of a suitable assay. For example, a test polypeptide may be incubated with IgG at a suitable temperature, such as 37° C. The starting materials and the reaction products may then be analysed by SDS PAGE to determine whether the desired IgG cleavage product is present. Typically this cleavage product is a 32 kDa fragment. Typically there is no further degradation of IgG after this first cleavage. The cleavage product may be subjected to N-terminal sequencing to verify that cleavage has occurred in the hinge region of IgG.

The cysteine protease activity of the polypeptides can be further characterised by inhibition studies. Preferably, the activity is inhibited by the peptide derivate Z-LVG-CHN2, and/or by iodoacetic acid which are protease inhibitors.

The IgG degrading cysteine protease activity of the polypeptides is generally IgG-specific in that the polypeptides may not degrade other classes of Ig, namely IgM, and IgA, when incubated with these immunoglobulins under conditions that permit cleavage of IgG. IgdE from *S. suis*, *S. porcinus*, and *S. pseudoporcinus* were found to be specific for porcine IgG. IgdE from *S. agalactiae* was found to be specific for human IgG, and specifically human IgG1. IgdE from *S. equi* was found to be specific for equine IgG, and specifically equine IgG7.

Polypeptides for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

Polypeptides for use in the present invention may be isolated from any suitable organism that expresses an IgdE polypeptide. Typically, the IgdE polypeptide is isolated from suitable IgdE expressing streptococcal strains. Suitable organisms and strains may be identified by a number of techniques. For example, streptococcal strains may initially be tested for the presence an igdE gene. Polynucleotide primers or probes may be designed based on for example, SEQ ID NOs: 2, 4, 6, 8, or 10. Examples of suitable primers are set out in SEQ ID NOs: 12-22. The presence of the igdE gene can then be verified by PCR using the primers or by hybridisation of the probes to genomic DNA of the strain.

Polynucleotides

A polynucleotide according to the invention may comprise or consist of: (a) the coding sequence of SEQ ID NOs: 4, 5, 6, 8, or 10; (b) a sequence which is degenerate as a result of the genetic code to the sequence as defined in (a); (c) a sequence having at least 70% identity to a sequence as defined in (a) or (b) and which encodes a polypeptide having IgG degrading cysteine protease activity and/or be capable of raising an immune response to a *streptococcus* in a subject; or (d) a fragment of any one of the sequences as defined in (a), (b) or (c) which encodes a polypeptide having IgG degrading cysteine protease activity and/or be capable of raising an immune response to a *streptococcus* in a subject.

Typically the polynucleotide is DNA. However, the polynucleotide may be a RNA polynucleotide. The polynucleotide may be single or double stranded, and may include within it synthetic or modified nucleotides. A polynucleotide of the invention can typically hybridize to the coding sequence or the complement of the coding sequence of SEQ ID NOs: 2, 4, 6, 8, or 10 at a level significantly above background. Background hybridization may occur, for example, because of other DNAs present in a DNA library. The signal level generated by the interaction between a polynucleotide of the invention and the coding sequence or complement of the coding sequence of SEQ ID NOs: 2, 4, 6, 8, or 10 is typically at least 10 fold, preferably at least 100 fold, as intense as interactions between other polynucleotides and the coding sequence of SEQ ID NOs: 2, 4, 6, 8, or 10. The intensity of interaction may be measured, for example, by radiolabelling the probe, e.g. with $^{32}$P. Selective hybridisation may typically be achieved using conditions of medium to high stringency. However, such hybridisation may be carried out under any suitable conditions known in the art (see Sambrook et al., Molecular Cloning: A Laboratory Manual, 1989). For example, if high stringency is required suitable conditions include from 0.1 to 0.2×SSC at 60° C. up to 65° C. If lower stringency is required suitable conditions include 2×SSC at 60° C.

The coding sequence of SEQ ID NOs: 2, 4, 6, 8, or 10 may be modified by nucleotide substitutions, for example from 1, 2 or 3 to 10, 25, 50 or 100 substitutions. The polynucleotide of SEQ ID NO: 2, 4, 6, 8, 10 may alternatively or additionally be modified by one or more insertions and/or deletions and/or by an extension at either or both ends. Additional sequences such as signal sequences may also be included. The modified polynucleotide generally encodes a polypeptide which has IgdE specific cysteine protease activity and/or is capable of raising an immune response to a *streptococcus* in a subject. Degenerate substitutions may be made and/or substitutions may be made which would result in a conservative amino acid substitution when the modified sequence is translated, for example as shown in the Table 1 above.

A nucleotide sequence which is capable of selectively hybridizing to the complement of the DNA coding sequence of SEQ ID NOs: 2, 4, 6, 8, or 10 will generally have at least 70%, at least 80%, at least 90%, at least 95%, at least 98% or at least 99% sequence identity to the coding sequence of SEQ ID NO: 2, 4, 6, 8, or 10 respectively, over a region of at least 20, preferably at least 30, for instance at least 40, at least 60, more preferably at least 100 contiguous nucleotides or most preferably over the full length of SEQ ID NO: 2, 4, 6, 8, or 10. Sequence identity may be determined by any suitable method, for example as described above.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 20, preferably over 30 nucleotides forms one aspect of the invention, as does a polynucleotide which has at least 95% sequence identity over 40 nucleotides. Polynucleotide fragments will preferably be at least 10, preferably at least 15 or at least 20, for example at least 25, at least 30 or at least 40 nucleotides in length. They will typically be up to 40, 50, 60, 70, 100 or 150 nucleotides in length. Fragments can be longer than 150 nucleotides in length, for example up to 200, 300, 400, 500, 600, 700, 800, 900 or 1000 nucleotides in length, or even up to a few nucleotides, such as five, ten or fifteen nucleotides, short of the coding sequence of SEQ ID NO: 2, 4, 6, 8, or 10 respectively.

Polynucleotides for use in the invention may be produced recombinantly, synthetically, or by any means available to those of skill in the art. They may also be cloned by standard techniques. The polynucleotides are typically provided in isolated and/or purified form.

In general, short polynucleotides will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the igdE gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. Suitable primers are for example, those in SEQ ID NOs: 12-22.

Such techniques may be used to obtain all or part of the igdE gene sequence described herein. Although in general the techniques mentioned herein are well known in the art, reference may be made in particular to Sambrook et al. (1989). IgdE polynucleotides as described herein have utility in production of the polypeptides for use in the present invention, which may take place in vitro, in vivo or ex vivo. The polynucleotides may be used as therapeutic agents in their own right or may be involved in recombinant protein synthesis.

The polynucleotides for use in the invention are typically incorporated into a recombinant replicable vector. The vector may be used to replicate the nucleic acid in a compatible host cell. Therefore, polynucleotides for use in the invention may be made by introducing an IgdE polynucleotide into a replicable vector, introducing the vector into a compatible host cell and growing the host cell under conditions which bring about replication of the vector.

Preferably the vector is an expression vector comprising a nucleic acid sequence that encodes an IgdE polypeptide. Such expression vectors are routinely constructed in the art of molecular biology and may for example involve the use of plasmid DNA and appropriate initiators, promoters, enhancers and other elements, such as for example polyadenylation signals, which may be necessary and which are positioned in the correct orientation in order to allow for protein expression. Other suitable vectors would be apparent to persons skilled in the art. By way of further example in this regard we refer to Sambrook et al. (1989).

Preferably, a polynucleotide for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with an origin of replication, optionally a promoter for the expression of the said polynucleotide and optionally a regulator of the promoter. The vector is typically adapted to be used in vivo.

Promoters and other expression regulation signals may be selected to be compatible with the host cell for which expression is designed. Mammalian promoters, such as (3-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art. The vector may further include sequences flanking the polynucleotide giving rise to polynucleotides which comprise sequences homologous to eukaryotic genomic sequences, preferably mammalian genomic sequences. This will allow the introduction of the polynucleotides of the invention into the genome of eukaryotic cells by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

Diseases and Conditions

The IgdE polypeptide, or polynucleotide, may be used to treat or prevent diseases or conditions mediated by pathogenic IgG antibodies. It is well known in the art that pathogenic IgG antibodies are involved in the pathogenesis of a number of different diseases and conditions. Consequently, the effects of pathogenic IgG antibodies in such diseases can be inhibited using an IgdE polypeptide or polynucleotide.

The disease or condition can be an autoimmune disease. Such diseases include Addison's disease, alopecia areata, ankylosing spondilitis, antiphospho lipid syndrome, aplastic anaemia, autoimmune gastritis, autoimmune hearing loss, autoimmune haemolytic anaemias, autoimmune hepatitis, autoimmune hypoparathyroidism, autoimmune hypophysitis, autoimmune inner ear disease, autoimmune lymphoproliferative syndrome, autoimmune myocarditis, autoimmune oophoritis, autoimmune orchitis, autoimmune polyendocrinopathy, Bechet's disease, bullous pemphigoid, cardiomyopathy, chronic inflammatory demyelinating polyneuropathy, Churg-Strauss syndrome, coeliac disease, Crohn's disease, CREST syndrome, Degos disease, epidermolysis bullosa acquisita, essential mixed cryoglobulinaemia, giant cells arteritis, glomerulonephritis, Goodpasture's syndrome, Graves' disease, Guillan-Barre syndrome, Hashimoto's thyroiditis, idiopathic thrombocytopenic purpura, inflammatory bowel disease, Kawasaki's disease, Meniere's syndrome, mixed connective tissue disease, Mooren's ulcer, multiple sclerosis, myasthenia gravis, pemphigus foliaceous, pemphigus vulgaris, pernicious anaemia, polyarteritis *nodosa*, polyglandular autoimmune syndrome type 1 (PAS-I), polyglandular autoimmune syndrome type 2 (PAS-2), polyglandular autoimmune syndrome type 3 (PAS-3), polymyositis/dermatomyositis, primary biliary cirrhosis, psoriasis, psoriatic arthritis, Raynaud's syndrome, Reiter's syndrome, rheumatoid arthritis, sarcoidosis, scleroderma, Sjogren's syndrome, subacute thyroiditis, sympathetic opthalmia, systemic lupus erythematosus, Takayasu's arteritis, type 1 diabetes mellitus, vitiligo, Vogt-Koyanagi-Harada disease or Wegener's granulomatosis. Preferably the autoimmune disease is rheumatoid arthritis (RA).

The disease or condition can be asthma. The asthma can be acute or chronic asthma.

IgG activates the classical pathway of the complement system. IgdE polypeptides and polynucleotides can therefore be used to treat diseases and conditions where complement activation is detrimental to the patient. For example, the IgdE polypeptides and polynucleotides can be used to treat transplantation-derived disorders, for example transplant rejection (such as allograft and xenograft rejection) and graft-versus-host disease. The transplantation-derived disorder may occur due to the transplantation of a tissue or an organ in a patient.

IgdE polypeptides and polynucleotides are also of use in post-operative treatment, for example in the treatment of patients who have undergone heart by-pass operations.

Further, IgdE polypeptides and polynucleotides can be used for the treatment of acquired haemophilia, i.e to remove IgG in haemophilia patients who have developed autoantibodies against coagulation factors.

The term "a subject" as used herein includes any mammalian subject such as a human, a pig, a horse, and any cattle.

In Vitro Methods

The invention encompasses in vitro methods for the cleavage of IgG, comprising contacting IgG with a polypeptide comprising:

(a) the amino acid sequence of SEQ ID NO: 1, 3, 5, 7, 9 or 11;

(b) a variant thereof having at least 70% identity to the amino acid sequence of SEQ ID NO: 1, 3, 5, 7, 9 or 11 and having IgG cysteine protease activity; or (c) a fragment thereof of either (a) or (b), having IgG cysteine protease activity.

In a preferred embodiment, the amino acid sequence is SEQ ID NO: 3. The in vitro method for the cleavage of IgG comprises contacting IgG with a polypeptide comprising:

(a) the amino acid sequence of SEQ ID NO: 3;

(b) a variant of SEQ ID NO: 3 having at least 70% identity to the amino acid sequence of SEQ ID NO: 3 and having IgG cysteine protease activity;

(c) a fragment of SEQ ID NO: 3 or a fragment of a variant of SEQ ID NO: 3, having IgG cysteine protease activity.

In the preferred embodiment, the polypeptide is specific for human IgG, and specifically human IgG1. Furthermore, the polypeptide cleaves IgG1 as shown in FIG. 4, irrespective of whether the light chain is kappa or lambda type.

The polypeptide is an IgG cysteine protease, which may typically comprise a catalytic site including a cysteine residue, a histidine residue and an aspartic acid residue in positions which correspond to positions 265, 296 and 311 of SEQ ID NO: 1. For example, in SEQ ID NO:3 a cysteine residue, histidine residue and an aspartic acid residue are found at positions 262, 293 and 308. The variants and fragments of the polypeptide typically retain these residues.

The method of the present invention comprises incubating the polypeptide with a sample containing IgG under conditions which permit specific cysteine protease activity to occur. The method further comprises identification and/or isolation of the cleavage products. The analysis may be by any suitable method known in the art. In some instances, the analysis is by gel electrophoresis (e.g. SDS-PAGE) or mass spectrometry.

In another embodiment of the present invention, the in vitro method is used to generate Fc or Fab fragments of IgG. The method comprises contacting IgG with a polypeptide of the invention.

In a further embodiment of the invention, the method of the invention is used to detect IgG. This may comprise (i) contacting a sample with a polypeptide under conditions that permit the IgG specific cysteine protease activity of the polypeptide; and (ii) monitoring for the presence of IgG specific cleavage fragments; wherein the presence of the specific cleavage fragments is indicative of IgG in the sample.

EXAMPLES

Example 1. Identification if IgdE from *S. suis*

Bacterial Strains and Growth Conditions

*S. suis* strain 10 is a virulent serotype 2 strain that has been used in several studies for mutagenesis and experimental infections of pigs (Smith et al. 1999. *Infect. Immun.* 67, 1750-1756). Strain 10M7 was kindly provided by Hilde Smith (AWG, Lelystad, Netherlands) (Smith et al. 1996. *Infect. Immun.* 64, 4409-4412). Streptococci were grown on Columbia agar plates with 6% sheep blood or in Bacto Todd-Hewitt broth (THB) under anaerobic conditions at 37° C. *Escherichia coli* strains were cultured in Luria Broth (LB). When appropriate, antibiotics were added at 50 µg/ml for kanamycin and 20 µg/ml for gentamycin.

Materials from Animals

Samples from experimentally infected piglets were drawn within a previous study. The protocol for this animal experiment was approved by the Committee on Animal Experiments of the Lower Saxonian State Office for Consumer Protection and Food Safety in Germany (permit no. 33.9-42502-04-07/1243). Collection of blood from conventional piglets for bactericidal assays was registered under N19/14 at the regional office in Saxonia, Germany. The animal studies were performed in strict accordance with the principles and recommendations outlined in the European Convention for the Protection of Vertebrate Animals Used for Experimental and Other Scientific Purposes (European Treaty Series, no. 123: http://www.conventions.coe.int/Treaty/en/Treaties/Html/123.htm) and the German Animal Protection Law.

Identification of the IgG Degrading Activity

*S. suis* strain 10M7 cultures were harvested at approximately $OD_{600}$ of ~0.6 and culture supernatants were sterile-filtrated through a 0.22 µM Express PLUS membrane filter (Millipore) prior to fractionating the culture supernatant with ammonium sulfate to 30% saturation. The resulting precipitate was discarded and ammonium sulfate was added to the remaining supernatant to a final concentration of 50% saturation. The second precipitate was resuspended in 1/100 of the starting volume with 20 mM Bis-Tris pH 6.8 and buffer exchange against the same buffer was performed by HiPrep 26/10 Desalting column (GE Healthcare). The material was further fractionated by FPLC on a HiTrap Q HP column (GE Healthcare). Proteins were eluted by a linear NaCl gradient, and fractions eluted at ~0.2 M NaCl were found to contain the IgG degrading activity. The active fractions were subjected to size exclusion chromatography (HiPrep 16/60 Sephacryl S-100 HR, GE Healthcare) and there the IgG degrading activity was eluted at ~37 ml elution volume. Active fractions were analyzed by SDS-PAGE and protein bands were subjected to Mass spectrometry analysis.

Mass Spectroscopy

MALDI-TOF mass spectroscopy was performed by Umea Protein Analysis Facility (Umea University). Peptides for MS analysis were prepared by in-gel digestion using trypsin (sequencing grade modified, Promega) and analyzed by ESI LC-MS/MS using an HCT ultra ETD II iontrap instrument (Bruker) linked to an Easy nano LC system (Proxeon). Processing, deconvolution and compound detection for the LC-MS/MS datasets was performed using the DataAnalysis software (4.0 SP4, Bruker). Database searches using the peaklists files of the processed datasets were performed using the Mascot search engine (Matrixscience) in the bacterial sequences of the NCBInr database. The search parameters permitted a mass error of 0.3 Da for both the MS and the MS/MS mode and variable modifications of methionine by oxidation, of cysteine by propionamide derivation and by N-terminal acetylation.

Screening of S. suis Strains for IgG Degrading Capacity

Culture supernatants of 15 different S. suis strains (Table 2) were isolated at $OD_{600}$ of ~0.6 and concentrated by addition of saturated ammonium sulfate solution to a final saturation of 50%. The precipitate was re-suspended in ½₀ of the starting volume in PBS following buffer exchange against PBS by Zeba Spin Desalting Columns 7K MWCO (Thermo Scientific). The 50% ammonium sulfate precipitation fraction of S. suis culture supernatants were used for IgG degradation analysis.

TABLE 2

S. suis strains used in this study

| Strain | Capsule type | Source (Reference) |
| --- | --- | --- |
| 10 | cps 2 | Smith et al. 1999. Infect. Immun. 67, 1750-1756 |
| A1731/94 | cps 1 | Allgaier et al. 2001. J Clin Microbiol. 39, 445-453 |
| P1/7 | cps 2 | Jacobs et al. 1994. Infect. Immun. 62, 1742-1748 |
| T15 | cps 2 | Smith et al. 1999. Infect. Immun. 67, 1750-1756 |
| 19841/1 | cps 2 | Allgaier ibid |
| 199 | cps 2 (human) | Baums et al. 2007. Appl. Environ. Microbiol. 73, 711-717 |
| MAC724 | cps 2 (human) | Baums ibid |
| B2795/96 | cps 7 | Allgaier ibid |
| B2441/96 | cps 2 | Allgaier ibid |
| A5505/93 | untypeable | Allgaier ibid |
| V2569/1 | cps 5 | Baums, unpublished |
| #451 | cps 7 | Unterweger et al. 2014. Berl. Münch Tierarztl. Wochenschr. 127, 194-201 |
| V3667/1 | cps 7 | Baums, unpublished |
| A5683/94 | cps 9 | Allgaier ibid |
| A3286/94 | cps 9 | Allgaier ibid |
| 5223 | cps 14 | Wisselink et al. 2002. J. Clin. Microbiol. 40, 2922-2929 |
| 10M7 | cps 2 | Smith et al. 1996. Infect. Immun. 64, 4409-4412 |
| 10 ΔideSsuis | cps 2 | Seele et al. 2013 J. Bacteria 195, 930-940 |
| 10 ΔigdE | cps 2 | this application |
| 10 ΔideSsuis ΔigdE | cps 2 | this application |
| 5223 | cps 14 | Wisselink ibid |

Generation of a ΔigdE Deletion Strain

In frame deletion of igdE was principally conducted as in Seele et al., 2013 (J. Bacteriol. 195, 930-940) with S. suis strain 10. For construction of the thermosensitive vector pSET5_ΔigdE a 618 bp 5'-igdE amplicon was generated with primers preProIgdEPstI (TCACTGCAGTTTTGGG-GAGTAGG, SEQ ID NO: 12) and postSSIgdEBamHI (ATGGATCCCAGTTCAGAACCTC, SEQ ID NO: 13) and a 612 bp 3'-igdE amplicon was generated with primers preEndIgdEBamHI (CGG-GATCCAGAGAAAAAGAGATCC, SEQ ID NO:14) and postEndIgdEEcoRI (AGGAATTCACCGTTATTGTAGCG, SEQ ID NO:15). These amplicons were cloned into pSET5 (18) with the restriction enzymes indicated in the names of the primers to generate pSET5_ΔigdE. Deletion clones were confirmed by selective PCR analysis and sequencing of genomic amplicons using primers IgdE-seq_frw (ATTGT-ATTTGGTGGAGGAG, SEQ ID NO:16) and IgdE-seq_rev (TTTAGCAGCTAAGTTGATACC, SEQ ID NO:17).

Sequence Analysis

Sequence analyses were performed using the SIB Bioinformatics Resource Portal Expasy (www.expasy.ch). SignalP 4.0 was run to identify a putative signal peptide and the respective cleavage sites (www.cbs.dtu.dk/services/SignalP/). In silico modelling of S. suis IgdE to identify the potential active site residues was performed using SWISS-MODEL (http://swissmodel.expasy.org/). A putative transmembrane region was identified using the consensus prediction web server TOPCONS (htp://topcons.cbr.su.se/) last accession 2015-11-06.

DNA Techniques and Primer Sequences

Primers were designed based on gene SSU_RS08150 in the genome S. suis P1/7. All PCRs were conducted with Phusion Master Mix HF (Thermo Scientific). All obtained plasmids were checked by restriction analyses, PCR and sequencing.

Cloning of S. suis igdE and Generation of IgdE Mutants

The S. suis igdE gene lacking the signal peptide coding sequences (encoding amino acid 38-1121) was amplified from chromosomal DNA of S. suis strain 10 as template using primers IgdE-frw_NcoI (GTTTCCATGGAT-GAAAACTCACATTTACAATCG, SEQ ID NO:18) and IgdE-rev_NotI (ACGTGCGGCCGCATAAGCTTCGTAC, SEQ ID NO:19) and cloned into pET_ZZ_1a after digestion with NcoI and NotI (Thermo Scientific). The entire insert was sequenced to verify the cloning and the sequence of S. suis igdE. The obtained sequence of S. suis strain 10 igdE was identical to the one of S. suis 05ZYH33 and contained an insertion of 32 amino acids compared to SSU_RS08150 of S. suis P1/7.

Directed mutagenesis of the putative active site residues C302 to S, H333 to A, and D348 to A were performed with QuickChange Lightning Multi Site-Directed Mutagenesis Kit (Agilent Technologies) and primers IgdE-C302S (AACGTCAGAAAGCGAT-GAGTGTAGGTTTCAGCACT, SEQ ID NO:20), IgdE-H333A (CAGAAGGTGTCCCGGCTGCTA-CAGCGCGTG, SEQ ID NO:21) and IgdE-D348A (TAAAAAGTGGCACACCATTGCCGGTACAGGTTTT-ATTACAG, SEQ ID NO:22) according to the manufacturer's instructions.

IgdE$^{\Delta C}$, consisting of the N-terminal 470 amino acids of S. suis IgdE was created by digesting full-length igdE in pZZ1a with restriction endonucleases XhoI (Thermo Scientific). The digested plasmids were purified, re-ligated and transformed into E. coli.

Expression and Purification of Recombinant *S. suis* IgdE

*E. coli* ArcticExpress (DE3)_RIL (Agilent Technologies) isolates carrying pET_ZZ_1a igdE, igdE$^{C302}$S, igdEH$^{302A}$, igdE$^{D302A}$ or igdE$^{ΔC}$ were grown to OD$_{600}$ 0.6 at 30° C. Protein expression was induced with 1 mM IPTG at 12° C. and incubation was continued for an additional 22 h.

Cells were lysed for crude extracts by BugBuster HT Protein Extraction Reagent (Novagen) or for purification by Stansted high pressure cell disrupter (Stansted Fluid Power) in 50 mM Bis-Tris pH 7, 0.5 M NaCl, 5% glycerol, 40 μM imidazole. The His-ZZ-tagged protein was purified on His-Trap FF (GE healthcare) using standard protocols. The tag was removed by enzymatic cleavage by Tev-protease for 20 h at 5° C. followed by a second round of purification on HisTrap FT. The flow through, containing untagged rIgdE, was collected. Recombinant IgdE$^{ΔC}$ was purified as described above with higher yields and purity compared to full-length rIgdE.

Qualitative IgG Degradation Analyses

To monitor IgG cleavage activity in concentrated and fractionated culture supernatants, samples were incubated with 1% porcine plasma in PBS for 16 h at 37° C. prior to Western blot analyses.

To identify the catalytic type of the IgG protease, the IgG degradation reaction was performed in the presence of 0.1-5 mM AEBSF (Sigma), 0.1-5 mM EDTA, 50-250 μM E-64 (Sigma), 0.1-5 mM Z-LVG-CHN$_2$ (Bachem), 0.1-5 mM Iodoacetamide (Sigma) or 1/200 to 1/50 dilution of complete protease inhibitor cocktail (Roche).

0.5 mg/ml of porcine IgG (Sigma) in PBS or of other species (human, goat, cow, horse and mouse; all Sigma) were incubated with either crude extracts of induced *E. coli* carrying *S. suis* IgdE constructs mentioned above or 10 nM purified rIgdE for 16 h at 37° C. prior subjection to SDS-PAGE under either reducing or non-reducing conditions.

To analyze degradation of endogenous IgG in porcine body fluids following dilutions were used: 1/10 for heart sac fluid, abdominal cavity fluid and joint fluid; 1/50 for serum; undiluted for cerebrospinal fluid. Cerebrospinal and joint fluids were either from piglets with fibrino-suppurative meningitis and synovialitis caused by *S. suis* infection or from piglets with no lesions. Otherwise IgG degradation analyses were conducted as mentioned above with purified rIgdE and analyzed by both SDS-PAGE and western blot analyses. Experiments were repeated at least three times and representative analyses are shown.

Quantitative IgG Degradation Analyses

For time course analyses and inhibitor profiles the IgG degradation reaction was performed with 0.25 mg/ml porcine IgG and 2 μM purified IgdE$^{ΔC}$ at 37° C. in PBS uninhibited or in the presence of 2.5 μM or 250 aM AEBSF (Sigma), EDTA, E-64 (Sigma), Iodoacetamide (Sigma), or Z-LVG-CHN$_2$ (Bachem). DMSO (Sigma) at 0.275%, corresponding to the DMSO content in 250 lM Z-LVG-CHN$_2$, was used as a solvent control. The reactions were continuously sampled and subjected to SDS-PAGE under reducing conditions. Protein bands were detected by staining with Coomassie Fluor™ Orange Protein Gel Stain (Invitrogen). The IgG degradation product was densitometrical quantified by imaging with LAS4000 imaging system (Fujifilm) and analyzed with Image Studio Version 3.1 (LI-COR Biosciences) software. Uninhibited over-night cleavage was set as 100% relative cleavage for the time course experiment. For the inhibitor profile the initial cleavage rate was calculated from the initial increase of cleavage product (0-25% relative cleavage) and the initial cleavage rate of the uninhibited reaction was set as 100% relative activity. Experiments were at least performed in triplicates. Statistical analyses were performed using GraphPad Prism Version 5.0.

SDS-PAGE and Western Blot Analyses

Samples for SDS-PAGE were prepared with either reducing or non-reducing sample buffer and heated to 95° C. for 5 min. 12% SDS-PAGE was either stained with Coomassie blue (Sigma), Coomassie Fluor™ Orange Protein Gel Stain (Invitrogen) or blotted to Hybond-P PVDF membrane (GE Healthcare) for western blot analyses. Membranes were blocked with 5% dry milk powder in 0.1% PBS-Tween, followed by incubation with horse-radish peroxidase conjugated antibodies. Goat anti-pig IgG-HRP (Thermo Scientific) and goat anti-porcine IgM-HRP (Thermo Scientific) was diluted 1:25'000 and goat anti-porcine IgA-HRP (Thermo Scientific) was diluted 1:12'500. Membranes were thoroughly washed with 0.1% PBS-Tween prior to development with Amersham ECL Select Western blotting detection reagent (GE Healthcare) according to manufactures instruction and pictured by LAS4000 imaging system (Fujifilm).

N-Terminal Edman Sequencing

*S. suis* IgdE processed porcine IgG was separated by SDS-PAGE as previously explained and transferred by semi-dry blotting on Hybond-P PVDF membrane (GE Healthcare) with 50 mM sodium-borate/20% MetOH as blotting buffer. The membrane was stained with Ponceau S (Sigma) and after drying the ~32 kDa degradation product was tightly cut out. N-terminal Edman sequencing of the degradation product was performed by Proteome Factory (Berlin, Germany) and the sequence W/C PICPACE was obtained. The first position sequence determination was complicated due to a likely contamination yielding a strong tryptophan peak and only a minor peak at the cysteine position. However, in BLAST homology searches the sequence indubitable scored porcine IgG hinge region sequences containing a cysteine residue in the corresponding position. Cysteines were identified by signals of propionamide modified cysteine, nevertheless cysteine is not part of the calibration standard.

ELISA

For detection of IgG titers against *S. suis* IgdE Maxisorb® plates (Nunc) were coated with 0.6 μg rIgdE protein using carbonate buffer. After coating the plates were washed three times with PBS plus 0.1% Tween 20 (PBST) and blocked with 5% milk powder in PBS for 2 h at 37° C. Every sample and the controls were measured in a duplicate series of four (positive reference serum: six) twofold dilutions in PBST starting with a dilution of 1:100. For the detection of *S. suis* IgdE specific IgG antibodies the plates were incubated with goat anti-pig IgG-HRP (1 mg/ml, Bethyl, A100-105P) at a dilution of 1:10000 for 1 h at 37° C. All incubation steps at 37° C. were performed on a shaker and after each incubation step the plates were washed with PBST. The plates were developed with 2,2-azino-di-[3-ethylbenzithiazo line sulphonate] (ABTS) and 0.003% H$_2$O$_2$ as substrate. Absorbance was measured at 405 nm in a microplate reader (Synergy H1, BioTek Instruments GmbH). Optical densities were converted to antibody concentrations through log linear regression analysis after background subtraction. The ELISA units for each sample were defined as the mean of the calculated units for each of the four dilutions of the two series. ELISA values obtained from a serum sample drawn 20 days after experimental infection with *S. suis* strain 10 was arbitrary set to 100 ELISA units, while ELISA values from serum samples derived from colostrum deprived piglets were used as negative control.

Results

S. suis Secretes an IgG-Cleaving Enzyme

Figure 1:
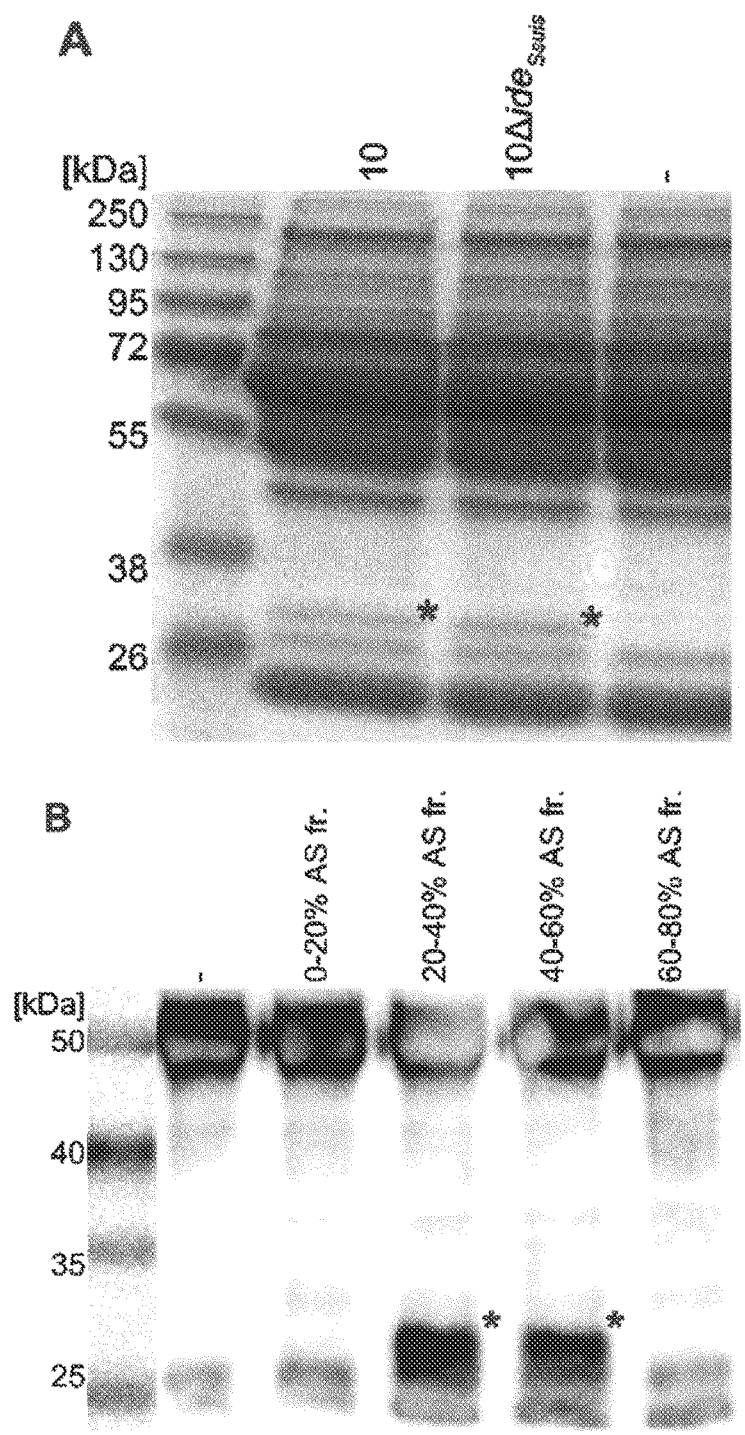
FIG. 1. IgG degradation activity in culture supernatants of S. suis.
Figure 1:
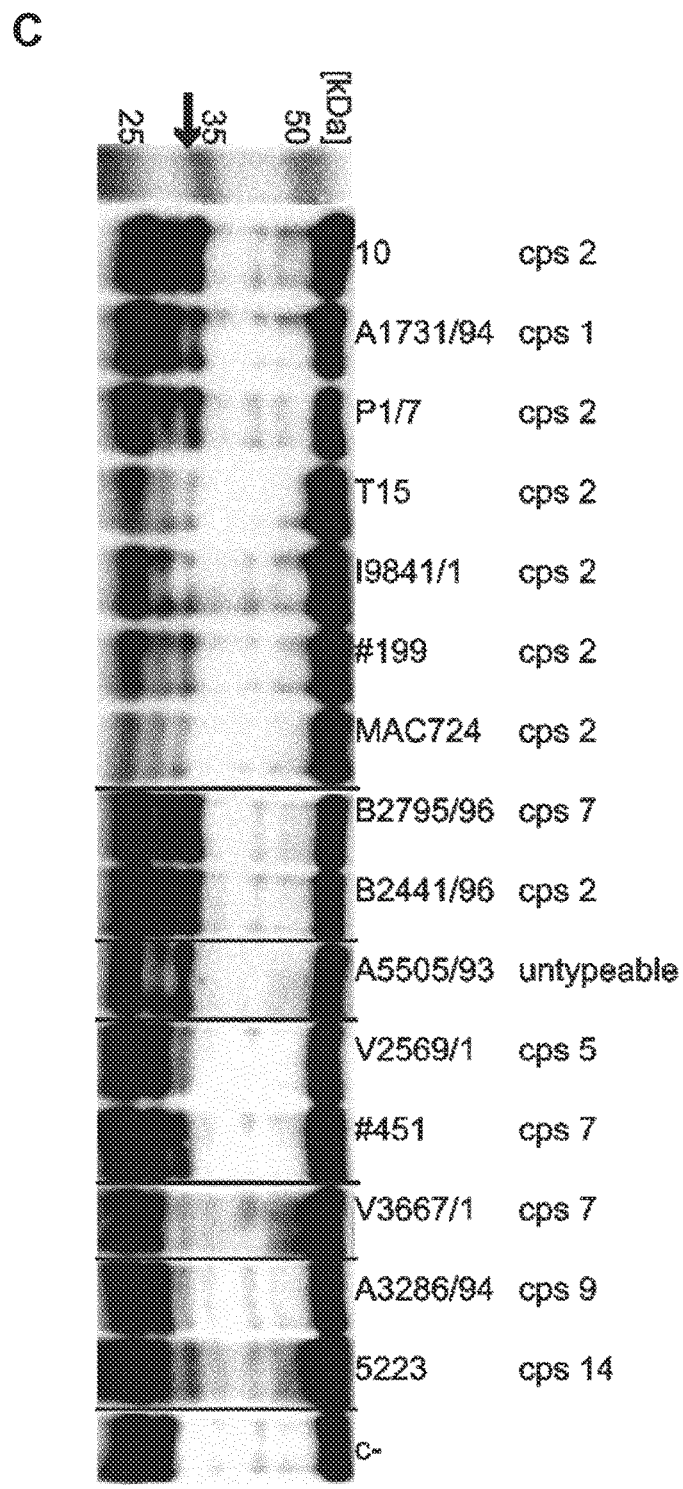

Proteolytic activities of extracellular enzymes of S. suis were analyzed by incubating concentrated supernatants of S. suis strain 10 and the isogenic IgM protease mutant 10Δide$_{Ssuis}$ with 2% porcine plasma as putative substrate. After 3 hours of incubation, the reaction was analyzed by reducing SDS-PAGE. Interestingly, the plasma protein band patterns obtained from bacterial culture supernatants of both wild type strain 10 and the isogenic IgM protease mutant 10Δide$_{Ssuis}$ contained an additional protein band of approximately 32 kDa, which was absent in the porcine plasma control (FIG. 1A). The 32 kDa band was excised, subjected to MALDI-TOF mass spectroscopy and identified as an IgG degradation product showing the presence of an IgG proteolytic activity in S. suis. To confirm this finding and to sustain that the proteolytic activity is due to a secreted enzyme of S. suis, growth supernatant of bacterial cultures was fractionated by adding increasing amounts of ammonium sulfate (0 to 80% saturation). Fractions were tested for IgG cleaving activity with porcine plasma and IgG degradation fragments were detected by Western blot using specific polyclonal anti-porcine IgG antibodies. Precipitates of 20 to 60% ammonium sulfate saturation clearly exhibited IgG-cleaving activity, demonstrating that the observed IgG proteolytic activity is distinct from the recently described IgM protease IdeS$_{suis}$(Seele supra) and due to a secreted protein in the culture supernatant of S. suis (FIG. 1B).

Culture supernatant of 15 different S. suis strains, including several strains of the clinical relevant serotype 2; two human isolates of serotype 2, and a set of strains representing additional serotypes (Table 2) were analyzed by Western blot as described above. For all strains an IgG cleavage product of approximately 32 kDa could be detected by Western blot analysis (FIG. 1C), indicating that IgG degradation activity is conserved among different S. suis strains.

Purification and Sequence Characteristics of IgdE, a Novel Protease of S. suis

Prior to a purification trial, protease enriched ammonium sulfate precipitates were tested for IgG cleaving activity in the presence of class specific protease inhibitors to preliminary classify the putative IgG protease. Metallo protease inhibitor EDTA did not affect IgG cleavage, while serine protease inhibitor AEBSF interfered moderately with IgG cleavage. Cysteine protease inhibitors E-64, Z-LVG-CHN$_2$ and iodoacetamide, however, all appeared to inhibit IgG degrading activity (FIG. 8). Thus, since active site cysteine residues can be inhibited by AEBSF (24, 25), the overall inhibitor profile is most consistent with the assumption that the IgG cleaving protease belongs to the class of cysteine proteases. For purification, strain S. suis 10M7, an isogenic mutant of strain 10, was used to avoid masking of low expressed proteins by the in culture supernatants highly abundant muraminidase-released protein (MRP). Bacterial culture supernatant was fractionated by ammonium sulfate precipitation and precipitates were subjected to anion-exchange chromatography and size exclusion chromatography (SEC). Samples showing IgG cleaving activity were separated by reducing SDS-PAGE. Protein bands were identified by MALDI-TOF mass spectrometry and similarity searches against NCBI databases using a pBLAST algorithm. Since the initial characterization of the IgG proteolytic enzyme indicated that the protease is most likely a secreted cysteine protease, sequences of identified proteins were screened for i) the presence of a cysteine residue within the core of the protein and ii) the presence of a secretion signal peptide. Beside Ide$_{Ssuis}$ that previously has been shown to be IgM specific two (out often) identified proteins contained a putative catalytic cysteine residue, but only one contained both a signal peptide sequence predicted by the SignalP algorithm and a core cysteine residue. This protein is annotated as a putative exported protein in the genomic sequences database of S. suis serotype 2 strains (www.sanger.ac.uk) and designated SSU_RS08150 in strain P1/7. SSU_RS08150 encodes a 1121 amino acid protein (GenBank accession no WP_012027720) with a putative transglutaminase core sequence motif located in the N-terminal half of the protein within amino acids 188 to 265. The TOPCONS consensus prediction of membrane protein topology identified a putative transmembrane helix in the C-terminal approximately between amino acids 1059-1080. The predicted size of 118 kDa (without signal sequence) is somewhat less than the estimated size of the initially purified protein band after SDS-PAGE (data not shown), which is due to the slightly slower migration of proteins with low pI (pI 4.66) on SDS-PAGE. The full-length putative protein sequence was used in similarity searches against NCBI databases using a pBLAST algorithm. This search revealed no similarities of the full-length protein to any known protease of the MEROPS peptidase database (Rawlings et al. 2014. Nucleic Acids Res. 42, 503-509); no similarities to any eukaryotic protein, but some similarity of the N-terminal half of the protease, containing the transglutaminase core motif, to hypothetical proteins of Streptococcus porcinus and Streptococcus pseudoporcinus (54% identity in a region of 480-492 amino acid residues) and a hypothetical protein of Streptococcus equi (up to 40% identity in a region of 264 to 406 amino acid residues). The N-terminal part of the protease shows also some similarity to hypothetical proteins of Streptococcus agalactiae and Streptococcus merionis (approximately 32% identity). The putative protein is in some databases denoted as ribonuclease or ribonucleases G and E, but due to the absence of an experimentally confirmed function and based on the enzymatic activity against porcine IgG, the protein was denoted IgdE for Immunoglobulin G degrading enzyme of Streptococcus suis.

IgdE is a Novel Cysteine Protease

The S. suis IgdE sequence reveals the presence of a single cysteine residue in position 302 that, due to the inhibitor profile, is assumed to represent the catalytic site cysteine. In silico 3D-modelling (http://swissmodel.expasy.org) of S. suis IgdE, using known transglutaminase domain structures as template, revealed a putative active site cleft in the N-terminal part of the protein containing a potential catalytic triad consisting of cysteine 302, histidine 333 and aspartic acid 348.

For identification of the putative protease domain and catalytic site residues of S. suis IgdE several recombinant IgdE constructs were created (FIG. 2A). All three putative catalytic site residues were replaced by site directed mutagenesis generating mutant proteins, IgdE$^{302S}$, IgdE$^{H333A}$ and IgdE$^{D348A}$ respectively. In addition, a construct lacking the C-terminal part of S. suis IgdE was created by an XhoI restriction enzyme cut-back. Crude soluble fractions of E. coli expressing these constructs were incubated with porcine IgG and analyzed by SDS-PAGE. In the presence of recombinant S. suis IgdE, the 32 kDa IgG-derived band appeared, demonstrating that the recombinant protein contains IgG proteolytic activity (FIG. 2B, lane 3). The IgG cleaving activity could be assigned to the N-terminal part of the protein, as a recombinant protein lacking amino acids 471 to 1121 is sufficient for IgG cleaving activity (FIG. 2B, lane 7). SDS-PAGE analysis of porcine IgG incubated with the mutant proteins (FIG. 2B, lane 4-6), revealed that neither rIgdE$^{C302S}$ nor rIgdE$^{H333A}$ exhibited IgG cleaving activity, while rIgdE$^{D348A}$ showed somewhat reduced IgG cleaving activity. Altogether, these data strongly indicate that these three residues are part of the catalytic site of S. suis IgdE.

The inhibitor screen was repeated with purified recombinant IgdEAC and class specific protease inhibitors. In contrast to classical transglutaminase enzymes, IgdE is not calcium dependent, as the protease is fully active in the presence of EDTA, while cysteine class specific inhibitors iodoacetamide and Z-LVG-CHN2 efficiently interfered with IgG proteolytic activity as no cleavage product at all could be detected at 125fold molar excess of inhibitor even after 18 h incubation (FIG. 3). The serine protease inhibitor AEBSF inhibited the IgdEAC moderately at 125 fold molar excess. Interestingly, E-64 did not inhibit purified IgdEAC in this experimental setting, which might be due to a narrow active site similar as described for other streptococcal Ig-proteases, like IdeS and Ide$_{Ssuis}$. However, at very high concentrations, E-64 interfered with IgG cleavage activity of S. suis culture supernatants (FIG. 8). Z-LVG-CHN2 a cysteine protease specific inhibitor structurally based on the inhibitory reactive site of cystatin C (Green and Shaw. 1981. J. Biol. Chem. 256, 1923-1928) completely inhibited IgdEAC at 125 fold molar excess. The inhibition of enzymatic activity with iodoacetamide and Z-LVG-CHN2 as well as the lack of enzymatic activity of the IgdEC302S and IgdEH333A mutant suggest that IgdE is a novel and so far unique member of the cysteine protease family.

S. suis IgdE Cleaves Porcine IgG with High Specificity in the Hinge Region

Porcine IgG degradation products were analyzed by reducing and non-reducing SDS-PAGE. The observed band pattern under non-reducing conditions is consistent with a cleavage site located in the hinge region of the heavy chain just N-terminal of the interconnecting disulfide bonds (FIG. 4A). IgG degradation products obtained under reducing conditions (FIG. 4B) were subjected to N-terminal Edman sequencing and the obtained sequence C*PICPACE was found in the hinge region sequences of porcine IgG2ab, IgG4ab, and IgG6ab subtypes. Similar sequences with CPICPGCE as common motif are present in the hinge region of IgG1ab and IgG5ab subtypes, while IgG3 exhibited a CPxxxxC sequence in the hinge region (Table3).

TABLE 3

N-terminal Edman sequencing of porcine IgG degradation products

| Sub-types | Hinge (corresponding to aa 99-121 of IgG1a) |
|---|---|
| IgG1a | G T K T K P P ↓ C P I C P G C E V A G |
| IgG1b | G I H Q P Q T ↓ C P I C P G C E V A G |
| IgG2a | G T K T K P P ↓ C P I C P A C E S P G |
| IgG2b | G T K T K P P ↓ C P I C P A C E A P G |
| IgG3  | D I E P P T P I ↓ C P E I C S C P A A E V L G A |
| IgG4a | G T K T K P P ↓ C P I C P A C E G P G |
| IgG4b | G I H Q P Q T ↓ C P I C P A C E G P A |
| IgG5a | G R P ↓ C P I C P G C E V A G |
| IgG5b | G K K T K P R ↓ C P I C P G C E V A G |

TABLE 3-continued

N-terminal Edman sequencing of porcine IgG degradation products

| Sub-types | Hinge (corresponding to aa 99-121 of IgG1a) |
|---|---|
| IgG6a | G R P ↓ C P I C P A C E G P G |
| IgG6b | G R P ↓ C P I C P A C E G N G |

Hinge region sequences of all porcine IgG sub-types. Cysteine residues believed to be involved in S-S covalent bonds (underlined) and the potential cleavage site (↓) are marked in the table.

The observed cleavage patterns on reducing and non-reducing SDS-PAGE; in addition to the identified cleavage site, are consistent with a cleavage reaction in which one IgG heavy chain is hydrolyzed just N-terminal of the homodimer disulfide bonds, before a second step hydrolysis cleaves the second heavy chain (FIG. 4C). Interestingly, sequences similar to the IgG hinge region could not be found in the heavy chain sequences of porcine IgA and IgM. Therefore S. suis IgdE specificity was further investigated employing specific antibodies against porcine IgG, IgM and IgA. Porcine plasma incubated with recombinant S. suis IgdE was analyzed by Western blot demonstrating that the protease targets IgG in porcine plasma, but does not cleave IgA or IgM (FIG. 5A).

The host specificity of the protease was investigated by incubation of purified S. suis IgdE with IgG preparations of humans, goat, bovine, horse and mouse (FIG. 5B). Interestingly, only pig IgG was found to be a substrate for this novel IgG protease. Thus, IgdE shows a pronounced species specificity and targets only porcine IgG.

To further evaluate the specificity of S. suis IgdE ex vivo, body fluids of healthy or diseased piglets were used. Fluids from heart sac, abdominal cavity, and joint, as well as cerebrospinal fluid and serum were treated with recombinant S. suis IgdE and analyzed by SDS-PAGE (FIG. 6A) and by Western blot using porcine IgG specific antibodies (FIG. 6B). No apparent change in the protein band pattern, except for the appearance of the diagnostic IgG cleavage product could be observed in the presence of rIgdE in heart sac, abdominal cavity and serum samples. Also no IgG, i.e. no cleavage products, were present in joint fluid and cerebrospinal fluids of healthy pigs. In contrast, all body fluids obtained from piglets with clinical signs, e.g. suffering from meningitis and synovialitis, contained IgG as consequence of an inflammatory response and again a single diagnostic 32 kDa band could be observed in all samples treated with rIgdE (FIG. 6). The specificity of S. suis IgdE is emphasized by the observation that no additional degradation products could be identified on SDS-PAGE following incubation of porcine body fluids with the protease. Thus, although it cannot be excluded that additional substrates exist, these results indicate that S. suis IgdE is a highly specific IgG protease, complementing the previously described IgA and IgM degrading proteases of S. suis (Seele supra; Zhang et al. 2010. Vet. Microbiol. 140, 171-175).

IgdE is the Sole IgG Cleaving Enzyme Expressed by S. suis

Strain 10 and strain 10Δide$_{Ssuis}$, the latter lacking IgM cleaving activity, were used to generate S. suis igdE in-frame deletion mutants. IgG and IgM cleaving activities in growth supernatant from wild type strain 10 were determined by Western blot using specific polyclonal anti-porcine IgG or IgM antibodies (FIG. 7). As expected, wild type strain 10 exhibited IgG and IgM cleaving activity (FIGS. 7A and B, lane 3), while supernatant of the isogenic mutant strain 10ΔigdE only contained IgM cleaving activity and neither IgG or IgM degradation was detectable in supernatant of double mutant strain 10Δide$_{Ssuis}$ ΔigdE (FIGS. 7A and B, lane 5) Thus, it appears that *S. suis* IgdE is required and sufficient to cleave porcine IgG and that no other IgG cleaving activity is released under these experimental conditions.

In Vivo Expression of *S. suis* IgdE

Weaning piglets are initially protected from bacterial infection through colostrum derived maternal antibodies. Levels of maternal antibodies decrease over time and active IgG mediated immunity develops at earliest after two weeks. Accordingly, levels of IgG antibodies in serum of colostrum-deprived piglets (SCDP) do not exceed background values in ELISA measurements. An ELISA was conducted with rIgdE as antigen to investigate different serum samples from piglets for the presence of antibodies directed against this IgG protease. A serum sample drawn 20 days after experimental infection with *S. suis* strain 10 contained very high titers against rIgdE (defined as 100 ELISA units, see Material and Methods). In contrast to SCDP that was used as negative control, significant amounts of specific antibodies against *S. suis* IgdE were detectable in seven out of nine 5-6 weeks old conventional weaning piglets (ELISA units ranging from 36 and 92). These results demonstrated that *S. suis* IgdE is an immunogenic antigen expressed by *S. suis* in vivo.

Example 2. Identification IgdE from Other *Streptococcus* Species

The coding sequences of all available *Streptococcus* genomes were downloaded from NCBI [ftp://ftp.ncbi.nlm.nih.gov/genomes/Bacteria/ on Aug. 21, 2015] and from PATRIC [ftp://ftp.patricbrc.org/patric2/ on Aug. 25, 2015].

As reference sequence for IgdE we used the RefSeq sequence WP_014636499.1. The N-terminal signal peptide and the C-terminal region only present in sequences from *S. suis* were removed, leaving amino acids 38-520, hereafter called "IgdE_domain".

IgdE_domain was used as query sequence in blastp searches (E-value cutoff 1 to keep all possible proteases) against the NCBI sequences as well as the PATRIC sequences. The obtained hits were in turn used as query sequences against the same databases, using the same parameters. From the list of matched sequences we chose those that in the second round had a match that overlap with the region matched in the first round, when IgdE was used as query. Sequences not containing the 'C' in the catalytic site were removed from further consideration, and in case of identical sequences only one copy was kept.

Many of the sequences found are annotated as S-layer proteins or as containing an S-layer homology domain W. These are often present in two or more copies in the same genome, and have a SxC or GxC motif in the catalytic site instead the AxC motif found in the original IgdE sequences. When searching all the sequences against Pfam, these sequences fit well to the Pfam model 'Transglut_core'. In order to remove these sequences, that are not members of the IgdE family, all sequences matching to the Transglut_core model with an E-value of at most 1e-6 were removed, as well as sequences lacking the AxC motif. The remaining sequences were cut at both ends to contain only the parts matching the IgdE_domain sequence. In cases this resulted in identical "domain" sequences only one copy was kept.

Proteases belonging to the IgdE family were identified in *S. porcinus, S. agalactiae, S. equi*, and *S. pseudoporcinus*. The protease were cloned, expressed and characterized.

Example 3. Properties of IgdE Isolated from *S. porcinus*

Recombinant IgdE$_{porcinus}$ cleaved purified polyclonal porcine IgG resulting in a 32 kDa degradation product detected by reducing SDS-PAGE.

No degradation product was observed when recombinant IgdE$_{porcinus}$ was incubated with purified polyclonal IgG from cow, horse, human, goat or mouse.

Recombinant IgdE$_{porcinus}$ cleaved IgG in porcine serum, but not IgM or IgA detected by anti-IgG, IgM and IgA Western blot analyses.

The N-terminal sequence of the 32 kDa degradation product of porcine IgG is CPICPACE as shown by N-terminal Edman sequencing indicating that that this protein has the same cleavage site as IgdE from *S. suis* within porcine IgG.

The recombinant IgdE$_{porcinus}$ was easily over-expressed and purified to great purity.

All tested *S. porcinus* strains showed the same porcine IgG cleaving phenotype in their growth culture supernatants as the recombinant protein.

Example 4. Properties IgdE Isolated from *S. agalactiae*

Recombinant IgdE$_{agalactiae}$ cleaved purified polyclonal human IgG resulting in a 32 kDa degradation product detected by reducing SDS-PAGE (FIG. 10).

Recombinant IgdE$_{agalactiae}$ cleaved purified monoclonal human IgG1 kappa and IgG1 lambda resulting in a 32 kDa degradation product detected by reducing SDS-PAGE (FIG. 10D).

No degradation product was observed when recombinant IgdE$_{agalactiae}$ was incubated with monoclonal human IgG2, IgG3 or IgG4 (FIG. 10D).

No degradation product was observed when recombinant IgdE$_{agalactiae}$ was incubated with purified polyclonal IgG from cow, horse, pig, goat and mouse (FIG. 10A).

Recombinant IgdE$_{agalactiae}$ cleaved IgG in human serum, but not IgM or IgA detected by anti-IgG, IgM and IgA Western blot analyses Recombinant IgdE$_{agalactiae}$ degrades human serum IgG1 completely to single cleaved IgG1 (FIG. 11).

The N-terminal sequence of the 32 kDa degradation product of human IgG is H (or G or S)TCPPCPAPE as shown by N-terminal Edman sequencing indicating that that this protein has the same cleavage site as papain in IgG1 in the hinge region N-terminal of the cysteine residues believed to be involved in H—H covalent bonds between the heavy chains.

Recombinant IgdE$_{agalactiae}$ was easily over-expressed and purified.

Example 5. Properties of IgdE Isolated from *S. equi*

Lysate of *E. coli* expressing recombinant IgdE$_{equi}$ cleaved purified polyclonal horse IgG resulting in a 32 kDa degradation product detected by reducing SDS-PAGE.

No degradation product was observed when recombinant IgdE$_{equi}$ was incubated with purified polyclonal IgG from cow, human, pig, goat, rat, rabbit and mouse.

Recombinant IgdE$_{equi}$ cleaved IgG in equine serum, but not IgM or IgA detected by anti-IgG, IgM and IgA Western blot analyses Recombinant IgdE$_{equi}$ cleaved purified monoclonal recombinant equine IgG7 resulting in a 32 kDa degradation product detected by reducing SDS-PAGE (FIG. 12).

No degradation product was observed when recombinant IgdE$_{equi}$ was incubated with recombinant monoclonal equine IgG1, IgG2, IgG3, IgG4, IgG5 or IgG6.

The N-terminal sequence of the 32 kDa degradation product of equine IgG as shown by N-terminal Edman sequencing is (G)PTCPECXGV. This sequence is found in the hinge region of equine IgG7.

Example 6. Properties of IgdE isolated from *S. pseudoporcinus*

*S. pseudoporcinus* culture supernatant possessed porcine IgG cleaving phenotype, but not human IgG cleaving phenotype.

Recombinant IgdE$_{pseudoporcinus}$ cleaved purified polyclonal human and porcine IgG resulting in a 32 kDa degradation product as detected by reducing SDS-PAGE.

No degradation product was observed when recombinant IgdE$_{pseudoporcinus}$ was incubated with purified polyclonal IgG from cow, horse, goat, mouse, or rat.

Recombinant IgdE$_{pseudoporcinus}$ cleaved IgG in human and porcine serum, but not IgM or IgA in porcine serum as detected by anti-IgG, IgM and IgA Western blot analyses.

The N-terminal sequence of the 32 kDa degradation product of porcine IgG is CPICPACE as shown by N-terminal Edman sequencing indicating that that this protein has the same cleavage site as IgdE within porcine IgG.

The recombinant IgdE$_{pseudoporcinus}$ was easily over-expressed in *E. coli* BL21 pLysS.

The invention described herein also relates to the following aspects:

1. A polypeptide for use in generating an immune response in a subject comprising:
    (a) the amino acid sequence of SEQ ID NO: 1;
    (b) a variant of SEQ ID NO: 1 having at least 70% identity to the amino acid sequence of SEQ ID NO: 1 and having IgG degrading cysteine protease activity;
    (c) a fragment of SEQ ID NO: 1, a variant of SEQ ID NO:1, or a fragment of a variant of SEQ ID NO: 1 which is capable of generating an immune response to a *streptococcus*, preferably a *S. suis* in a subject;
    (d) the amino acid sequence of SEQ ID NO: 3;
    (e) a variant of SEQ ID NO: 3 having at least 70% identity to the amino acid sequence of SEQ ID NO: 3 and having IgG degrading cysteine protease activity;
    (f) a fragment of SEQ ID NO: 3, a variant of SEQ ID NO:3, or a fragment of a variant of SEQ ID NO: 3 which is capable of generating an immune response to a *streptococcus*, preferably a *S. agalactiae* in a subject;
    (g) the amino acid sequence of SEQ ID NO: 5;
    (h) a variant of SEQ ID NO: 5 having at least 70% identity to the amino acid sequence of SEQ ID NO: 5 and having IgG degrading cysteine protease activity;
    (i) a fragment of SEQ ID NO: 5, a variant of SEQ ID NO:5, or a fragment of a variant of SEQ ID NO: 5 which is capable of generating an immune response to a *streptococcus*, preferably a *S. porcinus* in a subject;
    (j) the amino acid sequence of SEQ ID NO: 7;
    (k) a variant of SEQ ID NO: 7 having at least 70% identity to the amino acid sequence of SEQ ID NO: 7 and having IgG degrading cysteine protease activity;
    (l) a fragment of SEQ ID NO: 7, a variant of SEQ ID NO:7, or a fragment of a variant of SEQ ID NO: 7 which is capable of generating an immune response to a *streptococcus*, preferably a *S. equi* in a subject;
    (m) the amino acid sequence of SEQ ID NO: 9;
    (n) a variant of SEQ ID NO: 9 having at least 70% identity to the amino acid sequence of SEQ ID NO: 9 and having IgG degrading cysteine protease activity;
    (o) a fragment of SEQ ID NO: 9, a variant of SEQ ID NO:9, or a fragment of a variant of SEQ ID NO: 9 which is capable of generating an immune response to a *streptococcus*, preferably a *S. pseudoporcinus* in a subject;

2. A polynucleotide encoding a polypeptide according to aspect 1 for use in generating an immune response in a subject.

3. A polynucleotide for use in generating an immune response in a subject comprising:
    (a) SEQ ID NO: 2 or a complementary sequence thereto;
    (b) a sequence which is degenerate as a result of the genetic code to a sequence as defined in (a);
    (c) a sequence which hybridises under stringent conditions to the sequence defined in (a) or (b);
    (d) a sequence having at least 70% identity to a sequence as defined in (a) or (b);
    (e) a fragments of any of the sequences (a), (b), (c) or (d), and which encodes a polypeptide having IgG degrading cysteine protease activity and/or is capable of generating an immune response against a *streptococcus*, preferably a *S. suis* in a subject.
    (f) SEQ ID NO: 4 or a complementary sequence thereto;
    (g) a sequence which is degenerate as a result of the genetic code to a sequence as defined in (f);
    (h) a sequence which hybridises under stringent conditions to the sequence defined in (f) or (g);
    (i) a sequence having at least 70% identity to a sequence as defined in (f) or (g);
    (j) a fragments of any of the sequences (f), (g), (h) or (i), and which encodes a polypeptide having IgG degrading cysteine protease activity and/or is capable of generating an immune response against a *streptococcus*, preferably a *S. agalactiae* in a subject;
    (k) SEQ ID NO: 6 or a complementary sequence thereto;
    (l) a sequence which is degenerate as a result of the genetic code to a sequence as defined in (k);
    (m) a sequence which hybridises under stringent conditions to the sequence defined in (k) or (l);
    (n) a sequence having at least 70% identity to a sequence as defined in (k) or (l);
    (o) a fragments of any of the sequences (k), (l), (m) or (n), and which encodes a polypeptide having IgG degrading cysteine protease activity and/or is capable of generating an immune response against a *streptococcus*, preferably a *S. porcinus* in a subject;
    (p) SEQ ID NO: 8 or a complementary sequence thereto;
    (q) a sequence which is degenerate as a result of the genetic code to a sequence as defined in (a);
    (r) a sequence which hybridises under stringent conditions to the sequence defined in (p) or (q);
    (s) a sequence having at least 70% identity to a sequence as defined in (p) or (q);
    (t) a fragments of any of the sequences (p), (q), (r) or (s), and which encodes a polypeptide having IgG degrading cysteine protease activity and/or is capable of generating an immune response against a *streptococcus*, preferably a *S. equi* in a subject;

(u) SEQ ID NO: 10 or a complementary sequence thereto;

(v) a sequence which is degenerate as a result of the genetic code to a sequence as defined in (u);

(w) a sequence which hybridises under stringent conditions to the sequence defined in (u) or (v);

(x) a sequence having at least 70% identity to a sequence as defined in (u) or (v); or (y) a fragments of any of the sequences (u), (v), (w) or (x), and which encodes a polypeptide having IgG degrading cysteine protease activity and/or is capable of generating an immune response against a *streptococcus*, preferably *S. pseudoporcinus* in a subject.

4. A polypeptide for use in treatment or prevention of a disease or condition mediated by IgG antibodies comprising:

(a) the amino acid sequence of SEQ ID NO: 1;

(b) a variant of SEQ ID NO: 1 having at least 70% identity to the amino acid sequence of SEQ ID NO: 1 and having IgG degrading cysteine protease activity;

(c) a fragment of SEQ ID NO: 1 or a fragment of a variant of SEQ ID NO: 1 having IgG degrading cysteine protease activity.

(d) the amino acid sequence of SEQ ID NO: 3;

(e) a variant of SEQ ID NO: 3 having at least 70% identity to the amino acid sequence of SEQ ID NO: 3 and having IgG degrading cysteine protease activity;

(f) a fragment of SEQ ID NO: 3 or a fragment of a variant of SEQ ID NO: 3 having IgG degrading cysteine protease activity;

(g) the amino acid sequence of SEQ ID NO: 5;

(h) a variant of SEQ ID NO: 5 having at least 70% identity to the amino acid sequence of SEQ ID NO: 5 and having IgG degrading cysteine protease activity;

(i) a fragment of SEQ ID NO: 5 or a fragment of a variant of SEQ ID NO: 5 having IgG degrading cysteine protease activity;

(j) the amino acid sequence of SEQ ID NO: 7;

(k) a variant of SEQ ID NO: 7 having at least 70% identity to the amino acid sequence of SEQ ID NO: 7 and having IgG degrading cysteine protease activity; or (l) a fragment of SEQ ID NO: 7 or a fragment of a variant of SEQ ID NO: 7 having IgG degrading cysteine protease activity; or (m) the amino acid sequence of SEQ ID NO: 9;

(n) a variant of SEQ ID NO: 9 having at least 70% identity to the amino acid sequence of SEQ ID NO: 9 and having IgG degrading cysteine protease activity;

(o) a fragment of SEQ ID NO: 9 or a fragment of a variant of SEQ ID NO: 9 having IgG degrading cysteine protease activity;

(p) the amino acid sequence of SEQ ID NO: 11;

(q) a variant of SEQ ID NO: 11 having at least 70% identity to the amino acid sequence of SEQ ID NO: 11 and having IgG degrading cysteine protease activity; or (r) a fragment of SEQ ID NO: 11 or a fragment of a variant of SEQ ID NO: 11 having IgG degrading cysteine protease activity.

5. A polynucleotide encoding a polypeptide according to aspect 4 for use in treatment or prevention of a disease or condition mediated by IgG antibodies.

6. An in vitro method for the cleavage of IgG, comprising contacting IgG with a polypeptide comprising:

(a) the amino acid sequence of SEQ ID NO: 1;

(b) a variant of SEQ ID NO: 1 having at least 70% identity to the amino acid sequence of SEQ ID NO: 1 and having IgG degrading cysteine protease activity;

(c) a fragment of SEQ ID NO: 1 or a fragment of a variant of SEQ ID NO: 1 having IgG degrading cysteine protease activity.

(d) the amino acid sequence of SEQ ID NO: 3;

(e) a variant of SEQ ID NO: 3 having at least 70% identity to the amino acid sequence of SEQ ID NO: 3 and having IgG degrading cysteine protease activity;

(f) a fragment of SEQ ID NO: 3 or a fragment of a variant of SEQ ID NO: 3 having IgG degrading cysteine protease activity;

(g) the amino acid sequence of SEQ ID NO: 5;

(h) a variant of SEQ ID NO: 5 having at least 70% identity to the amino acid sequence of SEQ ID NO: 5 and having IgG degrading cysteine protease activity;

(i) a fragment of SEQ ID NO: 5 or a fragment of a variant of SEQ ID NO: 5 having IgG degrading cysteine protease activity;

(j) the amino acid sequence of SEQ ID NO: 7;

(k) a variant of SEQ ID NO: 7 having at least 70% identity to the amino acid sequence of SEQ ID NO: 7 and having IgG degrading cysteine protease activity;

(l) a fragment of SEQ ID NO: 7 or a fragment of a variant of SEQ ID NO: 7 having IgG degrading cysteine protease activity;

(m) the amino acid sequence of SEQ ID NO: 9;

(n) a variant of SEQ ID NO: 9 having at least 70% identity to the amino acid sequence of SEQ ID NO: 9 and having IgG degrading cysteine protease activity;

(o) a fragment of SEQ ID NO: 9 or a fragment of a variant of SEQ ID NO: 9 having IgG degrading cysteine protease activity;

(p) the amino acid sequence of SEQ ID NO: 11;

(q) a variant of SEQ ID NO: 11 having at least 70% identity to the amino acid sequence of SEQ ID NO: 11 and having IgG degrading cysteine protease activity; or (r) a fragment of SEQ ID NO: 11 or a fragment of a variant of SEQ ID NO: 11 having IgG degrading cysteine protease activity.

7. A method for identifying a substance that activates or inhibits the IgG cysteine activity of an IgdE polypeptide comprising the steps;

a) contacting the IgdE polypeptide and IgG with a candidate substance under conditions permitting IgG cysteine activity in the absence of the substance, b) determining the amount of IgG digested in the presence of the candidate substance compared to in the absence of said substance, c) based on the results obtain in b) determining whether the substance activates or inhibits the IgG cysteine activity of the IgdE polypeptide.

The invention claimed is:

1. An in vitro method for the cleavage of human IgG1, the method comprising contacting human IgG1 with a purified polypeptide in vitro, wherein the purified polypeptide comprises:
   (a) the amino acid sequence of SEQ ID NO: 3;
   (b) a variant thereof having at least 95% identity to the amino acid sequence of SEQ ID NO: 3 and having human IgG1 cysteine protease activity; or
   (c) a fragment thereof of either (a) or (b), having human IgG1 cysteine protease activity.

2. A method according to claim 1, wherein the purified polypeptide comprises the amino acid sequence of SEQ ID NO: 3.

3. A method according to claim 1, wherein the method comprises incubating the purified polypeptide with a sample containing human IgG1 under conditions which permit specific cysteine protease activity to occur.

4. A method according to claim 1, which further comprises identification and/or isolation of the cleavage products.

5. A method according to claim 4, wherein said identification and/or isolation comprises analysis by gel electrophoresis or mass spectrometry.

6. A method according to claim 1, wherein the method is used to generate Fc and Fab fragments.

7. A method according to claim 1, wherein the method is used to detect human IgG1.

8. A method according to claim 7, comprising:
   (i) contacting a sample with the purified polypeptide under conditions that permit the human IgG1 specific cysteine protease activity of the polypeptide; and
   (ii) monitoring for the presence of human IgG1 specific cleavage fragments; wherein the presence of the specific cleavage fragments is indicative of human IgG1 in the sample.

9. A method according to claim 1, wherein the purified polypeptide is a purified recombinant polypeptide.

* * * * *